United States Patent
Zhu et al.

(10) Patent No.: US 9,074,197 B2
(45) Date of Patent: Jul. 7, 2015

(54) HIGH FIDELITY RESTRICTION ENDONUCLEASES

(71) Applicant: New England Biolabs, Inc., Ipswich, MA (US)

(72) Inventors: Zhenyu Zhu, Beverly, MA (US); Aine Quimby, Newton, NH (US); Shuang-Yong Xu, Lexington, MA (US); Shengxi Guan, Stoneham, MA (US); Hua Wei, Ipswich, MA (US); Penghua Zhang, Lexington, MA (US); Dapeng Sun, Arlington, MA (US); Siu-hong Chan, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 361 days.

(21) Appl. No.: 13/736,561

(22) Filed: Jan. 8, 2013

(65) Prior Publication Data

US 2013/0115678 A1    May 9, 2013

Related U.S. Application Data

(62) Division of application No. 12/172,963, filed on Jul. 14, 2008, now Pat. No. 8,372,619.

(60) Provisional application No. 60/959,203, filed on Jul. 12, 2007.

(51) Int. Cl.
   *C12N 9/22*   (2006.01)
   *C12N 9/16*   (2006.01)
   *C12N 15/10*  (2006.01)

(52) U.S. Cl.
   CPC .. *C12N 9/16* (2013.01); *C12N 9/22* (2013.01); *C12N 15/1058* (2013.01); *C12N 15/1034* (2013.01)

(58) Field of Classification Search
   CPC ....................................................... C12N 9/22
   See application file for complete search history.

(56) References Cited

FOREIGN PATENT DOCUMENTS

WO    2007027464    3/2007

OTHER PUBLICATIONS

Form PCT/ISA/220, Search Report and Written Opinion for Application PCT/US2009/069997, mailed Jan. 20, 2009.
Form PCT/ISA/206, Invitation to Pay additional Fees for Application PCT/US2008/067737, mailed Nov. 11, 2008.
Roberts, R.J., Proc Natl Acad Sci U S A, 102:5905-5908 (2005).
Roberts, et al., Nucleic Acids Res, 31:1805-1812 (2003).
Roberts, et al., Nucleic Acids Res, 33:D230-232 (2005).
Alves, et al., Restriction Endonucleases, "Protein Engineering of Restriction Enzymes," ed. Pingoud, Springer-Verlag Berlin Heidelberg, New York, 393-407 (2004).
Raleigh, et al., Bacterial Genomes Physical Structure and Analysis, Ch.8, eds. De Bruijin, et al., Chapman & Hall, New York, 78-92 (1998).
Arber, W. Science, 205:361-365 (1979).
Carlson, et al., Mol Microbiol, 27:671-676 (1998).
Heitman, J., Genet Eng (N Y), 15:57-108 (1993).
McKane, et al., Genetics, 139:35-43 (1995).
Danna, et al., Proc Natl Acad Sci U S A, 68:2913-2917 (1971).
Kelly, et al., J Mol Biol, 51:393-409 (1970).
Polisky, et al., Proc Natl Acad Sci U S A, 72:3310-3314 (1975).
Nasri, et al., Nucleic Acids Res, 14:811-821 (1986).
Robinson, et al., J Mol Biol, 234:302-306 (1993).
Robinson, et al., Proc Natl Acad Sci U S A, 92:3444-3448 (1995).
Sidorova, et al., Biophys J, 87:2564-2576 (2004).
Walker, et al., Proc Natl Acad Sci U S A, 89:392-396 (1992).
Velculescu, et al., Science, 270:484-487 (1995).
Chen, et al., Biotechniques, 38:198-204 (2005).
Wei, H., et al., Nucleic Acid Res., 36:9, e50 (2008).
Samuelson, et al., J. Mol. Biol., 319(3):673-83 (2002).
Zhu, et al., J. Mo. Biol., 330(2):359-72 (2003).

*Primary Examiner* — Rebecca Prouty
(74) *Attorney, Agent, or Firm* — New England Biolabs, Inc.; Harriet M. Strimpel

(57) ABSTRACT

Compositions and methods are provided for enzymes with altered properties that involve a systematic approach to mutagenesis and a screening assay that permits selection of the desired proteins. Embodiments of the method are particularly suited for modifying specific properties of restriction endonucleases such as star activity. The compositions includes restriction endonucleases with reduced star activity as defined by an overall fidelity index improvement factor.

12 Claims, 2 Drawing Sheets

HIGH FIDELITY RESTRICTION ENDONUCLEASES

CROSS REFERENCE

This application is a divisional of U.S. Ser. No. 12/172,963 filed Jul. 14, 2008, now U.S. Pat. No. 8,372,619, which claims priority from U.S. provisional application Ser. No. 60/959,203 filed Jul. 12, 2007, herein incorporated by reference.

BACKGROUND

Restriction endonucleases are enzymes that cleave double-stranded DNAs in a sequence-specific manner (Roberts, R. J., Proc Natl Acad Sci USA, 102:5905-5908 (2005); Roberts, et al., Nucleic Acids Res, 31:1805-1812 (2003); Roberts, et al., Nucleic Acids Res, 33:D230-232 (2005); Alves, et al., Restriction Endonucleases, "Protein Engineering of Restriction Enzymes," ed. Pingoud, Springer-Verlag Berlin Heidelberg, New York, 393-407 (2004)). They are ubiquitously present among prokaryotic organisms (Raleigh, et al., Bacterial Genomes Physical Structure and Analysis, Ch. 8, eds. De Bruijin, et al., Chapman & Hall, New York, 78-92 (1998)), in which they form part of restriction-modification systems, which mainly consist of an endonuclease and a methyltransferase. The cognate methyltransferase methylates the same specific sequence that its paired endonuclease recognizes and renders the modified DNA resistant to cleavage by the endonuclease so that the host DNA can be properly protected. However, when there is an invasion of foreign DNA, in particular bacteriophage DNA, the foreign DNA will be degraded before it can be completely methylated. The major biological function of the restriction-modification system is to protect the host from bacteriophage infection (Arber, Science, 205:361-365 (1979)). Other functions have also been suggested, such as involvement in recombination and transposition (Carlson, et al., Mol Microbiol, 27:671-676 (1998); Heitman, Genet Eng (NY), 15:57-108 (1993); McKane, et al., Genetics, 139:35-43 (1995)).

The specificity of the approximately 3,000 known restriction endonucleases for their greater than 250 different target sequences could be considered their most interesting characteristic. After the discovery of the sequence-specific nature of the first restriction endonuclease (Danna, et al., Proc Natl Acad Sci USA, 68:2913-2917 (1971); Kelly, et al., 3 Mol Biol, 51:393-409 (1970)), it did not take long for scientists to find that certain restriction endonucleases cleave sequences which are similar but not identical to their defined recognition sequences under non-optimal conditions (Polisky, et al., Proc Natl Acad Sci USA, 72:3310-3314 (1975); Nasri, et al., Nucleic Acids Res, 14:811-821 (1986)). This relaxed specificity is referred to as star activity of the restriction endonuclease. It has been suggested that water-mediated interactions between the restriction endonuclease and DNA are the key differences between specific complexes and star complexes (Robinson, et al., J Mol Biol, 234:302-306 (1993); Robinson, et al., Proc Natl Acad Sci USA, 92:3444-3448 (1995); Sidorova, et al., Biophys J, 87:2564-2576 (2004)).

Star activity is a problem in molecular biology reactions. Star activity introduces undesirable cuts in a cloning vector or other DNA. In cases such as forensic applications, where a certain DNA substrate needs to be cleaved by a restriction endonuclease to generate a unique fingerprint, star activity will alter a cleavage pattern profile, thereby complicating analysis. Avoiding star activity is also critical in applications such as strand displacement amplification (Walker, et al., Proc Nat/Acad Sci USA, 89:392-396 (1992)) and serial analysis of gene expression (Velculescu, et al., Science, 270:484-487 (995)).

SUMMARY

In an embodiment of the invention, a composition is provided that includes a restriction endonuclease having at least one artificially introduced mutation and an overall fidelity index (FI) improvement factor of at least two, the restriction endonuclease being capable of cleaving a substrate with at least a similar cleavage activity to that of the restriction endonuclease absent the artificially introduced mutation in a predetermined buffer, the artificially introduced mutation being the product of at least one of a targeted mutation, saturation mutagenesis, or a mutation introduced through a PCR amplification procedure.

In a further embodiment of the invention, at least one of the artificially introduced mutations is a targeted mutation resulting from replacement of a naturally occurring residue with an oppositely charged residue. An Alanine or a Phenylalanine may replace the naturally occurring residue at the target site.

In a further embodiment of the invention, a composition of the type described above includes a restriction enzyme absent the artificially introduced mutation selected from the group consisting of: BamHI, EcoRI, ScaI, SalI, SphI, PstI, NcoI, NheI, SspI, NotI, SacI, PvuII, MfeI, HindIII, SbfI, EagI, EcoRV, AvrII, BstXI, PciI, HpaI, AgeI, BsmBI, BspQI, SapI, KpnI and BsaI.

Further embodiments of the invention include compositions listed in Table 4.

In a further embodiment of the invention, a DNA encoding any of the enzymes listed in Table 4 is provided, a vector comprising the DNA and a host cell for expressing the protein from the vector.

In an embodiment of the invention, a method is provided having the steps of (a) identifying which amino acid residues in an amino acid sequence of a restriction endonuclease having star activity are charged amino acids; (b) mutating one or more codons encoding one or more of the charged residues in a gene sequence encoding the restriction endonuclease; (c) generating a library of gene sequences having one or more different codon mutations in different charged residues; (d) obtaining a set of proteins expressed by the mutated gene sequences; and (e) determining an FI in a predetermined buffer and a cleavage activity for each expressed protein.

An embodiment of the method includes the step of determining an overall FI improvement factor for proteins belonging to the set of proteins in a defined set of buffers where for example, the set of buffers contains NEB1, NEB2, NEB3 and NEB4 buffers.

An embodiment of the method includes the steps described above and additionally mutating codons encoding hydroxylated amino acids or amide amino acids in a same or subsequent step to that of mutating codons for the charged amino acids.

In an embodiment of the invention described above, the codons are mutated to an Alanine except for Tyrosine which is mutated to a Phenylalanine.

In a further embodiment, the overall FI improvement factor is improved using saturation mutagenesis of one or more of the mutated codon.

BRIEF DESCRIPTION OF THE DRAWINGS

In each of the reactions described in FIGS. 1-2A-B, the reaction mixture contains a volume of 3 µl unless otherwise specified of a buffer from New England Biolabs, Inc. (NEB), Ipswich, Mass., (see Table 1 and NEB catalog), 3 µl unless otherwise specified of a specified restriction endonuclease in a diluent from NEB, Ipswich, Mass. (See Table 1 and NEB catalog) as well as variable volumes of specified substrate (containing 0.6 µg) substrate and a volume of water to bring the reaction mixture to a total of 30 µl. Reactions were conducted at 37° C. for an incubation time of 1 hour. The results are analyzed on a 0.8% agarose gel. Where the overall volume of the reaction mix, amount of substrate, temperature of the reaction or incubation time varies from above, values are provided in the description of the figures.

Figure 2A:
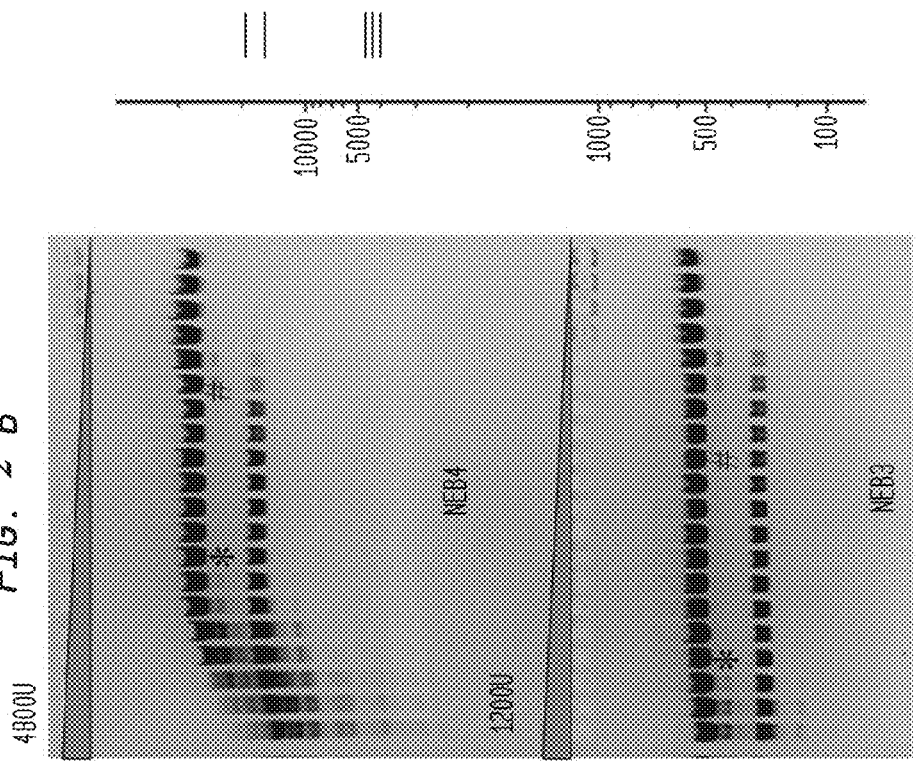
Figure 2B:
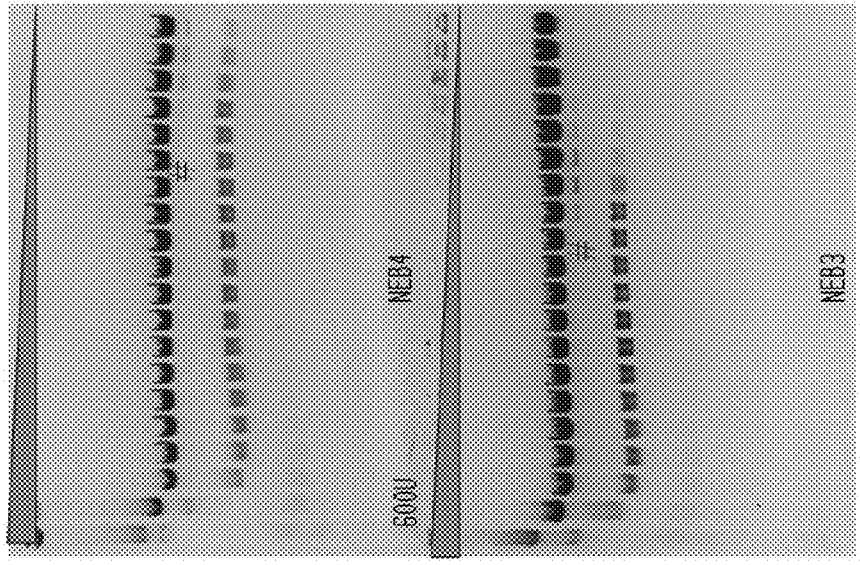

For FIGS. 2A-B:

The * symbol indicates the lane to its left that contains the lowest concentration of enzyme for which star activity is observed.

The # symbol refers to the lane showing incomplete cleavage, which is adjacent to and to the right side of the lane containing a concentration of enzyme sufficient for complete cleavage of the substrate.

"U" denotes units of enzyme.

FIGS. 2A-B show cleavage of 1.2 µl lambda DNA substrate using 2-fold serial dilutions of NcoI-HF (4,800 U and 600 U) and 2-fold serial dilutions of WT NcoI (4,800 U and 1,200 U) in NEB3 and NEB4 buffers, respectively. Serial dilutions were performed in diluent A.

FIG. 2A shows cleavage by NcoI-HF in NEB4 buffer (upper panel) and NEB3 buffer (lower panel).

FIG. 2B shows cleavage by WT NcoI in NEB4 buffer (upper panel) and NEB3 buffer (lower panel).

Figure 1:
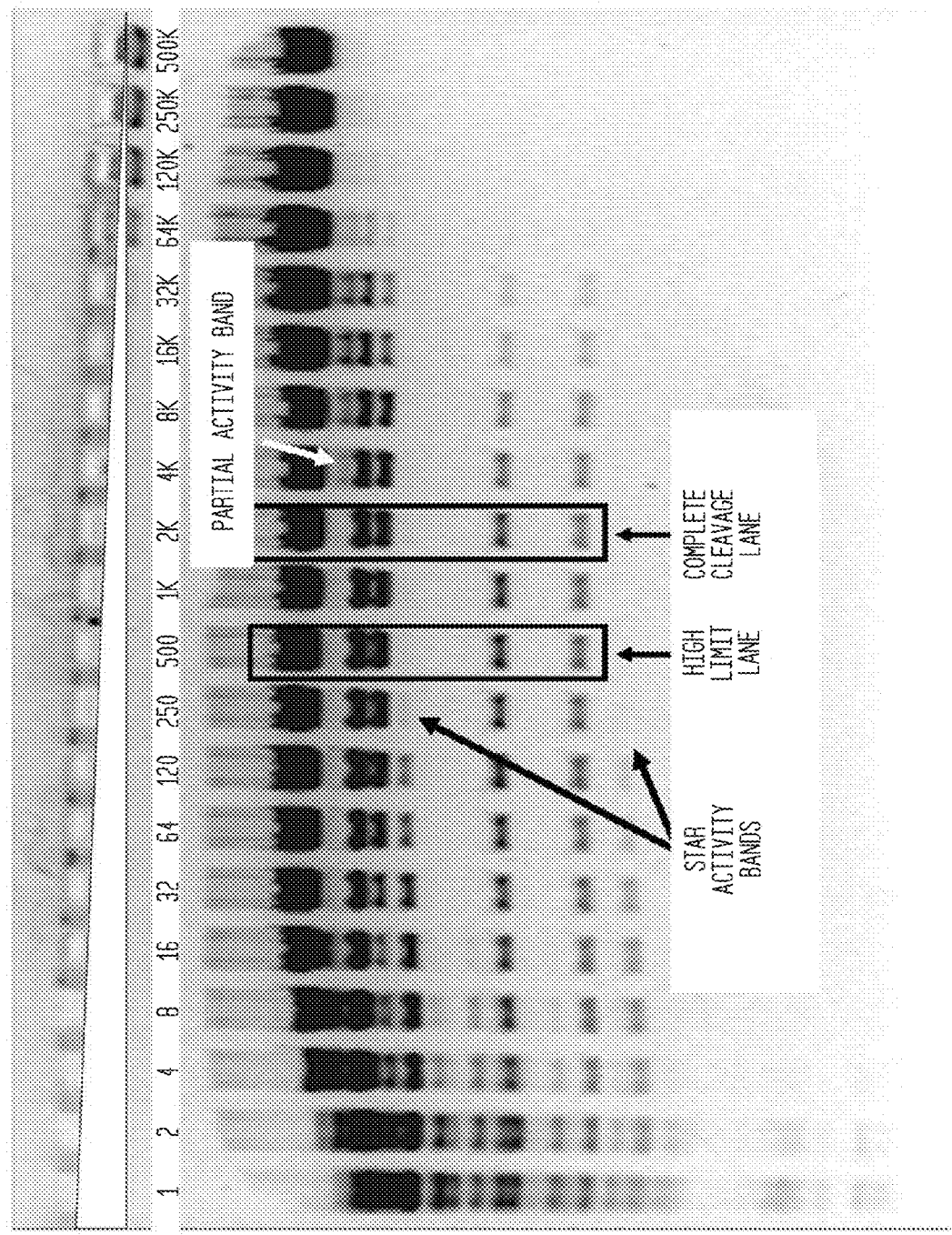
FIG. 1 shows the determination of the FI for wild type (WT) ScaI by digesting 1.2 µl lambda DNA substrate (0.6 µg) with a two-fold serial dilution using diluent A of a preparation of WT ScaI (1,200 U) in NEB3 buffer and examining the digestion products on an agarose gel. The highest concentration of a restriction endonuclease with no star activity is shown with a solid arrow; and the minimum concentration giving rise to complete digestion of substrate is shown with a hollow arrow.

The theoretical digestion pattern is provided on the right side of the gel for FIGS. 1-2A-B. Those substrates with only one restriction endonuclease site should be digested into one linear band from supercoiled form.

DETAILED DESCRIPTION OF THE EMBODIMENTS

Embodiments of the invention provide a general method for selecting for restriction endonucleases with desired characteristics. The general method relies on a suitable assay for determining whether the desired restriction endonuclease has been created. In particular an embodiment of the general method provides a systematic screening method with a set of steps. This method has been deduced by performing many hundreds of reactions using many restriction endonucleases. The example provided herein relates to identifying a restriction endonuclease with reduced star activity but with cleavage activity that is at least similar to the WT restriction endonuclease. However, it is expected that the same methodology can be applied successfully to modifying other properties of the restriction endonucleases relating, for example, to improved cleavage activity in desired buffers, thermostability, rate of reaction in defined conditions, etc.

As discussed above, an end point of interest is to transform restriction endonucleases with star activity into high fidelity restriction endonucleases with significantly reduced star activity. Star activity refers to promiscuity in cleavage specificity by individual restriction endonucleases. The terms "reduction in star activity" and "increase in fidelity" are used interchangeably here. Although restriction endonucleases are characterized by their property of cleaving DNA at specific sequences, some restriction endonucleases additionally cleave DNA inefficiently at secondary sites in the DNA. This secondary cleavage may occur consistently or may arise only under certain conditions such as any of: increased concentrations, certain buffers, temperature, substrate type, storage, and incubation time.

It is generally acknowledged that little is known about the complex environment generated by the hundreds of amino acids that constitute a protein and determine specificity. One approach in the prior art has been to utilize crystallography to identify contact points between an enzyme and its substrate. Nonetheless, crystallography has limitations with respect to freezing a structure in time in an unnatural chemical environment.

The rules that determine the contribution of amino acids at any site in the protein and the role played by the structure of the substrate molecule has proved elusive using existing analytical techniques. For example, it is shown here that mutating an amino acid in a restriction endonuclease can cause all or partial loss of activity.

In this context, no structural explanation has been put forward to explain why star activity could increase with high glycerol concentration (>5% v/v), high enzyme to DNA ratio (usually >100 units of enzyme per µg of DNA), low ionic strength (<25 mM salt), high pH (>8.0), presence of organic solvent (such as DMSO, ethanol), and substitution of $Mg^{2+}$ with other divalent cations ($Mn^{2+}$, $Co^{2+}$). It was here recognized that because of the diversity of factors affecting star activity, it would be necessary to conduct comparisons of WT and mutant star activity under the same reaction conditions and in the same predetermined buffer and to develop a standard reaction condition in which any high fidelity enzyme must be capable of showing the described characteristics even if these characteristics were also observed in other reaction conditions.

Present embodiments of the invention are directed to generating modified restriction endonucleases with specific improved properties, namely enhanced cleavage fidelity without significant reduction in overall cleavage activity or significant loss of yield from the host cells that make the protein. The methods that have been developed here for finding mutants with improved properties have resulted from exhaustive experimentation and the properties of the resultant enzymes have been defined in the context of specified conditions. The methods described herein may be used for altering the enzymatic properties of any restriction endonuclease under predetermined conditions, but are not limited to the specific defined conditions.

| Restriction Endonuclease | Steps Used to Generate a High Fidelity Restriction Endonuclease |
|---|---|
| BamHI | Comparison of isoschizomer<br>Targeted 22 residues to mutate to Ala. 14 mutants obtained, 3 |

-continued

| Restriction Endonuclease | Steps Used to Generate a High Fidelity Restriction Endonuclease |
|---|---|
| | had improved fidelity<br>Saturation mutagenesis on 2 residues-K30 and E86<br>Recovered E86P as preferred mutant with greatest reduced star activity in selected buffers. Added mutations to E86P.<br>Second round of mutation (Arg, Lys, His, Asp, Glu, Ser, Thr) to Ala and Tyr to Phe. Selected E167 and Y165 for saturation mutagenesis and selected E167T and Y165F.<br>E163A/E167T was selected as preferred high fidelity mutant (BamHI-HF). |
| EcoRI | Comparison of isoschizomer<br>Targeted 42 charged residues to mutate to Ala. No high fidelity mutants<br>Second round of mutation: Target additional 32 charged residues to mutate to Ala: Identified K62A.<br>Saturation mutagenesis on K62A. EcoRI(K62E) was selected as a preferred high fidelity mutant (EcoRI-HF). |
| ScaI | Comparison of isoschizomers.<br>Targeted 58 charged residues to mutate to Ala. Identify 4 mutants<br>Preferred mutant of 4 is (H193A/S201F). This is selected as a preferred high fidelity mutant (ScaI-HF) |
| SalI | Target 86 charged residues and mutate to Ala. SalI (R107A) was preferentially selected as a preferred high fidelity mutant (SalI-HF). |
| SphI | Target 71 charged residues and mutate to Ala. SphI (K100A) was preferentially selected as a preferred high fidelity mutant (SphI-HF) |
| PstI | Target 92 charged amino acids and mutate to Ala. PstI (D91A) was preferentially selected as a preferred high fidelity mutant (PstI-HF) |
| NcoI (Ex. 1) | Target 66 charged residues and mutate to Ala. NcoI (A2T/R31A) was preferentially selected as a preferred high fidelity mutant (NcoI-HF). |
| NheI | Target 92 charged residues and mutate to Ala. NheI (E77A) was preferentially selected as a preferred high fidelity mutant (NheI-HF) |
| SspI | Target 81 charged residues and mutate to Ala. No preferential mutants obtained.<br>Target 95 residues to additional charged residues and hydroxylated residues to Ala except Tyr. Tyr mutated to Phe. SspI (Y98F) was preferentially selected as a preferred high fidelity mutant (SspI-HF) |
| NotI | Target 97 charged residues and mutate to Ala. K150A was preferentially selected as a preferred high fidelity mutant (NotIHF) |
| SacI | Target 101 charged residues and mutate to Ala. SacI (Q117H/R200A) was preferentially selected as a preferred high fidelity mutant (SacI-HF) where Q117H was a carry over mutation from template with no affect on activity |
| PvuII | Target 47 charged residues and mutate to Ala. No preferred mutants obtained<br>Target 19 hydroxylated residues - Ser/Thr and Tyr. Select T46A for further improvement<br>Saturation mutagenesis results in a preferred mutant T46G, T46H, T46K, T46Y. PvuII(T46G) was preferentially selected as a preferred high fidelity mutant (PvuII-HF) |
| MfeI | Target 60 charged residues and mutate to Ala. No preferred mutants obtained<br>Target 26 hydroxylated residues and mutate to Ala except for Tyr which was changed to Phe.<br>Target 38 residues (Cys, Phe, Met, Asn, Gln, Trp) and mutate to Ala<br>Identify Mfe (Q13A/F35Y) as a preferred high fidelity mutant (MfeI-HF) where F35Y is carried from the template |
| HindIII | Target 88 charged residues and mutate to Ala. No preferred mutants obtained<br>Target 103 residues (Cys Met Asn, Gln, Ser Thr Trp) and mutate to Ala and Tyr changed to Phe.<br>Identify HindIII (K198A) as a preferred high fidelity mutant (HindIII-HF) |
| SbfI | Target 78 charged residues mutated to Ala<br>Target 41 residues (Ser Thr) mutated to Ala/Tyr to Phe<br>Target 55 residues of Cys, Phe, Met Asn, Gln, Trp to Ala<br>SbfI (K251A) was selected as a preferred high fidelity mutant (SbfI-HF) |

| Restriction Endonuclease | Steps Used to Generate a High Fidelity Restriction Endonuclease |
|---|---|
| EagI | Target 152 residues (Asp, Glu, His, Lys, Arg, Ser, thr, Asn, and Gln changed to Ala and Tyr changed to Phe). EagI H43A was selected as a preferred high fidelity mutant (EagIHF) |
| EcoRV | Target 162 residues (Cys, Asp, Glu, Phe, his, Lys, Met, Asn, Gln, Arg, Ser, Thr, to Ala and Trp to Phe) EcoRV (D19A/E27A) was selected as a preferred high fidelity mutant (EcoRV-HF) |
| AvrII | Target 210 residues (Cys, Asp, Glu, Phe, his, Lys, Met, Asn, Gln, Arg, Ser, Thr, to Ala and Trp to Phe) AvrII (Y104F) was selected as a preferred high fidelity mutant (AvrII-HF) |
| BstXI | Target 237 residues (Cys, Asp, Glu, Phe, his, Lys, Met, Asn, Gln, Arg, Ser, Thr, to Ala and Trp to Phe) BstXI (N65A) was selected as a preferred high fidelity mutant (BstXI-HF) |
| PciI | Target 151 residues (Cys, Asp, Glu, Phe, his, Lys, Met, Asn, Gln, Arg, Ser, Thr, to Ala and Trp to Phe) PciI (E78A/S133A) was selected as a preferred high fidelity mutant. (PciI-HF) This was spontaneous and not one of the 151 separate mutations |
| HpaI | Target 156 residues (Cys, Asp, Glu, Phe, his, Lys, Met, Asn, Gln, Arg, Ser, Thr, to Ala and Trp to Phe) HpaI (E56A) was selected as a preferred high fidelity mutant (HpaI-HF) |
| AgeI | Target 149 residues (Cys, Asp, Glu, Phe, his, Lys, Met, Asn, Gln, Arg, Ser, Thr, to Ala and Trp to Phe) AgeI (R139A) was selected as a preferred high fidelity mutant (AgeI-HF) |
| BsmBI | Target 358 residues (Cys, Asp, Glu, Phe, his, Lys, Met, Asn, Gln, Arg, Ser, Thr, to Ala and Trp to Phe) BsmBI(N185Y/R232A) was selected as a preferred high fidelity mutant (BsmBI (HF) |
| BspQI | Target 122 residues (Arg, Lys, His, Glu, Asp, Gln, Asn, Cys) Replace R at position 279 with Phe, Pro, Tyr, Glu, Asp or Leu. Preferred mutations were R388F and K279P. Created a double mutant BspQI(K279P/R388F) as preferred high fidelity mutant (BspQI-HF) |
| SapI | Find K273 and R380 in SapI corresponding to R388 and K279 in BspQI. SapI (K273P/R380F) was selected as a preferred high fidelity mutant (SapI-HF) |
| KpnI | Target all residues (Asp, Glu, Arg, Lys, His, Ser, Thr, Tyr, Asn, Gln, Phe, Trp, Cys, Met) to Ala. More mutation was done on site D16 and D148. A combined D16N/E132A/D148E was selected as a preferred high fidelity mutant (KpnI-HF). |
| BsaI | Find 11 amino acids corresponding to the site in BsmBI. BsaI (Y231F) was selected as a preferred high fidelity mutant (BsaI-HF). |

The method follows from the realization that amino acids responsible for cognate activity and star activity are different. The engineering of high fidelity restriction endonucleases described herein demonstrates that cognate activity and star activity can be separated and there are different critical amino acid residues that affect these different activities. The locations of amino acids that are here found to affect star activity are not necessarily found within the active site of the protein. The cleavage properties of any restriction endonuclease has been determined here for the first time by developing a criterion of success in the form of determining a FI (see also Wei, et al. *Nucleic Acid Res.*, 36, 9, e50 (2008)) and an overall fidelity index improvement factor.

An "overall fidelity index improvement factor" refers to the highest FI for a mutant with maximum cleavage activity divided by the highest FI of the corresponding WT endonuclease with maximum cleavage activity within a selected set of buffers. The selected set may be of any size greater than one but practically will contain less than 10 different buffers and more preferably contains 4 buffers. The set may also include less than 4 buffers. The overall FI improvement factor of at least two should preferably be applicable for any mutant restriction endonuclease in the claimed invention additionally but not exclusively to the set of buffers consisting of NEB1, NEB2, NEB3 and NEB4.

A "similar cleavage activity" can be measured by reacting the same amount of enzyme with the same amount and type of substrate under the same conditions and visually comparing the cleavage profiles on a gel after electrophoresis such that the amount of cleavage product appears to be the same within a standard margin of error and wherein the quantitative similarity is more than 10%.

"Artificial" refers to "man-made".

"Standard conditions" refers to an overall FI improvement factor calculated from results obtained in NEB1-4 buffers.

The general method described herein has been exemplified with 27 restriction endonucleases: AgeI, AvrII, BamHI, BsaI, BsmBI, BspQI, BstXI, EagI, EcoRI, EcoRV, HindIII, HpaI, KpnI, MfeI, NcoI, NheI, NotI, PciI, PstI, PvuII, SacI, SalI, SapI, SbfI, ScaI, SphI and SspI restriction endonucleases. However, as mentioned above, the method is expected to be effective for the engineering of any restriction endonuclease that has significant star activity.

Embodiments of the method utilize a general approach to create mutant restriction endonucleases with reduced star activity. For certain enzymes, it has proven useful to mutate charged residues that are determined to be conserved between two isoschizomers. In general, however, the method involves a first step of identifying all the charged and polar residues in a protein sequence for the endonuclease. For example, charged amino acids and polar residues include the acidic residues Glu and Asp, the basic residues His, Lys and Arg, the amide residues Asn and Gln, the aromatic residues Phe, Tyr and Trp and the nucleophilic residue Cys. Individual residues are targeted and mutated to an Ala and the products of these targeted mutations are screened for the desired properties of increased fidelity. If none of the mutants obtained provide a satisfactory result, the next step is to target mutations to all the hydroxylated amino acids, namely, Ser, Thr and Tyr, the preferred mutation being Ser and Thr to Ala and Tyr to Phe. It is also possible to target mutations to both classes of residues at one time. The mutation to Ala may be substituted by mutations to Val, Leu or Ile.

After these analyses, if one or more of the preferred mutants generated in the above steps still have substandard performance under the selected tests, these mutants can be selected and mutated again to each of the additional possible 18 amino acids. This is called saturation mutagenesis. Saturation mutagenesis provided the preferred high fidelity mutants for EcoRI, BamHI in part and PvuII. Depending on the results of saturation mutagenesis, the next step would be to introduce additional mutations either targeted or random or both into the restriction endonuclease. SacI-HF includes a random mutation generated fortuitously during inverse PCR. PciI-HF resulted from a random mutation and not from targeted mutations. BspQI-HF contains two mutations that were found to act synergistically in enhancing fidelity.

The use of various methods of targeted mutagenesis such as inverse PCR may involve the introduction of non-target mutations at secondary sites in the protein. These secondary mutations may fortuitously provide the desired properties. It is desirable to examine those mutated enzymes with multiple mutations to establish whether all the mutations are required for the observed effect. Q117H in the double mutant had no effect on activity.

In some cases, a mutation may provide an additional advantage other than improved fidelity.

The high fidelity/reduced star activity properties of the mutants provided in the Examples were selected according to their function in a set of standard buffers. Other mutations may be preferable if different buffer compositions were selected. However, the same methodology for finding mutants would apply. Table 4 lists mutations which apply to each restriction endonuclease and provide an overall FI improvement factor in the standard buffer.

The engineering of the high fidelity restriction endonucleases to provide an overall FI improvement factor of at least 2 involves one or more of the following steps:

1. Assessment of the Star Activity of the WT Restriction Endonuclease

In an embodiment of the invention, the extent of star activity of a restriction endonuclease is tested by means of the following protocol: the endonuclease activity is determined for an appropriate substrate using a high initial concentration of a stock endonuclease and serial dilutions thereof (for example, two-fold or three-fold dilutions). The initial concentration of restriction endonuclease is not important as long as it is sufficient to permit an observation of star activity in at least one concentration such that on dilution, the star activity is no longer detected.

An appropriate substrate contains nucleotide sequences that are cleaved by cognate endonuclease activity and where star activity can be observed. This substrate may be the vector containing the gene for the restriction endonuclease or a second DNA substrate. Examples of substrates used in Table 2 are pBC4, pXba, T7, lambda, and pBR322.

The concentration of stock restriction endonuclease is initially selected so that the star activity can be readily recognized and assayed in WT and mutated restriction endonucleases. Appropriate dilution buffers such as NEB diluent A, B or C is selected for performing the serial dilutions according to guidelines in the 2007-08 NEB catalog. The serially diluted restriction endonuclease is reacted with a predetermined concentration of the appropriate substrate in a total reaction volume that is determined by the size of the reaction vessel. For example, it is convenient to perform multiple reactions in microtiter plates where a 30 µl reaction mixture is an appropriate volume for each well. Hence, the examples generally utilize 0.6 µg of substrate in 30 µl, which is equivalent to 1 µg of substrate in 50 µl. The amount of substrate in the reaction mixture is not critical, but it is preferred that it be constant between reactions. The cleavage reaction occurs at a predetermined temperature (for example 25° C., 30° C., 37° C., 50° C., 55° C. or 65° C.) for a standard time such as one hour. The cleavage products can be determined by any standard technique, for example, by 0.8% agarose gel electrophoresis to determine the fidelity indices as defined above.

Not all restriction endonucleases have significant star activity as determined from their FI. However, if an endonuclease has a highest FI of no more than about 250 and a lowest FI of less than 100, the restriction endonuclease is classified as having significant star activity. Such endonucleases are selected as a target of enzyme engineering to increase fidelity for a single substrate. In some cases, the restriction endonucleases with both FI over about 500 and FI less than about 100 are also engineered for better cleavage activity.

Table 2 below lists the FI of some engineered restriction endonucleases before engineering. All samples were analyzed on 0.8% agarose gel.

TABLE 2

| Enzyme | Diluent (NEB) *** | Substrate * | Temp ° C. | FI-1 ** | FI-2 ** | FI-3 ** | FI-4 ** |
|---|---|---|---|---|---|---|---|
| AgeI | C | pXba | 37 | 16 (1) | 8 (½) | 64 (⅛) | 8 (½) |
| AvrII | B | T7 | 37 | 64 (1) | 8 (1) | 32 (¼) | 32 (1) |
| BamHI | A | λ | 37 | 4 (½) | 4 (1) | 32 (1) | 4 (½) |
| BsaI | B | pBC4 | 50 | 8 (¼) | 120 (1) | 16 (¼) | 32 (1) |
| BsmBI | B | λ | 55 | 1 (⅛) | 8 (½) | 120 (1) | 4 (¼) |
| BspQI | B | λ | 50 | 2 (⅛) | 16 (1) | 32 (1) | 4 (½) |
| BstXI | B | λ | 55 | 2 (½) | 2 (½) | 2 (⅛) | 4 (1) |

TABLE 2-continued

| Enzyme | Diluent (NEB) *** | Substrate * | Temp °C. | FI-1 ** | FI-2 ** | FI-3 ** | FI-4 ** |
|---|---|---|---|---|---|---|---|
| EagI | B | pXba | 37 | 4 (¼) | 8 (½) | 250 (1) | 16 (1) |
| EcoRI | C | λ | 37 | 250 (½) | 4 (1) | 250 (1) | 4 (1) |
| EcoRV | A | pXba | 37 | 32 (1/16) | 120 (½) | 1000 (1) | 64 (¼) |
| HindIII | B | λ | 37 | 32 (¼) | 250 (1) | 4000 (¼) | 32 (½) |
| HpaI | A | λ | 37 | 32 (1/16) | 1 (¼) | 2 (⅛) | 16 (1) |
| KpnI | A | pXba | 37 | 16 (1) | 16 (¼) | 8 (½) | 4 (½) |
| MfeI | A | λ | 37 | 32 (1) | 16 (⅛) | 8 (1/16) | 32 (1) |
| NcoI | A | λ | 37 | 120 (1) | 32 (1) | 120 (¼) | 32 (1) |
| NheI | C | pXba | 37 | 32 (1) | 120 (¼) | 120 (⅛) | 32 (1) |
| NotI | C | pXba | 37 | ≥32000 (1/16) | 64 (1) | 500 (1) | 32 (¼) |
| PciI | A | pXba | 37 | 2000 (½) | 16 (¼) | 120 (1) | 8 (⅛) |
| PstI | C | λ | 37 | 64 (1) | 32 (1) | 120 (1) | 8 (½) |
| PvuII | A | pBR322 | 37 | 250 (1) | 16 (¼) | 8 (1/32) | ¼ (1) |
| SacI | A | pXba | 37 | 120 (1) | 120 (½) | 120 (1/32) | 32 (½) |
| SalI | A | λ (H3) | 37 | 8 (1/500) | 1 (1/16) | 32 (1) | 1 (1/120) |
| SapI | C | λ | 37 | 16 (¼) | 64 (½) | 32 (¼) | 16 (1) |
| SbfI | A | λ | 37 | 32 (1) | 8 (¼) | 8 (1/16) | 8 (½) |
| ScaI | A | λ | 37 | 1/16 (1/32) | ⅛ (1) | 4 (½) | 1/64 (1/16) |
| SphI | B | λ | 37 | 64 (1) | 32 (1) | 64 (¼) | 16 (½) |
| SspI | C | λ | 37 | 64 (1) | 16 (1) | 32 (¼) | 16 (1) |

* Substrate: λ is lambda phage DNA; λ (H3) is HindIII-digested lambda phage DNA; pXba is pUC19 with XbaI-digested fragment of Adeno Virus; pBC4: a shorter version of pXba; T7: T7 DNA
** FI-1 to FI-4: fidelity index of the enzyme in NEBuffer 1, 2, 3 and 4. The number in parenthesis is a value for relative cleavage activity of the mutant restriction endonuclease in a specified buffer in a set of buffers compared with the "best" cleavage activity of the same mutant restriction endonuclease in any of the buffers in the set of buffers.
The compositions of NEB buffers follow:
NEB1: 10 mM Bis Tris Propane-HCl, 10 mM MgCl$_2$, 1 mM dithiothreitol (pH 7.0 at 25° C.);
NEB2: 50 mM NaCl, 10 mM Tris-HCl, 10 mM MgCl$_2$, 1 mM dithiothreitol (pH 7.9 at 25° C.);
NEB3: 100 mM NaCl, 50 mM Tris-HCl, 10 mM MgCl$_2$, 1 mM dithiothreitol (pH 7.9 at 25° C.);
NEB4: 50 mM potassium acetate, 20 mM Tris-acetate, 10 mM magnesium acetate, 1 mM dithiothreitol (pH 7.9 at 25° C.).
*** The compositions of NEB diluents follow. (Using diluents in the dilution instead of water will keep the glycerol concentration in the reaction as a constant.)
Diluent A: 50 mM KCl, 10 mM Tris-HCl, 0.1 mM EDTA, 1 mM dithiothreitol, 200 mg/ml BSA, 50% glycerol (pH 7.4 at 25° C.);
Diluent B: 300 mM NaCl, 10 mM Tris-HCl, 0.1 mM EDTA, 1 mM dithiothreitol, 500 mg/ml BSA, 50% glycerol (pH 7.4 at 25° C.);
Diluent C: 250 mM NaCl, 10 mM Tris-HCl, 0.1 mM EDTA, 1 mM dithiothreitol, 0.15% Triton X-100, 200 mg/ml BSA, 50% glycerol (pH 7.4 at 25° C.).

2. Construction of High Expression Host Cell Strains

It is convenient if a host cell is capable of over-expressing the mutant restriction endonuclease for which reduced star activity is sought. If the restriction enzyme is highly expressed in E. coli, the star activity can be readily detected in the crude extract, which simplifies the screening for the high fidelity restriction endonuclease. However, the mutated restriction endonuclease can be expressed in any host cell providing that the host cell is protected in some way from toxicity arising from enzyme cleavage. This might include: the presence of a methylase; production in a compartment of the cell which provides a barrier to access to the genome (such as an inclusion body or the periplasm); in vitro synthesis; production in an emulsion (see U.S. patent application Ser. No. 12/035,872) absence of cleavage sites in the host genome; manufacture of the enzyme in component parts subject to intein mediated ligation (see U.S. Pat. No. 6,849,428), etc.

Over-expression of the mutated restriction endonucleases for purposes of production can be achieved using standard techniques of cloning, for example, use of an E. coli host, insertion of the endonuclease into a pUC19-derived expression vector, which is a high copy, and use of a relatively small plasmid that is capable of constant expression of recombinant protein. The vector may preferably contain a suitable promoter such as the lac promoter and a multicopy insertion site placed adjacent to the promoter. Alternatively, a promoter can be selected that requires IPTG induction of gene expression. If the activity in the crude extract is not sufficient, a column purification step for the restriction endonuclease in crude extract may be performed.

3. Mutagenesis of Restriction Endonuclease

DNA encoding each charged or polar group in the restriction endonuclease may be individually targeted and the mutated DNA cloned and prepared for testing. Multiple mutations may be introduced into individual restriction endonuclease genes. Targeted mutagenesis of restriction endonucleases may be achieved by any method known in the art. A convenient method used here is inverse PCR. In this approach, a pair of complementary primers that contains the targeted codon plus a plurality of nucleotides (for Example 18 nt) on both the 5' and 3' side of the codon is synthesized. The selection of suitable primers can be readily achieved by reviewing the gene sequence of the endonuclease of interest around the amino acid residue of interest. Access to gene sequences is provided through REBASE and GenBank. The template for PCR is a plasmid containing the restriction endonuclease gene. The polymerase is preferably a high fidelity polymerase such as Vent® or Deep Vent™ DNA polymerase. By varying the annealing temperature and Mg$^{2+}$ concentration, successful introduction of most mutations can be achieved. The PCR amplification product is then purified and preferably digested by DpnI. In an embodiment of the invention, the digested product was transformed into competent host cells (for example, E. coli), which have been pre-modified with a corresponding methylase. Colonies from each mutant were picked and grown under similar conditions to those in which the WT is grown (for example, using similar growth medium, drug selection, and temperature). The resulting restriction endonucleases were screened for reduced star activity.

4. Screening for Mutant Restriction Endonucleases with Reduced Star Activity

Conditions such as buffer composition, temperature and diluent should be defined for determining star activity in a mutant restriction endonuclease. Tables 2 and 3 show the FI of recombinant endonucleases before and after mutation in four different buffers using three different diluents at 37° C. Accordingly, it is possible to determine which mutants have an overall desirable improved fidelity index factor of at least 2, more than 10, at least 50 or more than 500 and to select enzymes as preferred high fidelity mutants.

In an embodiment of the invention, the mutant restriction endonucleases were screened for activity in normal buffer conditions (no more than 5% glycerol) first. For those mutants with at least about 10% of activity of WT restriction endonuclease, activity was also determined in star activity promotion conditions that promoted star activity, for example, high glycerol concentration and optionally high pH. Preferably, the mutant with the least star activity but with acceptable cognate activity in normal buffers is selected. Plasmid can then be extracted and sequenced for the confirmation of the mutant. In some cases, the star activity is not easily measured, even with high glycerol and high pH conditions. Instead, the activity in different buffers is measured and compared, and the one with the highest cleavage activity ratio in NEB4 compared with NEB3 can be tested further for star activity improvement.

5. Saturation Mutagenesis on One Single Residue

As described in the previous section, the first step is to mutate a target amino acid in the restriction endonuclease to Ala. If the results are not satisfactory, saturation mutagenesis is performed. This is preferably performed by one of two methods. One method is to change the intended codon into NNN. After mutagenesis, multiple colonies are assayed under normal conditions and under conditions that promote star activity. Alternatively, a different codon can be selected for mutagenesis of each of the targeted amino acids for example: Ala: GCT; Cys: TGC; Asp: GAC; Glu: GAA; His: CAC; Ile: ATC; Lys: AAA; Leu: CTG; Met: ATG; Asn: AAC; Pro: CCG; Gln: CAG; Arg: CGT; Ser: TCC; Thr: ACC; Val: GTT; Trp: TGG and Tyr: TAC 6. Combination More than one mutation can be introduced into the restriction endonuclease gene if a single mutation does not sufficiently reduce the star activity. Mutation combination and saturation mutagenesis can be performed in any order.

7. Mutant Purification and Assessment of the Improvement

The high fidelity mutants may be purified in a variety of ways including use of different chromatography columns. For normal quality assessment, one FPLC heparin column is enough to eliminate the DNA and non-specific nucleases from the preparation. Multiple columns including ion exchange, hydrophobic, size exclusion and affinity columns can be used for further purification.

Purified high fidelity restriction endonucleases are measured for FI in four NEB buffers and compared with the FIs of the WT restriction endonuclease. The ratio of FI for the high fidelity restriction endonuclease in its optimal buffer to that of WT is the overall improvement factor.

TABLE 3

FI * for exemplified restriction endonucleases

| Enzyme | Diluent (NEB) | Substrate * | Temp ° C. | FI-1 ** | FI-2 ** | FI-3 ** | FI-4 ** |
|---|---|---|---|---|---|---|---|
| AgeI-HF | C | pXba | 37 | ≥500 (1) | ≥250 (½) | ≥16 (1/16) | ≥250 (1) |
| AvrII-HF | B | T7 | 37 | 500 (1) | ≥500 (½) | ≥16 (1/64) | ≥1000 (1) |
| BamHI-HF | A | λ | 37 | ≥4000 (1) | ≥4000 (1) | ≥250 (1/16) | ≥4000 (1) |
| BsaI | B | pBC4 | 50 | ≥4000 (1) | ≥8000 (1) | 120 (1) | ≥8000 (1) |
| BsmBI | B | λ | 55 | 2 (1) | ≥500 (1) | ≥64 (⅛) | ≥500 (1) |
| BspQI-HF | A | pUC19 | 50 | ≥1000 (¼) | ≥1000 (¼) | ≥64 (1/64) | ≥4000 (1) |
| BstXI-HF | A | λ | 55 | ≥120 (½) | ≥250 (1) | ≥16 (1/16) | ≥250 (1) |
| EagI-HF | C | pXba | 37 | 250 (½) | 250 (1) | 250 (½) | 500 (1) |
| EcoRI-HF | C | λ | 37 | 2000 (⅛) | 4000 (¼) | 250 (1/250) | 16000 (1) |
| EcoRV-HF | A | pXba | 37 | ≥16000 (¼) | ≥64000 (1) | ≥32000 (½) | ≥64000 (1) |
| HindIII-HF | B | λ | 37 | ≥16000 (¼) | ≥64000 (1) | ≥16000 (¼) | ≥32000 (½) |
| HpaI-HF | A | λ | 37 | ≥32 (1/32) | ≥2000 (1) | 2 (⅛) | ≥2000 (½) |
| KpnI-HF | A | pXba | 37 | ≥4000 (1) | ≥1000 (¼) | ≥64 (1/64) | ≥4000 (1) |
| MfeI-HF | A | λ | 37 | ≥1000 (1) | ≥250 (¼) | ≥16 (1/64) | ≥500 (½) |
| NcoI-HF | A | λ | 37 | ≥4000 (¼) | ≥4000 (¼) | ≥1000 (1/16) | ≥64000 (1) |
| NheI-HF | C | pXba | 37 | ≥128000 (1) | ≥4000 (1/32) | ≥32 (1/2000) | ≥32000 (½) |
| NotI-HF | C | pXba | 37 | ≥8000 (1/16) | ≥128000 (1) | ≥4000 (1/64) | ≥64000 (½) |
| PciI-HF | A | pXba | 37 | NC | ≥2000 (1) | ≥2000 (1) | ≥1000 (1) |
| PstI-HF | C | λ | 37 | 1000 (¼) | 4000 (½) | 4000 (¼) | 4000 (1) |
| PvuII-HF | A | pBR322 | 37 | ≥250 (1/120) | ≥2000 (1) | ≥250 (1/120) | 500 (1) |
| SacI-HF | A | pXba | 37 | ≥32000 (1) | ≥16000 (¼) | ≥500 (1/64) | ≥32000 (1) |
| SalI-HF | A | λ (H3) | 37 | ≥8000 (⅛) | ≥64000 (1) | ≥4000 (1/16) | ≥32000 (½) |
| SbfI-HF | C | λ | 37 | 1000 (1) | 120 (½) | 8 (1/32) | 250 (1) |
| ScaI-HF | A | λ | 37 | 4000 (⅛) | 1000 (1) | 2000 (1/32) | 1000 (1) |
| SphI-HF | B | λ | 37 | 4000 (⅛) | 2000 (1/16) | 250 (1/250) | 8000 (1) |
| SspI-HF | C | λ | 37 | ≥4000 (½) | 120 (½) | ≥32 (1/128) | 500 (1) |

* The FI is a ratio of the highest concentration that does not show star activity to the lowest concentration that completes digestion of the substrate.

** The number in parenthesis is a value for relative cleavage activity of the mutant restriction endonuclease in a specified buffer in a set of buffers compared with the greatest cleavage activity of the same mutant restriction endonuclease in any of the buffers in the set of buffers.

TABLE 4

Mutations providing restriction endonucleases with high fidelity

| Restriction Endonuclease | Examples of mutants with overall improved FI factor ≥ 2 |
|---|---|
| AgeI | R139A; S201A* |
| AvrII | Y104F; M29A; E96A; K106A; S127A; F142A |
| BamHI | E163A/E167T; K30A; E86A; E86P; K87A; K87E; K87V; K87N; P144A; Y165F; E167A; E167R; E167K; E167L; E167I K30A/E86A; E86A/K106A; K30A/E86A/K106A; K30A/K87A; E86P/K87E; E86A/Y165F; K30A/E167A; E163S/E170T/P173A; E163S/E170T/P173A; E86P/K87T/K88N/E163S/E170T/P173A; E86P/K87R/K88G/E163S/E170T/P173A; E86P/K87P/K88R/ E163S/E170T/P173A/E211K; E86P/K87T/K88R/ E163S/E170T/P173A/N158S; E86P/K87S/K88P/ E163S/E170T/P173A; E86P/K87G/K88S/E163S/E170T/P173A; E86P/K87R/K88Q/E163S/E170T/P173A; E86P/K87W/K88V; E86P/P173A |
| BsaI | Y231F |
| BsmBI | N185Y/R232A; H230A; D231A; R232A; |
| BspQI | K279P/R388F; K279A; K279F; K279P; K279Y; K279E; K279D R388A; R388F; R388Y; R388L; K279P/R388F; K279A/R388A; D244A |
| BstXI | N65A; Y57F; E75A; N76A; K199A; |
| EagI | H43A |
| EcoRI | K62A; K62S; K62L; R9A; K15A; R123A; K130A; R131A; R183A; S2Y; D135A; R187A; K62E |
| EcoRV | D19A; E27A; D19A/E27A |
| HindIII | S188P/E190A; K198A |
| HpaI | Y29F; E56A |
| KpnI | D148E; D16N/R119A/D148E; D2A/D16N/D148E; D16N/E134A/D148E; D16N/E132A/D148E |
| MfeI | Y173F; Q13A/F35Y |
| NcoI | D56A; H143A; E166A; R212A; D268A; A2T/R31A |
| NheI | E77A |
| NotI | K176A; R177A; R253A; K150A |
| PciI | E78A/S133A |
| PstI | E204G; K228A; K228A/A289V; D91A |
| PvuII | T46A; T46H; T46K; T46Y; T46G |
| SacI | Q117H/R154A/L284P; Q117H/R200A |
| SalI | R82A; K93A; K101A; R107A |
| SapI | K273P; R380A; K273P/R380A |
| SbfI | K251A |
| ScaI | R18A; R112A; E119A; H193A; S201F; H193A/S201F |
| SphI | D91A; D139A; D164A; K100A |
| SspI | H65A; K74A; E78A; E85A; E89A; K109A; E118A; R177A; K197A; Y98F |

The mutations for each enzyme are separated by a semicolon.

All references cited above and below, as well as U.S. Ser. No. 12/172,963 filed Jul. 14, 2008 and U.S. provisional application Ser. No. 60/959,203, are incorporated by reference.

EXAMPLES

Where amino acids are referred to by a single letter code, this is intended to be standard nomenclature. The key to the code is provided for example in the NEB catalog 2007/2008 on page 280.

Plasmids used for cloning and as substrates have sequences as follows:

pLaczz2 (SEQ ID NO:102), pSyx20-lacIq (SEQ ID NO:105), pBC4 (SEQ ID NO:103), pXba (SEQ ID. NO:104) and pAGR3 (SEQ ID NO:106). pACYC is described in GenBank XO 6403, T7 in GenBank NC001604, pUC18 in GenBank L09136, and pRRS in Skoglund et al. *Gene,* 88:1-5 (1990. pSX33 was constructed by inserting lacI gene into pLG339 at EcoRI site. pLG339 is described in Stoker, et al. *Gene* 19, 335-341 (1982).

All buffers identified as NEB buffers used herein are obtainable from New England Biolabs, Inc. (NEB), Ipswich, Mass.

Example 1

Engineering of High Fidelity NcoI

1. Expression of NcoI

Expression of NcoI was achieved in *E. coli* (pSYX20-NcoIM, pRRS-NcoIR). pRRS is a pUC19 derivative plasmid, and pSYX20 is a compatible low copy number plasmid with pRRS vector. The cells were grown at 30° C. overnight in the LB with Amp and Kanamycin (Kan).

2. Mutagenesis of NcoI

All 66 charged residues in NcoI were mutated to Ala. These residues were: 7, 8, 19, 22, 27, 30, 31, 32, 33, 37, 39, 42, 46, 55, 56, 61, 62, 64, 68, 69, 75, 84, 88, 89, 92, 93, 95, 97, 100, 116, 136, 144, 146, 162, 166, 170, 178, 183, 185, 187, 188, 189, 196, 199, 202, 204, 209, 211, 212, 213, 216, 219, 227, 229, 237, 241, 244, 250, 251, 257, 259, 261, 268, 279, 282, 285.

The numbers above correspond to amino acid positions in the NcoI protein sequence (SEQ ID NO:88).

The methods were the same as disclosed in the examples of the parent application, U.S. Ser. No. 12/172,963 filed Jul. 14, 2008, using inverse PCR followed by DpnI digestion. The treated product was then transformed into *E. coli* (pSYX20-NcoIM).

3. Selection of NcoI-HF

The selection of NcoI-HF was similar to that of PstI-HF as disclosed in the examples of the parent application, U.S. Ser. No. 12/172,963 filed Jul. 14, 2008. The activity was assayed as described above using lambda DNA as substrate with 5% glycerol. Star activity was determined using pBR322 or lambda in 19% DMSO. The following mutations were found to improve star activity: A2T/R31A, D56A, H143A, E166A, R212A and D268A. Among these mutants, NcoI(A2T/R31A) was selected as the NcoI-HF.

4. Comparison of NcoI-HF and WT NcoI

The FIs of NcoI-HF and WT NcoI were determined separately on lambda DNA in NEB1-4 buffers. The comparison is shown in FIG. 14, and the results listed in Table 13 (below).

TABLE 13

Comparison of NcoI-HF with WT NcoI

| Buffer | NcoI-HF | | WT NcoI | | Improvement Factor |
|---|---|---|---|---|---|
| | Activity | Fidelity Index | Activity | Fidelity Index | |
| NEB1 | 25% | ≥4000 | 100% | 120 | ≥32 |
| NEB2 | 25% | ≥4000 | 100% | 32 | ≥125 |

TABLE 13-continued

Comparison of NcoI-HF with WT NcoI

| Buffer | NcoI-HF | | WT NcoI | | Improvement Factor |
|---|---|---|---|---|---|
| | Activity | Fidelity Index | Activity | Fidelity Index | |
| NEB3 | 6.3% | ≥1000 | 25% | 120 | ≥8 |
| NEB4 | 100% | ≥16000 | 100% | 32 | ≥500 |

NcoI-HF showed the greatest reduction in star activity in NEB4, in which the preferred FI was 16000; WT NcoI performed best in NEB1, NEB2 and NEB4, in which the preferred FI was 120. The overall FI improvement factor was ≥16000/120=125.

What is claimed is:

1. A composition comprising a variant NcoI restriction endonuclease having reduced star activity, wherein the variant NcoI restriction endonuclease comprises an amino acid sequence that differs from the amino acid sequence of the parent NcoI restriction endonuclease by amino acid substitutions at positions corresponding to positions 2 and 31 in SEQ ID NO:88.

2. The composition according to claim 1, wherein the substitutions are A2T and R31A.

3. A composition comprising a variant NcoI restriction endonuclease having reduced star activity, wherein the variant NcoI restriction endonuclease comprises an amino acid sequence that differs from the amino acid sequence of the parent NcoI restriction endonuclease by a substitution at an amino acid position corresponding to position 56 in SEQ ID NO:88.

4. The composition according to claim 3, wherein the substitution is D56A.

5. A composition comprising a variant NcoI restriction endonuclease having reduced star activity, wherein the variant NcoI restriction endonuclease comprises an amino acid sequence that differs from the amino acid sequence of the parent NcoI restriction endonuclease by a substitution at an amino acid position corresponding to position 143 in SEQ ID NO:88.

6. The composition according to claim 5, wherein the substitution is H143A.

7. A composition comprising a variant NcoI restriction endonuclease having reduced star activity, wherein the variant NcoI restriction endonuclease comprises an amino acid sequence that differs from the amino acid sequence of the parent NcoI restriction endonuclease by a substitution at an amino acid position corresponding to position 166 in SEQ ID NO:88.

8. The composition according to claim 7, wherein the substitution is E166A.

9. A composition comprising a variant NcoI restriction endonuclease having reduced star activity, wherein the variant NcoI restriction endonuclease comprises an amino acid sequence that differs from the amino acid sequence of the parent NcoI restriction endonuclease by a substitution at an amino acid position corresponding to position 212 in SEQ ID NO:88.

10. The composition according to claim 9, wherein the substitution is R212A.

11. A composition comprising a variant NcoI restriction endonuclease having reduced star activity, wherein the variant NcoI restriction endonuclease comprises an amino acid sequence that differs from the amino acid sequence of the parent NcoI restriction endonuclease by a substitution at an amino acid position corresponding to position 268 in SEQ ID NO:88.

12. The composition according to claim 11, wherein the substitution is D268A.

* * * * *

SEQUENCE LISTING

```
<160> NUMBER OF SEQ ID NOS: 106

<210> SEQ ID NO 1
<211> LENGTH: 1089
<212> TYPE: DNA
<213> ORGANISM: Micrococcus luteus

<400> SEQUENCE: 1
atgatcaagt acttgggtag caagcggacg ctcgtgcccg tcctcggtga catcgcttcg        60
gcctctgaag caacagaggc ggttgacctg ttcactggca cgacgcgtgt ggcgcaagag       120
ttcaagcgtc gcgggcttcg agttcttgct aacgacatag cgacgtactc cgaggtttta       180
gcccagtgct atatcgccac caacggccag gaagttgacc gccgtgcgct cgaggccgct       240
ctggcggagc tgaacgcctt gcccggcgaa cctggatact tcacggaaac cttctgtgag       300
gcttctcgct acttccagcc caagaacggg gctcgggtgg atgcaatcag gaatgcgatc       360
gacgaccggt acgcggactc atggatgcga ccgatcctcc tcacgagctt gatgcttgcg       420
gccgaccgcg tcgactccac taccggagtg cagatggctt acctgaagca gtgggccgcg       480
cgtgcgcaca atgatctaga gttgcggctt ccagacctaa tcgaggtga cggtgacgct       540 gctcgtgagg atgcggtgac tctcgcacaa gagctgcctc gcgtccagct gatgtacctt       600
gatcctccct ataaccagca caggtacttc accaactacc atatttggga gccctgatt       660 cgttgggatg cccctgagag ttatgggatc gcctgtaagc gcattgactc tcgagatgat       720
gccaccaaga gcccctataa tatgaagcgg cgaatgcccg acgagatgcg tcgcctgctg       780
atgaccatca aggcggacct cgcggttgta tcttacaaca atgagtcgtg gattgatccg       840
gagacgatga tgtcgaccct gcgcgatgcg ggatatgagg acgtgcgtct gctcgctttc       900
gactataagc gctacgttgg ggctcaaatc gggatctaca atccctccgg ggaaaaggtc       960
ggtcgtgtga gtcacctccg aaacatcgag tatctctttc ttgcgggacc aacggagcgc      1020
gttgaggtgt gcgccgcgag tgttgaacac cgagcactac ccaaggaacc ggaactcacc      1080
gcgttctag                                                             1089
```

```
<210> SEQ ID NO 2
<211> LENGTH: 362
<212> TYPE: PRT
<213> ORGANISM: Micrococcus luteus

<400> SEQUENCE: 2

Met Ile Lys Tyr Leu Gly Ser Lys Arg Thr Leu Val Pro Val Leu Gly
1               5                   10                  15

Asp Ile Ala Ser Ala Ser Glu Ala Thr Glu Ala Val Asp Leu Phe Thr
            20                  25                  30

Gly Thr Thr Arg Val Ala Gln Glu Phe Lys Arg Arg Gly Leu Arg Val
        35                  40                  45

Leu Ala Asn Asp Ile Ala Thr Tyr Ser Glu Val Leu Ala Gln Cys Tyr
50                  55                  60

Ile Ala Thr Asn Gly Gln Glu Val Asp Arg Arg Ala Leu Glu Ala Ala
65                  70                  75                  80

Leu Ala Glu Leu Asn Ala Leu Pro Gly Glu Pro Gly Tyr Phe Thr Glu
                85                  90                  95

Thr Phe Cys Glu Ala Ser Arg Tyr Phe Gln Pro Lys Asn Gly Ala Arg
            100                 105                 110

Val Asp Ala Ile Arg Asn Ala Ile Asp Asp Arg Tyr Ala Asp Ser Trp
        115                 120                 125

Met Arg Pro Ile Leu Leu Thr Ser Leu Met Leu Ala Ala Asp Arg Val
130                 135                 140

Asp Ser Thr Thr Gly Val Gln Met Ala Tyr Leu Lys Gln Trp Ala Ala
145                 150                 155                 160

Arg Ala His Asn Asp Leu Glu Leu Arg Leu Pro Asp Leu Ile Ala Gly
                165                 170                 175

Asp Gly Asp Ala Ala Arg Glu Asp Ala Val Thr Leu Ala Gln Glu Leu
            180                 185                 190

Pro Arg Val Gln Leu Met Tyr Leu Asp Pro Pro Tyr Asn Gln His Arg
        195                 200                 205

Tyr Phe Thr Asn Tyr His Ile Trp Glu Thr Leu Ile Arg Trp Asp Ala
210                 215                 220

Pro Glu Ser Tyr Gly Ile Ala Cys Lys Arg Ile Asp Ser Arg Asp Asp
225                 230                 235                 240

Ala Thr Lys Ser Pro Tyr Asn Met Lys Arg Arg Met Pro Asp Glu Met
                245                 250                 255

Arg Arg Leu Leu Met Thr Ile Lys Ala Asp Leu Ala Val Val Ser Tyr
            260                 265                 270

Asn Asn Glu Ser Trp Ile Asp Pro Glu Thr Met Met Ser Thr Leu Arg
        275                 280                 285

Asp Ala Gly Tyr Glu Asp Val Arg Leu Leu Ala Phe Asp Tyr Lys Arg
290                 295                 300

Tyr Val Gly Ala Gln Ile Gly Ile Tyr Asn Pro Ser Gly Glu Lys Val
305                 310                 315                 320

Gly Arg Val Ser His Leu Arg Asn Ile Glu Tyr Leu Phe Leu Ala Gly
                325                 330                 335

Pro Thr Glu Arg Val Glu Val Cys Ala Ala Ser Val Glu His Arg Ala
            340                 345                 350

Leu Pro Lys Glu Pro Glu Leu Thr Ala Phe
        355                 360

<210> SEQ ID NO 3
<211> LENGTH: 1146
```

<212> TYPE: DNA
<213> ORGANISM: Helicobacter pylori J166

<400> SEQUENCE: 3

```
ttggagaatt ttttgaataa tttagatatt aaaaccttag ggcaggtttt caccoctaaa      60
aagatagtgg atttcatgct cactctcaag cacaatcatg ggagtgtttt agagccaagc     120
gcgggcgatg ggagttttt aaagcgctta aaaaggctg tagggattga atcgatcct       180
aaaatctgcc ctaaaaatgc cctttgcatg gactttttg actacccttt agaaaatcaa      240
tttgacacga ttattggcaa tccgccctat gtcaagcaca aggatattgc gccaagcacg     300
aaagaaaaac tccattacag ccttttttgat gaaggagta atctatactt gttttcata      360
gaaaaagcga tcaagcattt aaagcctaaa ggcgaattga ttttcatcac cccaagggat     420
tttttaaaat ccacttctag cgtgaaatta acgaatgga tttacaaaga aggcacgata      480
acgcattttt ttgaattagg cgatcaaaag attttcccaa acgccatgcc taattgcgtg     540
attttttcgtt tttgtaaagg tgatttcagt agaatcacca acgatggttt gcaatttgtg    600
tgcaaaaaag gcattttgta tttcctcaac caatcttaca cgcaaaaatt aagcgaggtt     660
tttaaggtta aggtgggggc agtgagcggg tgcgataaga ttttttaaaaa tgaaacatac    720
gggaattag aatttgtcac ctcaatcacc aaaagaacca atgttttaga aaaaatggtt     780
tttgtcaata aacctaatga ttatttactc cagcataaag acagcttgat gcaaagaaag    840
attaaaaat tcaatgaaag taattggttt gaatggggga ggatgcatca catatcccct    900
aaaaaacgca tttatgttaa cgccaaaacg cgccaaaaaa acccttttt catccaccaa    960
tgccctaatt atgacggctc tatttttagcg ctattccctt ataaccaaaa tttggattta   1020
caaaaccttct gcgataaact caacgctatc aactggcaag aattaggctt tgtgtgcggc   1080
gggcgttttt tgttttcgca gcgctcttta gaaaacgccc ttttgcctaa agactttta    1140
aattag                                                               1146
```

<210> SEQ ID NO 4
<211> LENGTH: 609
<212> TYPE: DNA
<213> ORGANISM: Mycoplasma fermentans

<400> SEQUENCE: 4

```
atgggtaaat ctgaattaag tgaagatta aattggcaag cattggctgg attaaaagct      60
agtggtgctg aacaaaactt atataacgtg tttaacgctg ttttttgaagg aactaaatac    120
gttttatacg agaagccaaa gcaccttaaa aatctatacg ctcaagtagt cttacctgat   180
gatgttatta agaaattttt taatcctta attgatttat caactactca atgggggtgtt   240
tctccagatt tcgcaataga aaatacagaa acgcataaaa ttcttttgg tgaaattaaa    300
agacaagatg gatgggtaga aggtaaagat cctagtgctg cagggggtaa tgcacatgag  360
agatcttgta aattatttac tcctggatta ttaaaagctt atagaacaat ggtggaatt    420
aacgatgaag agatattgcc attctgggtt gtattcgaag gtgatataac acgagatccc    480
aaaagagtaa gagaaattac tttctggtat gaccactatc aagataatta tttcatgtgg   540
cgaccaaatg aatcaggcga aaattagtt caacacttca atgaaaaatt aaaaaaatat   600
ttagattaa                                                              609
```

<210> SEQ ID NO 5
<211> LENGTH: 202
<212> TYPE: PRT

<213> ORGANISM: Mycoplasma fermentans

<400> SEQUENCE: 5

```
Met Gly Lys Ser Glu Leu Ser Gly Arg Leu Asn Trp Gln Ala Leu Ala
1               5                   10                  15

Gly Leu Lys Ala Ser Gly Ala Glu Gln Asn Leu Tyr Asn Val Phe Asn
            20                  25                  30

Ala Val Phe Glu Gly Thr Lys Tyr Val Leu Tyr Glu Lys Pro Lys His
        35                  40                  45

Leu Lys Asn Leu Tyr Ala Gln Val Val Leu Pro Asp Asp Val Ile Lys
    50                  55                  60

Glu Ile Phe Asn Pro Leu Ile Asp Leu Ser Thr Thr Gln Trp Gly Val
65                  70                  75                  80

Ser Pro Asp Phe Ala Ile Glu Asn Thr Glu Thr His Lys Ile Leu Phe
                85                  90                  95

Gly Glu Ile Lys Arg Gln Asp Gly Trp Val Glu Gly Lys Asp Pro Ser
            100                 105                 110

Ala Gly Arg Gly Asn Ala His Glu Arg Ser Cys Lys Leu Phe Thr Pro
        115                 120                 125

Gly Leu Leu Lys Ala Tyr Arg Thr Ile Gly Ile Asn Asp Glu Glu
    130                 135                 140

Ile Leu Pro Phe Trp Val Val Phe Glu Gly Asp Ile Thr Arg Asp Pro
145                 150                 155                 160

Lys Arg Val Arg Glu Ile Thr Phe Trp Tyr Asp His Tyr Gln Asp Asn
                165                 170                 175

Tyr Phe Met Trp Arg Pro Asn Glu Ser Gly Glu Lys Leu Val Gln His
            180                 185                 190

Phe Asn Glu Lys Leu Lys Lys Tyr Leu Asp
        195                 200
```

<210> SEQ ID NO 6
<211> LENGTH: 1152
<212> TYPE: DNA
<213> ORGANISM: Bacillus stearothermophilus X1

<400> SEQUENCE: 6

```
atggctatta cattatgtga cataaatggt tgtagacttg agagaggaca tactggtaaa      60
cataataaat ttcctgaatt tgtatggact tctcaattta taaaaaaga tattgataag     120 gtcaataaag caggatatgc aacaccaaga ggtgggaca aggagccta tcagaaccat      180 gtttacagaa ataataaagt aattattcct tttgaaggt tggaaatgt taatttaaat      240 aactatcaag atggatatgt tattaggtta ttccctaatc agtactttga atcagccggg     300
gtagttaagc cggaattctt acaaccaaat tcatttgtta agttgggga caatgcattt     360 attttatatc gcacacattc atcttttgag gaattacctc tctaccaga ctgggaggtt     420 agacatctaa aaaagaacgg taatatagtt accagaagaa gtaaggacgt aatcgatgct     480
ggacattatg tcttacgatt atcatcaatt agtaacaaaa aagaaagaaa agagggccct     540
cctcaaggta tttttgcacc tgaatatgca aatgcagaga ctaattatct gtcaaaagca     600 ttttagcct ggttaattat taaaactcaa atagtccgt ataatgaaga caattccaa      660 cacttaagag cgatcttaat tagtcataat ctcatcaata tttctcaact tgaagaaaag     720
gctattctaa agaatggtat cacatgctgc cctttatgcg agcaaattat ttttacgaa     780 cagctacacg aaatggtttc ttttgaaggt gcgtctggcc ttgcgaattc acaagaacag     840
```

-continued

```
gttgagggtg caactaggtc aacatcagtt aatttattcc atatggtacc attagtatat    900
gaaaccttgg aacacaaacc tgatcaaata gcatggggcc atgccatttg taatactaga    960
cttggtcaaa gagagtgcct gcctcttagt agactaaaac aagaaggtac gcccgttggt   1020
cttcttgatg aagattcgaa tcttgaagta ttaggatgga ttagtaaaga taagcaattt   1080
attcgtacag aaaatgggga agtttggatt aaaattacag atattgaatt taacgatgac   1140
tttgaagaat aa                                                       1152
```

<210> SEQ ID NO 7
<211> LENGTH: 383
<212> TYPE: PRT
<213> ORGANISM: Bacillus stearothermophilus X1

<400> SEQUENCE: 7

```
Met Ala Ile Thr Leu Cys Asp Ile Asn Gly Cys Arg Leu Glu Arg Gly
1               5                   10                  15

His Thr Gly Lys His Asn Lys Phe Pro Glu Phe Val Trp Thr Ser Gln
            20                  25                  30

Phe Asn Lys Lys Asp Ile Asp Lys Val Asn Lys Ala Gly Tyr Ala Thr
        35                  40                  45

Pro Arg Gly Gly Asp Lys Gly Ala Tyr Gln Asn His Val Tyr Arg Asn
    50                  55                  60

Asn Lys Val Ile Ile Pro Phe Glu Arg Leu Glu Asn Val Asn Leu Asn
65                  70                  75                  80

Asn Tyr Gln Asp Gly Tyr Val Ile Arg Leu Phe Pro Asn Gln Tyr Phe
                85                  90                  95

Glu Ser Ala Gly Val Val Lys Pro Glu Phe Leu Gln Pro Asn Ser Phe
            100                 105                 110

Val Lys Val Gly Asp Asn Ala Phe Ile Leu Tyr Arg Thr His Ser Ser
        115                 120                 125

Phe Glu Glu Leu Pro Pro Leu Pro Asp Trp Glu Val Arg His Leu Lys
    130                 135                 140

Lys Asn Gly Asn Ile Val Thr Arg Arg Ser Lys Asp Val Ile Asp Ala
145                 150                 155                 160

Gly His Tyr Val Leu Arg Leu Ser Ser Ile Ser Asn Lys Lys Glu Arg
                165                 170                 175

Lys Glu Gly Pro Pro Gln Gly Ile Phe Ala Pro Glu Tyr Ala Asn Ala
            180                 185                 190

Glu Thr Asn Tyr Leu Ser Lys Ala Phe Leu Ala Trp Leu Ile Ile Lys
        195                 200                 205

Thr Gln Asn Ser Pro Tyr Asn Glu Glu Gln Phe Gln His Leu Arg Ala
    210                 215                 220

Ile Leu Ile Ser His Asn Leu Ile Asn Ile Ser Gln Leu Glu Glu Lys
225                 230                 235                 240

Ala Ile Leu Lys Asn Gly Ile Thr Cys Cys Pro Leu Cys Glu Gln Ile
                245                 250                 255

Ile Phe Tyr Glu Gln Leu His Glu Met Val Ser Phe Glu Gly Ala Ser
            260                 265                 270

Gly Leu Ala Asn Ser Gln Glu Gln Val Glu Gly Ala Thr Arg Ser Thr
        275                 280                 285

Ser Val Asn Leu Phe His Met Val Pro Leu Val Tyr Glu Thr Leu Glu
    290                 295                 300

His Lys Pro Asp Gln Ile Ala Trp Gly His Ala Ile Cys Asn Thr Arg
305                 310                 315                 320
```

Leu Gly Gln Arg Glu Cys Leu Pro Leu Ser Arg Leu Lys Gln Glu Gly
                325                 330                 335

Thr Pro Val Gly Leu Leu Asp Glu Asp Ser Asn Leu Glu Val Leu Gly
            340                 345                 350

Trp Ile Ser Lys Asp Lys Gln Phe Ile Arg Thr Glu Asn Gly Glu Val
        355                 360                 365

Trp Ile Lys Ile Thr Asp Ile Glu Phe Asn Asp Asp Phe Glu Glu
    370                 375                 380

<210> SEQ ID NO 8
<211> LENGTH: 1536
<212> TYPE: DNA
<213> ORGANISM: Bacillus stearothermophilus X1
<220> FEATURE:
<221> NAME/KEY: misc_feature
<223> OTHER INFORMATION: DNA sequence of M.BstXI

<400> SEQUENCE: 8

| | | | | | |
|---|---|---|---|---|---|
| atgattttg | ctgatattga | atttgaaaaa | gaactttttt | cagctgctaa | taaattaagg | 60 |
| ggaaaaattg | ctccaagtga | gtataagcat | tatgttttgc | ctttgatatt | ccttagatat | 120 |
| ttatctctta | ataccaaca | aagaaggaat | gaaattcaac | aacagataaa | tgattcaagg | 180 |
| gatcacaaga | aaaatcaaga | tgaagtgtta | aagatattgg | aagacaggac | tgaatacacc | 240 |
| aaagtaaatg | ttttctatat | tcctgaaaaa | gctagtggg | aatacttatt | gaaaaattcc | 300 |
| gaaaatgata | aaattaaaga | aatgatagat | tcagctatgg | aaatactgga | aaatgaatat | 360 |
| gacgagttaa | aaggtgtttt | gccaaagata | tataaaaact | caaatatacc | gatgaagtt | 420 |
| attagtgatt | tactaaaact | attttctcaa | gaagtattt | cagcacatga | tggaagaaat | 480 |
| gttgattat | tggggagagt | ttatgaatac | tttataagta | attttgctac | tacagaaggt | 540 |
| actagaggtg | gtgaatattt | tacaccgtct | tcaatcgtaa | aattattggt | agcaatgcta | 600 |
| gagcccatta | aagtacagt | ttatgatccg | gcctgtggga | caggaggaat | gtttattcag | 660 |
| tctaataaat | atagagaaaa | taatcataac | ttgtgttttg | taggccagga | acaaaacgag | 720 |
| cttactatca | aattggctaa | aatgaatgga | attctacatg | gaataaatcc | tgaaattaga | 780 |
| caaggtgatt | cattattaaa | tgaccgttat | ccagaattga | aagctgaaat | tgtaatatct | 840 |
| aatccaccgt | ttaatatgaa | ggattgggga | gctgaacgcc | tgccacttaa | tgataagcga | 900 |
| ttaataggac | cggtaacaaa | cagtaatgca | aattacatgt | ggatacagca | ttttctatac | 960 |
| catttaaaag | atggtggttt | agcaggattt | gttattgcta | atggagcttt | gactagtaat | 1020 |
| ctggctgctg | aaaaaattgt | aaggaaacac | ttaatagaca | atgattatgt | agattgtgtt | 1080 |
| gttcaattac | ctgaaaaaat | gttctttggt | actggcattc | aagtgctttt | agtgttttta | 1140 |
| agtaagaatc | gaaatggaag | taacggccat | gccaaaagag | aaaagaggt | tctatttatt | 1200 |
| gatgcaagcg | ataagggaac | attagtgggt | aaaaagaata | aaatatttt | agatgatgaa | 1260 |
| ataaaagaaa | ttgcagattt | atatcattca | tttaaatttt | taaatgataa | tgattataac | 1320 |
| catagtggtt | tttacaaaaa | ggttaacatt | gaaaaaatcg | tggaaaatga | ttataaatta | 1380 |
| actccaactc | tctatgtagg | tgtaaaggaa | gagactgaaa | tggagaagcc | atttagagaa | 1440 |
| atgataatag | aatataaagc | gatattagag | caacaatttg | aagaatcaaa | caaactacag | 1500 |
| cagaaaatat | taagaatttt | agagggatta | ttatga | | | 1536 |

<210> SEQ ID NO 9
<211> LENGTH: 511

```
<212> TYPE: PRT
<213> ORGANISM: Bacillus stearothermophilus X1
<220> FEATURE:
<221> NAME/KEY: misc_feature
<223> OTHER INFORMATION: protein sequence for M.BstXI

<400> SEQUENCE: 9

Met Ile Phe Ala Asp Ile Glu Phe Glu Lys Glu Leu Phe Ser Ala Ala
 1               5                  10                  15

Asn Lys Leu Arg Gly Lys Ile Ala Pro Ser Glu Tyr Lys His Tyr Val
             20                  25                  30

Leu Pro Leu Ile Phe Leu Arg Tyr Leu Ser Leu Lys Tyr Gln Gln Arg
         35                  40                  45

Arg Asn Glu Ile Gln Gln Gln Ile Asn Asp Ser Arg Asp His Lys Lys
     50                  55                  60

Asn Gln Asp Glu Val Leu Lys Ile Leu Glu Asp Arg Thr Glu Tyr Thr
 65                  70                  75                  80

Lys Val Asn Val Phe Tyr Ile Pro Glu Lys Ala Ser Trp Glu Tyr Leu
                 85                  90                  95

Leu Lys Asn Ser Glu Asn Asp Lys Ile Lys Glu Met Ile Asp Ser Ala
             100                 105                 110

Met Glu Ile Leu Glu Asn Glu Tyr Asp Glu Leu Lys Gly Val Leu Pro
         115                 120                 125

Lys Ile Tyr Lys Asn Ser Asn Ile Pro Asn Glu Val Ile Ser Asp Leu
    130                 135                 140

Leu Lys Leu Phe Ser Gln Glu Val Phe Ser Ala His Asp Gly Arg Asn
145                 150                 155                 160

Val Asp Leu Leu Gly Arg Val Tyr Glu Tyr Phe Ile Ser Asn Phe Ala
                165                 170                 175

Thr Thr Glu Gly Thr Arg Gly Gly Glu Tyr Phe Thr Pro Ser Ser Ile
            180                 185                 190

Val Lys Leu Leu Val Ala Met Leu Glu Pro Ile Lys Gly Thr Val Tyr
        195                 200                 205

Asp Pro Ala Cys Gly Thr Gly Gly Met Phe Ile Gln Ser Asn Lys Tyr
    210                 215                 220

Arg Glu Asn Asn His Asn Leu Cys Phe Val Gly Gln Glu Gln Asn Glu
225                 230                 235                 240

Leu Thr Ile Lys Leu Ala Lys Met Asn Gly Ile Leu His Gly Ile Asn
                245                 250                 255

Pro Glu Ile Arg Gln Gly Asp Ser Leu Leu Asn Asp Arg Tyr Pro Glu
            260                 265                 270

Leu Lys Ala Glu Ile Val Ile Ser Asn Pro Pro Phe Asn Met Lys Asp
        275                 280                 285

Trp Gly Ala Glu Arg Leu Pro Leu Asn Asp Lys Arg Leu Ile Gly Pro
    290                 295                 300

Val Thr Asn Ser Asn Ala Asn Tyr Met Trp Ile Gln His Phe Leu Tyr
305                 310                 315                 320

His Leu Lys Asp Gly Gly Leu Ala Gly Phe Val Ile Ala Asn Gly Ala
                325                 330                 335

Leu Thr Ser Asn Leu Ala Ala Glu Lys Ile Val Arg Lys His Leu Ile
            340                 345                 350

Asp Asn Asp Tyr Val Asp Cys Val Val Gln Leu Pro Glu Lys Met Phe
        355                 360                 365

Phe Gly Thr Gly Ile Pro Ser Ala Leu Val Phe Leu Ser Lys Asn Arg
    370                 375                 380
```

```
Asn Gly Ser Asn Gly His Ala Lys Arg Glu Lys Glu Val Leu Phe Ile
385                 390                 395                 400

Asp Ala Ser Asp Lys Gly Thr Leu Val Gly Lys Lys Asn Lys Ile Phe
            405                 410                 415

Leu Asp Asp Glu Ile Lys Glu Ile Ala Asp Leu Tyr His Ser Phe Lys
            420                 425                 430

Phe Leu Asn Asp Asn Asp Tyr Asn His Ser Gly Phe Tyr Lys Lys Val
        435                 440                 445

Asn Ile Glu Lys Ile Val Glu Asn Asp Tyr Lys Leu Thr Pro Thr Leu
    450                 455                 460

Tyr Val Gly Val Lys Glu Thr Glu Met Glu Lys Pro Phe Arg Glu
465                 470                 475                 480

Met Ile Ile Glu Tyr Lys Ala Ile Leu Glu Gln Gln Phe Glu Glu Ser
            485                 490                 495

Asn Lys Leu Gln Gln Lys Ile Leu Lys Asn Leu Glu Gly Leu Leu
        500                 505                 510
```

<210> SEQ ID NO 10
<211> LENGTH: 1179
<212> TYPE: DNA
<213> ORGANISM: Bacillus stearothermophilus X1
<220> FEATURE:
<221> NAME/KEY: misc_feature
<223> OTHER INFORMATION: DNA sequence of S.BstXI

<400> SEQUENCE: 10

```
atgaaaagta ctttgaagga atataaattg ggtgatatta ccgaagtcgt taatggtgcc      60
actccttcaa ctaaaaagcc tgagtactat gaaaatggta caattccatg gattactcct     120
aaagatttat caggctatta ctttaaatat atatctcatg gtgaacgtaa tataacagag     180
cttggtctaa gaaatagttc agctaagttg ttaccaaaag gaactgtatt attttcctca     240
agagccccaa taggatacgt agcaatagct gataattggt taactacgaa ccagggattt     300
aaaagtttta tatgtaatga ggagattatt tacaatgaat cctttattta ttttcttatt     360
gctaaaaggg attttattga acatttgcga atgggagta cgtttaaaga ctttcatca      420
acttctgcaa gaatataccc aatcaatctt cctagtttag aagagcaaaa aagagattgtg    480
acaatttag gggattgga tagaaagata gaattaaatt ataaaattat tgaaagctta      540
gaaaaaatag cagaagaac atataaatat tggtttgtcg atgaattaaa tcaagatgaa      600
cagcacatcc gtaatggatg ggaaactgct aaaattggcg atgtggtgga acttttggga     660
gggggaaccc ctaaaacttc ggaaagtaag tattgggaag atggagatat taattggttt    720
actccttcag atttaacaaa aactagacag ctttttgtac gtgattctca aagaaaaata     780
acaattgatg gacttaataa cagtgcagcg aaattaattc cccttattc cttgttaatg      840
tcaagtagag ctacaattgg cgagttggca attaatcaag aatctgctac tacaaatcaa     900
gggtttattg tattaatacc aaatgaaaaa atttctattt accaattata cttttgggct    960
aaacttaata agagcaaaat tatttcaatg gcaaatggta gtacttttaa agaaattagt    1020
aagcgggatt ttaatctttt ggagataata ttaccaaaaa atatagacac ttttaattca    1080
attatgcaag attatttttag gaaaattgag gagttaattg atgaaataaa aatcttaaaa    1140
accgcaagag ataatttaat tccaaaactt ataaaatga                           1179
```

<210> SEQ ID NO 11
<211> LENGTH: 392

<212> TYPE: PRT
<213> ORGANISM: Bacillus stearothermophilus X1
<220> FEATURE:
<221> NAME/KEY: misc_feature
<223> OTHER INFORMATION: protein sequence for S.BstXI

<400> SEQUENCE: 11

```
Met Lys Ser Thr Leu Lys Glu Tyr Lys Leu Gly Asp Ile Thr Glu Val
1               5                   10                  15

Val Asn Gly Ala Thr Pro Ser Thr Lys Lys Pro Glu Tyr Tyr Glu Asn
            20                  25                  30

Gly Thr Ile Pro Trp Ile Thr Pro Lys Asp Leu Ser Gly Tyr Tyr Phe
                35                  40                  45

Lys Tyr Ile Ser His Gly Glu Arg Asn Ile Thr Glu Leu Gly Leu Arg
        50                  55                  60

Asn Ser Ser Ala Lys Leu Leu Pro Lys Gly Thr Val Leu Phe Ser Ser
65                  70                  75                  80

Arg Ala Pro Ile Gly Tyr Val Ala Ile Ala Asp Asn Trp Leu Thr Thr
                85                  90                  95

Asn Gln Gly Phe Lys Ser Phe Ile Cys Asn Glu Glu Ile Ile Tyr Asn
            100                 105                 110

Glu Tyr Leu Tyr Tyr Phe Leu Ile Ala Lys Arg Asp Phe Ile Glu Thr
        115                 120                 125

Phe Ala Asn Gly Ser Thr Phe Lys Glu Leu Ser Ser Thr Ser Ala Lys
130                 135                 140

Asn Ile Pro Ile Asn Leu Pro Ser Leu Glu Glu Gln Lys Lys Ile Val
145                 150                 155                 160

Thr Ile Leu Gly Asp Leu Asp Arg Lys Ile Glu Leu Asn Tyr Lys Ile
                165                 170                 175

Ile Glu Ser Leu Glu Lys Ile Ala Glu Arg Thr Tyr Lys Tyr Trp Phe
            180                 185                 190

Val Asp Glu Leu Asn Gln Asp Glu Gln His Ile Arg Asn Gly Trp Glu
        195                 200                 205

Thr Ala Lys Ile Gly Asp Val Val Glu Leu Leu Gly Gly Gly Thr Pro
210                 215                 220

Lys Thr Ser Glu Ser Lys Tyr Trp Glu Asp Gly Asp Ile Asn Trp Phe
225                 230                 235                 240

Thr Pro Ser Asp Leu Thr Lys Thr Arg Gln Leu Phe Val Arg Asp Ser
                245                 250                 255

Gln Arg Lys Ile Thr Ile Asp Gly Leu Asn Asn Ser Ala Ala Lys Leu
            260                 265                 270

Ile Pro Pro Tyr Ser Leu Leu Met Ser Ser Arg Ala Thr Ile Gly Glu
        275                 280                 285

Leu Ala Ile Asn Gln Glu Ser Ala Thr Thr Asn Gln Gly Phe Ile Val
290                 295                 300

Leu Ile Pro Asn Glu Lys Ile Ser Ile Tyr Gln Leu Tyr Phe Trp Ala
305                 310                 315                 320

Lys Leu Asn Lys Ser Lys Ile Ile Ser Met Ala Asn Gly Ser Thr Phe
                325                 330                 335

Lys Glu Ile Ser Lys Arg Asp Phe Lys Ser Leu Glu Ile Ile Leu Pro
            340                 345                 350

Lys Asn Ile Asp Thr Phe Asn Ser Ile Met Gln Asp Tyr Phe Arg Lys
        355                 360                 365

Ile Glu Glu Leu Ile Asp Glu Ile Lys Ile Leu Lys Thr Ala Arg Asp
370                 375                 380
```

```
Asn Leu Ile Pro Lys Leu Ile Lys
385                 390
```

<210> SEQ ID NO 12
<211> LENGTH: 770
<212> TYPE: DNA
<213> ORGANISM: planococcus citreus SE-F45

<400> SEQUENCE: 12

```
atgaaacagt tgcagatcc tttgaaaga agattccttg atgcaattga acatcatctt      60
gatggaattt ctgagaaaat aaaaaaagac tttacacaca aaaactttt aaaagaattg    120
aatggcctta aaggtgataa agtctatcat gacttaggct tgataccgc tgaatatact   180
ctggtacgtc ttataggaag aatgagcata agcgttggga aaggctggg ggagatatac   240
gataaagtcc ctcgttatgt tgctgccgcg cgatttggtc ttcaaccaaa tcaaattgca   300
gaagtatttg atggtcttga gttagatata gctttgcgca atagcctttt gtcagatgat   360
gataaaattc acataaaaaa aataactgaa agatgtcag gcgaaacata ctcgggaatc   420
ggaatcgaaa ttcgttataa ctttaatcca aatgacagtt cccgtttaag aaaagacgtc   480
gatgtagctt ctaaattgtc ggccgcgggg ttatttcctg tttatttaat atttagctct   540
ctcagtccta ggaatgatgc aatagcccgt cttaaaagag ggggatggag ctttaaacag   600
gggcaggaag ccttagactt ccttaccgaa cttttaggag tggatattgg gtctgtttta   660
tctgacccaa taatagccgc agaaactagg gagaaaacat caaaaattat gaagtctata   720
tttgaatcag aggcattcca atctgttata ccgggagagt ggagtaaact                770
```

<210> SEQ ID NO 13
<211> LENGTH: 257
<212> TYPE: PRT
<213> ORGANISM: planococcus citreus SE-F45

<400> SEQUENCE: 13

```
Met Lys Gln Phe Ala Asp Pro Phe Glu Arg Arg Phe Leu Asp Ala Ile
1               5                   10                  15

Glu His His Leu Asp Gly Ile Ser Glu Lys Ile Lys Lys Asp Phe Thr
            20                  25                  30

His Lys Asn Phe Leu Lys Glu Leu Asn Gly Leu Lys Gly Asp Lys Val
        35                  40                  45

Tyr His Asp Leu Gly Phe Asp Thr Ala Glu Tyr Thr Leu Val Arg Leu
    50                  55                  60

Ile Gly Arg Met Ser Ile Ser Val Gly Arg Arg Leu Gly Glu Ile Tyr
65                  70                  75                  80

Asp Lys Val Pro Arg Tyr Val Ala Ala Arg Phe Gly Leu Gln Pro
                85                  90                  95

Asn Gln Ile Ala Glu Val Phe Asp Gly Leu Glu Leu Asp Ile Ala Leu
            100                 105                 110

Arg Asn Ser Leu Leu Ser Asp Asp Lys Ile His Ile Lys Lys Ile
        115                 120                 125

Thr Glu Lys Met Ser Gly Glu Thr Tyr Ser Gly Ile Gly Ile Glu Ile
    130                 135                 140

Arg Tyr Asn Phe Asn Pro Asn Asp Ser Ser Arg Leu Arg Lys Asp Val
145                 150                 155                 160

Asp Val Ala Ser Lys Leu Ser Ala Gly Leu Phe Pro Val Tyr Leu
                165                 170                 175
```

```
Ile Phe Ser Ser Leu Ser Pro Arg Asn Asp Ala Ile Ala Arg Leu Lys
            180                 185                 190
Arg Gly Gly Trp Ser Phe Lys Gln Gly Gln Glu Ala Leu Asp Phe Leu
        195                 200                 205
Thr Glu Leu Leu Gly Val Asp Ile Gly Ser Val Leu Ser Asp Pro Ile
    210                 215                 220
Ile Ala Ala Glu Thr Arg Glu Lys Thr Ser Lys Ile Met Lys Ser Ile
225                 230                 235                 240
Phe Glu Ser Glu Ala Phe Gln Ser Val Ile Pro Gly Glu Trp Ser Lys
            245                 250                 255
Leu

<210> SEQ ID NO 14
<211> LENGTH: 1347
<212> TYPE: DNA
<213> ORGANISM: planococcus citreus SE-F45
<220> FEATURE:
<221> NAME/KEY: misc_feature
<223> OTHER INFORMATION: DNA sequence for M.PciI

<400> SEQUENCE: 14
atgacaaatt tttcgcactc agctctaacg agctacgatc ttctcgggca tgaaattgtc      60
caagattctg aagctgttag ctcgggtcca tatctggtca gctatgaccc gatccctgta     120
cgtcggtcta cattcctagc tggactgtca gagaacgttc actcgtggtt tcgtctcaca     180
ccaagtttcg gaccggatct agttcgaaca atcatcaaac agatgaatct gcgccgcac     240 tcacacatcc atgacccttt ctcaggagcc gggactaccg cgattgaggc ttcgttagag     300
ggctatgaag caagctgcgt agaagttaat ccgtttctct acttcgtggg gaaaacatcc     360
atagattggt ctatcaatgc tgatgatgct gcagcgcagc tagaaagcat taaaaataaa     420
tattatagca tgtctgcaac cgctactttg gataacatag ccgacctagg aatagatata     480
ccaaaaatac acaatattca tcggtggtgg agaaacgatg ttcttaaaga tatattagtc     540
ctaaaatctt ctatcagatc ttgcacacaa gataagtatt gttccttttt tgagctagcc     600
ctagctgcag ttctcgttcc agatttgaca aatgtaacgc taggaaaact acaactgcac     660
tttgtaaaca aagacgataa agagataaac gtctggccta catatgaatc tcatgcaaaa     720
aaaatgattc acgacttgtc attaattaat aagcaaaatt tcgaattttt gcccaagatt     780
atttatggtg attcaactca aaaatcaaca tttagcgagg tggcagggat agatgctata     840
ataacatccc ctccgtaccc taataggtac agctatattt ggaatactcg ccctcacctg     900
tacattcttg atatgatttc cgaagcaaaa gaggcttcgc aaatagatcg tagaacgatt     960
ggtggaacat gggggacagc aacttccgaa ttaggaaagg gtatattttc tccaatcaat    1020
gctgtagtca aagacgcgct tgaaggggtt cacgaaagaa tcgccggttc cgatcaactc    1080
atggcaaact atgtaactca ttatttttaat cggctcttttt tacatataga agctataaaa    1140
ccatcactta atccaaaagc aaagcttgct tatgttgttg ggaactcttg gattaagggc    1200
gaatatgtag ccactgacgt aatcttagca aaaattatcg aaggggcttt gccaggctca    1260
tcaattgatg gtcttcatcg tttccgtcgc cggaacagtg aaagaatctc tttgaaaact    1320
atagtttact ccactctccc ggtataa                                        1347

<210> SEQ ID NO 15
<211> LENGTH: 448
<212> TYPE: PRT
<213> ORGANISM: planococcus citreus SE-F45
```

<220> FEATURE:
<221> NAME/KEY: misc_feature
<223> OTHER INFORMATION: Protein sequence for M.PciI

<400> SEQUENCE: 15

Met Thr Asn Phe Ser His Ser Ala Leu Thr Ser Tyr Asp Leu Leu Gly
1               5                   10                  15

His Glu Ile Val Gln Asp Ser Glu Ala Val Ser Ser Gly Pro Tyr Leu
            20                  25                  30

Val Ser Tyr Asp Pro Ile Pro Val Arg Arg Ser Thr Phe Leu Ala Gly
        35                  40                  45

Leu Ser Glu Asn Val His Ser Trp Phe Arg Leu Thr Pro Ser Phe Gly
    50                  55                  60

Pro Asp Leu Val Arg Thr Ile Ile Lys Gln Met Asn Leu Ala Pro His
65                  70                  75                  80

Ser His Ile His Asp Pro Phe Ser Gly Ala Gly Thr Thr Ala Ile Glu
                85                  90                  95

Ala Ser Leu Glu Gly Tyr Glu Ala Ser Cys Val Glu Val Asn Pro Phe
            100                 105                 110

Leu Tyr Phe Val Gly Lys Thr Ser Ile Asp Trp Ser Ile Asn Ala Asp
        115                 120                 125

Asp Ala Ala Gln Leu Glu Ser Ile Lys Asn Lys Tyr Tyr Ser Met
    130                 135                 140

Ser Ala Thr Ala Thr Leu Asp Asn Ile Ala Asp Leu Gly Ile Asp Ile
145                 150                 155                 160

Pro Lys Ile His Asn Ile His Arg Trp Trp Arg Asn Asp Val Leu Lys
                165                 170                 175

Asp Ile Leu Val Leu Lys Ser Ser Ile Arg Ser Cys Thr Gln Asp Lys
            180                 185                 190

Tyr Cys Ser Phe Phe Glu Leu Ala Leu Ala Ala Val Leu Val Pro Asp
        195                 200                 205

Leu Thr Asn Val Thr Leu Gly Lys Leu Gln Leu His Phe Val Asn Lys
    210                 215                 220

Asp Asp Lys Glu Ile Asn Val Trp Pro Thr Tyr Glu Ser His Ala Lys
225                 230                 235                 240

Lys Met Ile His Asp Leu Ser Leu Ile Asn Lys Gln Asn Phe Glu Phe
                245                 250                 255

Leu Pro Lys Ile Ile Tyr Gly Asp Ser Thr Gln Lys Ser Thr Phe Ser
            260                 265                 270

Glu Val Ala Gly Ile Asp Ala Ile Ile Thr Ser Pro Pro Tyr Pro Asn
        275                 280                 285

Arg Tyr Ser Tyr Ile Trp Asn Thr Arg Pro His Leu Tyr Ile Leu Asp
    290                 295                 300

Met Ile Ser Glu Ala Lys Glu Ala Ser Gln Ile Asp Arg Arg Thr Ile
305                 310                 315                 320

Gly Gly Thr Trp Gly Thr Ala Thr Ser Glu Leu Gly Lys Gly Ile Phe
                325                 330                 335

Ser Pro Ile Asn Ala Val Val Lys Asp Ala Leu Glu Gly Val His Glu
            340                 345                 350

Arg Ile Ala Gly Ser Asp Gln Leu Met Ala Asn Tyr Val Thr His Tyr
        355                 360                 365

Phe Asn Arg Leu Phe Leu His Ile Glu Ala Ile Lys Pro Ser Leu Asn
    370                 375                 380

Pro Lys Ala Lys Leu Ala Tyr Val Val Gly Asn Ser Trp Ile Lys Gly

```
385                 390                 395                 400

Glu Tyr Val Ala Thr Asp Val Ile Leu Ala Lys Ile Ile Glu Gly Ala
                405                 410                 415

Leu Pro Gly Ser Ser Ile Asp Gly Leu His Arg Phe Arg Arg Arg Asn
            420                 425                 430

Ser Gly Lys Asn Leu Phe Glu Thr Ile Val Tyr Ser Thr Leu Pro Val
        435                 440                 445

<210> SEQ ID NO 16
<211> LENGTH: 430
<212> TYPE: PRT
<213> ORGANISM: Bacillus sphaericus

<400> SEQUENCE: 16

Met Arg Arg Leu Ala Lys Asn Ser Arg Asn Asp Ser Tyr Leu Ser Asn
1               5                   10                  15

Arg Asp Tyr Gln Glu Ile Val Arg Glu Asn Thr Thr Thr Ile Ser Phe
            20                  25                  30

Pro Leu Lys Glu Lys His Thr Leu Thr Leu Thr Lys Lys Ile Gly Leu
        35                  40                  45

Asn Gln Thr Ala Gly Phe Gly Gly Trp Phe Phe Pro Asp Ser Pro Cys
    50                  55                  60

Leu Leu Thr Val Thr Val Leu Ser Ser Phe Gly Thr Lys Val Thr Ser
65                  70                  75                  80

Lys Thr Phe Ser Leu Ser Lys Asp Trp Asn Arg Val Gly Leu Ala Trp
                85                  90                  95

Ile Asn Glu His Ser Ser Asp Thr Met Ser Ile Val Leu Glu Phe Ser
            100                 105                 110

Asp Val Glu Ile Val His Thr Trp Gly Leu Thr Cys Asp Val Phe Asn
        115                 120                 125

Val His Glu Leu Ile Ile Asp Ala Ile Glu Asp Gln Asn Lys Leu Ile
    130                 135                 140

Asp Val Leu Asn Gln Glu His Leu Ser Pro Glu Thr Tyr Tyr Leu Asn
145                 150                 155                 160

His Asp Ser Asp Thr Asp Leu Ile Glu Asn Leu Glu Ser Thr Glu Glu
                165                 170                 175

Ile Lys Ile Val Asn Gln Ser Gln Lys Gln Ile Ser Leu Lys Lys Cys
            180                 185                 190

Cys Tyr Cys Gln Arg Tyr Met Pro Val Asn Ile Leu Val Arg Ser Asn
        195                 200                 205

Ser Ser Phe His Lys His Lys Ser Lys Lys Thr Gly Phe Gln Asn Glu
    210                 215                 220

Cys Arg Ala Cys Lys Lys Trp Arg Ile Asn Asn Ser Phe Asn Pro Val
225                 230                 235                 240

Arg Thr Lys Asp Gln Leu His Glu Ser Ala Val Ile Thr Arg Glu Lys
                245                 250                 255

Lys Ile Leu Leu Lys Glu Pro Glu Ile Leu Gln Lys Ile Lys Asn Arg
            260                 265                 270

Asn Asn Gly Glu Gly Leu Lys Ser Ile Ile Trp Lys Lys Phe Asp Lys
        275                 280                 285

Lys Cys Phe Asn Cys Glu Lys Glu Leu Thr Ile Glu Glu Val Arg Leu
    290                 295                 300

Asp His Thr Arg Pro Leu Ala Tyr Leu Trp Pro Ile Asp Glu His Ala
305                 310                 315                 320
```

```
Thr Cys Leu Cys Glu Lys Cys Asn Asn Thr Lys His Asp Met Phe Pro
                325                 330                 335

Ile Asp Phe Tyr Gln Gly Asp Glu Asp Lys Leu Arg Arg Leu Ala Arg
            340                 345                 350

Ile Thr Gly Leu Asp Tyr Glu Ser Leu Val Lys Arg Asp Val Asn Glu
        355                 360                 365

Val Glu Leu Ala Arg Ile Ile Asn Asn Ile Glu Asp Phe Ala Thr Asn
    370                 375                 380

Val Glu Ala Arg Thr Phe Arg Ser Ile Arg Asn Lys Val Lys Glu Val
385                 390                 395                 400

Arg Pro Asp Thr Asp Leu Phe Glu Ile Leu Lys Ser Lys Asn Ile Asn
                405                 410                 415

Leu Tyr Asn Glu Leu Gln Tyr Glu Leu Leu Thr Arg Lys Asp
                420                 425                 430

<210> SEQ ID NO 17
<211> LENGTH: 1245
<212> TYPE: DNA
<213> ORGANISM: Enterobacter aerogenes

<400> SEQUENCE: 17
gtgaatcaga aaatgaaaa atcatttatg cgtttgcaat caacctttag cggtggcaaa      60
ggtagtccaa tgcatgattg gtacccatat ttagagggtt attctcccga atttgtgaaa    120
tgcttgattt cacgatttgc tcctaaagcc aaaacaattt tagatccatt ttgtggctct    180
ggaacaacag ccattgtttc cgttttagag ggtttaaata attactattg cgaagtaaac    240
cctttatgcc aatatattat tgaaactaaa ctaatagctt taacattaag cgaagaagaa    300
aaaacaaaat tagtaaatga actttattct atttctaatg aaataactaa tgtactcaaa    360
ccttctgcaa ccgagacaga tctagagaaa tcatttaaat ccgttttttgg taatacgaaa    420 ttttttgagg atcacatatt taaagatata cttagttatc aatgttacat tagctctatc    480
gaagatgaaa atcttaagag acttctgaca atagcaggga ttagatcgtt aatcccttcc    540
tcgttattgg taagacgagg tgatttacga ttcaagacac aaaaagaatt agagaaggc     600 aaccagggct ttcgctttca tgtacaaaaa agcttagaat taattgccag tgatttatta    660
gacattacgg aagtagtggg tttagctacc ttcttatgtg atgatgccaa agaaatatct    720
gggaataacc tgattgatgc tgtaataaca agcccgccat atttaaatgg cacaaattat    780
tttagaaata ctaaaattga actttggttt atagggaaat taaagaccaa atcagatcta    840
agacattata gggatttagc tattaccagt ggtattaacg atgtaactaa aggtaaaagc    900
ttatcttcaa ataatactat tatctcagaa ataccattat tatctgaatg tattaaagaa    960
ctaagcataa aagagtatga tagtcgtatt tcaatgatgg ttgaaaacta cttttgggac   1020
atgttcaaat tcttatcaaa actcccaaaa ttactaacta atgatgcgac tatctgtata   1080
gatttaggtg attctgtttg ttgtaacgtc tacatcccta cacaagatat tttgaaagaa   1140
atgatgtcaa agttaggttt tgaagagaac gaaagggtca ttcttcgtga acgaaaatcc   1200
cgcaatggaa caaagttagt ccagactgtt caggttttta aatga                    1245

<210> SEQ ID NO 18
<211> LENGTH: 1140
<212> TYPE: DNA
<213> ORGANISM: Enterobacter aerogenes

<400> SEQUENCE: 18
```

```
atgaaaaata aatattttag taaaaaatgg gagcaattca agaaagaatt accccatcaa      60
tcaggtgaaa tggtaaagag aaattggggc cataactggc actctatgtg ttcataccaa     120
gggaaactta aaccatcaat agctagatct ttaattgata cattcatgcc atcaagtaag     180
ggacgtatat tagatgtctt ctcaggtgtt ggcaccattc ctttcgaagc aagattactt     240
ggtcatactg catatggatt tgatattagt ccagcagcag ttaatatttc acgcgcaaaa     300
ctagaagtta taagtaaaaa tgaaatccaa gaggtaatta ataaattatc tgattttatt     360
gagcaaaaca aaaattcaat agattataac gaacataatt taataaggtt taatggttca     420
attgaatcct attttcatcc tgaaactttt aaggaaatac tgtgtgctcg taaattcttt     480
ttaataaaag gtgaattaaa tgcatctgaa tcgttagtac agtcatgttt attacatatt     540
ttacatggta atcgtccgta tgcattgagt agaaagtccc atcctattac acctttcgcg     600
cctactggag attttatata cagtaattta gttataaagt taatcaaaaa agttgaaaga     660
gtcttgcaaa attctgatgg tatcccagat actggcagca agtattttta tcaggactct     720
acaaaaagtt ggcctgaaga agtaaataat ttagatgcaa ttataacatc acctccattt     780
tatgatagta cccgttttcta ttcagcaaat tggatgcgat tatggttttc tggttgggaa     840
aaagatgact tccaaacgaa gccaaaagat tttgtggacg aaactcagaa aaaaagcttt     900
gaaatatatg ataatatatt caaacaatct caacaatgct taaaaaaaga tggcgttttt     960
ttaatgcacg ttggcaaaag taaaaaaagt gatatggcag acaaaattgc taaaattggt    1020
agtaattatc ttagccttat agatatattt gacgaaagtg ttgaacattg cgaaagtcac    1080
ggaattaaag acaaaggcac gacaacccat catcagtacc ttgtctttac gaaagattag    1140
```

<210> SEQ ID NO 19
<211> LENGTH: 213
<212> TYPE: PRT
<213> ORGANISM: Bacillus amyloliquefaciens H

<400> SEQUENCE: 19

```
Met Glu Val Glu Lys Glu Phe Ile Thr Asp Glu Ala Lys Glu Leu Leu
1               5                   10                  15

Ser Lys Asp Lys Leu Ile Gln Gln Ala Tyr Asn Glu Val Lys Thr Ser
            20                  25                  30

Ile Cys Ser Pro Ile Trp Pro Ala Thr Ser Lys Thr Phe Thr Ile Asn
        35                  40                  45

Asn Thr Glu Lys Asn Cys Asn Gly Val Val Pro Ile Lys Glu Leu Cys
    50                  55                  60

Tyr Thr Leu Leu Glu Asp Thr Tyr Asn Trp Tyr Arg Glu Lys Pro Leu
65                  70                  75                  80

Asp Ile Leu Lys Leu Glu Lys Lys Gly Gly Pro Ile Asp Val Tyr
                85                  90                  95

Lys Glu Phe Ile Glu Asn Ser Glu Leu Lys Arg Val Gly Met Glu Phe
            100                 105                 110

Glu Thr Gly Asn Ile Ser Ser Ala His Arg Ser Met Asn Lys Leu Leu
        115                 120                 125

Leu Gly Leu Lys His Gly Glu Ile Asp Leu Ala Ile Ile Leu Met Pro
    130                 135                 140

Ile Lys Gln Leu Ala Tyr Tyr Leu Thr Asp Arg Val Thr Asn Phe Glu
145                 150                 155                 160

Glu Leu Glu Pro Tyr Phe Glu Leu Thr Glu Gly Gln Pro Phe Ile Phe
                165                 170                 175
```

```
Ile Gly Phe Asn Ala Glu Ala Tyr Asn Ser Asn Val Pro Leu Ile Pro
                180                 185                 190

Lys Gly Ser Asp Gly Met Ser Lys Arg Ser Ile Lys Lys Trp Lys Asp
        195                 200                 205

Lys Val Glu Asn Lys
    210

<210> SEQ ID NO 20
<211> LENGTH: 194
<212> TYPE: PRT
<213> ORGANISM: Oceanospirillum kriegii

<400> SEQUENCE: 20

Met Lys Ile Lys Arg Ile Glu Val Leu Ile Asn Asn Gly Ser Val Pro
1               5                   10                  15

Gly Ile Pro Met Ile Leu Asn Glu Ile Gln Asp Ala Ile Lys Thr Val
            20                  25                  30

Ser Trp Pro Glu Gly Asn Asn Ser Phe Val Ile Asn Pro Val Arg Lys
        35                  40                  45

Gly Asn Gly Val Lys Pro Ile Lys Asn Ser Cys Met Arg His Leu His
    50                  55                  60

Gln Lys Gly Trp Ala Leu Glu His Pro Val Arg Ile Lys Ala Glu Met
65                  70                  75                  80

Arg Pro Gly Pro Leu Asp Ala Val Lys Met Ile Gly Gly Lys Ala Phe
                85                  90                  95

Ala Leu Glu Trp Glu Thr Gly Asn Ile Ser Ser Ser His Arg Ala Ile
            100                 105                 110

Asn Lys Met Val Met Gly Met Leu Glu Arg Val Ile Ile Gly Gly Val
        115                 120                 125

Leu Ile Leu Pro Ser Arg Asp Met Tyr Asn Tyr Leu Thr Asp Arg Val
    130                 135                 140

Gly Asn Phe Arg Glu Leu Glu Pro Tyr Phe Ser Val Trp Arg Gln Phe
145                 150                 155                 160

Asn Leu Lys Asp Ala Tyr Leu Ala Ile Val Glu Ile Glu His Asp Ser
                165                 170                 175

Val Asp Ala Gln Val Ser Leu Ile Pro Lys Gly Thr Asp Gly Arg Ala
            180                 185                 190

Ile Arg

<210> SEQ ID NO 21
<211> LENGTH: 180
<212> TYPE: PRT
<213> ORGANISM: Bacillus amyloliquefaciens H
<220> FEATURE:
<221> NAME/KEY: MISC_FEATURE
<222> LOCATION: (1)..(180)
<223> OTHER INFORMATION: Residues 1-180 correspond to residues 22-201 of
      the protein sequence of BamHI (seq id no. 19)

<400> SEQUENCE: 21

Ile Gln Gln Ala Tyr Asn Glu Val Lys Thr Ser Ile Cys Ser Pro Ile
1               5                   10                  15

Trp Pro Ala Thr Ser Lys Thr Phe Thr Ile Asn Asn Thr Glu Lys Asn
            20                  25                  30

Cys Asn Gly Val Val Pro Ile Lys Glu Leu Cys Tyr Thr Leu Leu Glu
        35                  40                  45

Asp Thr Tyr Asn Trp Tyr Arg Glu Lys Pro Leu Asp Ile Leu Lys Leu
    50                  55                  60
```

```
Glu Lys Lys Lys Gly Gly Pro Ile Asp Val Tyr Lys Glu Phe Ile Glu
 65                  70                  75                  80

Asn Ser Glu Leu Lys Arg Val Gly Met Glu Phe Glu Thr Gly Asn Ile
                 85                  90                  95

Ser Ser Ala His Arg Ser Met Asn Lys Leu Leu Leu Gly Leu Lys His
            100                 105                 110

Gly Glu Ile Asp Leu Ala Ile Ile Leu Met Pro Ile Lys Gln Leu Ala
            115                 120                 125

Tyr Tyr Leu Thr Asp Arg Val Thr Asn Phe Glu Glu Leu Glu Pro Tyr
130                 135                 140

Phe Glu Leu Thr Glu Gly Gln Pro Phe Ile Phe Ile Gly Phe Asn Ala
145                 150                 155                 160

Glu Ala Tyr Asn Ser Asn Val Pro Leu Ile Pro Lys Gly Ser Asp Gly
                165                 170                 175

Met Ser Lys Arg
            180

<210> SEQ ID NO 22
<211> LENGTH: 177
<212> TYPE: PRT
<213> ORGANISM: Oceanospirillum kriegii
<220> FEATURE:
<221> NAME/KEY: MISC_FEATURE
<222> LOCATION: (1)..(177)
<223> OTHER INFORMATION: Residues 1-177 correspond to residues 18-194
      of the protein sequence of OkrAI (seq id no. 20)

<400> SEQUENCE: 22

Ile Pro Met Ile Leu Asn Glu Ile Gln Asp Ala Ile Lys Thr Val Ser
1               5                   10                  15

Trp Pro Glu Gly Asn Asn Ser Phe Val Ile Asn Pro Val Arg Lys Gly
                20                  25                  30

Asn Gly Val Lys Pro Ile Lys Asn Ser Cys Met Arg His Leu His Gln
            35                  40                  45

Lys Gly Trp Ala Leu Glu His Pro Val Arg Ile Lys Ala Glu Met Arg
 50                 55                  60

Pro Gly Pro Leu Asp Ala Val Lys Met Ile Gly Gly Lys Ala Phe Ala
 65                 70                  75                  80

Leu Glu Trp Glu Thr Gly Asn Ile Ser Ser Ser His Arg Ala Ile Asn
                85                  90                  95

Lys Met Val Met Gly Met Leu Glu Arg Val Ile Ile Gly Gly Val Leu
            100                 105                 110

Ile Leu Pro Ser Arg Asp Met Tyr Asn Tyr Leu Thr Asp Arg Val Gly
            115                 120                 125

Asn Phe Arg Glu Leu Glu Pro Tyr Phe Ser Val Trp Arg Gln Phe Asn
130                 135                 140

Leu Lys Asp Ala Tyr Leu Ala Ile Val Glu Ile Glu His Asp Ser Val
145                 150                 155                 160

Asp Ala Gln Val Ser Leu Ile Pro Lys Gly Thr Asp Gly Arg Ala Ile
                165                 170                 175

Arg

<210> SEQ ID NO 23
<211> LENGTH: 38
<212> TYPE: DNA
<213> ORGANISM: artificial
<220> FEATURE:
```

<223> OTHER INFORMATION: primer

<400> SEQUENCE: 23
attcaacaag catacaatgc agttaaaaca tctattgt					38

<210> SEQ ID NO 24
<211> LENGTH: 39
<212> TYPE: DNA
<213> ORGANISM: artificial
<220> FEATURE:
<223> OTHER INFORMATION: primer

<400> SEQUENCE: 24
acaaatagat gttttaactg cattgtatgc ttgttgaat					39

<210> SEQ ID NO 25
<211> LENGTH: 39
<212> TYPE: DNA
<213> ORGANISM: artificial
<220> FEATURE:
<223> OTHER INFORMATION: primer

<400> SEQUENCE: 25
caagcataca atgaagttgc aacatctatt tgttcacct					39

<210> SEQ ID NO 26
<211> LENGTH: 39
<212> TYPE: DNA
<213> ORGANISM: artificial
<220> FEATURE:
<223> OTHER INFORMATION: primer

<400> SEQUENCE: 26
aggtgaacaa atagatgttg caacttcatt gtatgcttg					39

<210> SEQ ID NO 27
<211> LENGTH: 39
<212> TYPE: DNA
<213> ORGANISM: artificial
<220> FEATURE:
<223> OTHER INFORMATION: primer

<400> SEQUENCE: 27
acgattaaca acaccgaagc aaattgtaac ggtgtagta					39

<210> SEQ ID NO 28
<211> LENGTH: 40
<212> TYPE: DNA
<213> ORGANISM: artificial
<220> FEATURE:
<223> OTHER INFORMATION: primer

<400> SEQUENCE: 28
acgattaaca acaccgaagc aaattgtaac ggtgtagtat					40

<210> SEQ ID NO 29
<211> LENGTH: 39
<212> TYPE: DNA
<213> ORGANISM: artificial
<220> FEATURE:
<223> OTHER INFORMATION: primer

<400> SEQUENCE: 29
aacggtgtag taccaattgc agaactatgt tacaccta					39

```
<210> SEQ ID NO 30
<211> LENGTH: 39
<212> TYPE: DNA
<213> ORGANISM: artificial
<220> FEATURE:
<223> OTHER INFORMATION: primer

<400> SEQUENCE: 30
taaggtgtaa catagttctg caattggtac tacaccgtt                              39

<210> SEQ ID NO 31
<211> LENGTH: 39
<212> TYPE: DNA
<213> ORGANISM: artificial
<220> FEATURE:
<223> OTHER INFORMATION: primer

<400> SEQUENCE: 31 aaccccttg atatacttgc acttgaaaag aaaaaaggt                               39

<210> SEQ ID NO 32
<211> LENGTH: 39
<212> TYPE: DNA
<213> ORGANISM: artificial
<220> FEATURE:
<223> OTHER INFORMATION: primer

<400> SEQUENCE: 32 acctttttc ttttcaagtg caagtatatc aagggtttt                              39

<210> SEQ ID NO 33
<211> LENGTH: 36
<212> TYPE: DNA
<213> ORGANISM: artificial
<220> FEATURE:
<223> OTHER INFORMATION: primer

<400> SEQUENCE: 33
gatatactta aacttgcaaa gaaaaaaggt ggtccg                                 36

<210> SEQ ID NO 34
<211> LENGTH: 39
<212> TYPE: DNA
<213> ORGANISM: artificial
<220> FEATURE:
<223> OTHER INFORMATION: primer

<400> SEQUENCE: 34
cggaccacct tttttctttg caagtttaag tatatcaag                              39

<210> SEQ ID NO 35
<211> LENGTH: 39
<212> TYPE: DNA
<213> ORGANISM: artificial
<220> FEATURE:
<223> OTHER INFORMATION: primer

<400> SEQUENCE: 35
atacttaaac ttgaaaaggc aaaaggtggt ccgattgat                              39

<210> SEQ ID NO 36
<211> LENGTH: 40
<212> TYPE: DNA
<213> ORGANISM: artificial
<220> FEATURE:
<223> OTHER INFORMATION: primer
```

```
<400> SEQUENCE: 36
atcaatcgga ccaccttttg cctttttcaa gtttaagtat                    40

<210> SEQ ID NO 37
<211> LENGTH: 39
<212> TYPE: DNA
<213> ORGANISM: artificial
<220> FEATURE:
<223> OTHER INFORMATION: primer

<400> SEQUENCE: 37
ggtccgattg atgtttatgc agagttcata gaaaacagt                     39

<210> SEQ ID NO 38
<211> LENGTH: 39
<212> TYPE: DNA
<213> ORGANISM: artificial
<220> FEATURE:
<223> OTHER INFORMATION: primer

<400> SEQUENCE: 38
actgttttct atgaactctg cataaacatc aatcggacc                     39

<210> SEQ ID NO 39
<211> LENGTH: 37
<212> TYPE: DNA
<213> ORGANISM: artificial
<220> FEATURE:
<223> OTHER INFORMATION: primer

<400> SEQUENCE: 39
atagaaaaac agtgaacttg cacgtgtagg tatggaa                       37

<210> SEQ ID NO 40
<211> LENGTH: 39
<212> TYPE: DNA
<213> ORGANISM: artificial
<220> FEATURE:
<223> OTHER INFORMATION: primer

<400> SEQUENCE: 40
aaattccata cctacacgtg caagttcact gttttctat                     39

<210> SEQ ID NO 41
<211> LENGTH: 39
<212> TYPE: DNA
<213> ORGANISM: artificial
<220> FEATURE:
<223> OTHER INFORMATION: primer

<400> SEQUENCE: 41
ggaaatatta gttctgccgc acgttcaatg aacaaactt                     39

<210> SEQ ID NO 42
<211> LENGTH: 39
<212> TYPE: DNA
<213> ORGANISM: artificial
<220> FEATURE:
<223> OTHER INFORMATION: primer

<400> SEQUENCE: 42
aagtttgttc attgaaacgt gcggcagaac taatattcc                     39

<210> SEQ ID NO 43
<211> LENGTH: 39
```

```
<212> TYPE: DNA
<213> ORGANISM: artificial
<220> FEATURE:
<223> OTHER INFORMATION: primer

<400> SEQUENCE: 43
aatattagtt ctgcccacgc atcaatgaac aaacttcta                              39

<210> SEQ ID NO 44
<211> LENGTH: 39
<212> TYPE: DNA
<213> ORGANISM: artificial
<220> FEATURE:
<223> OTHER INFORMATION: primer

<400> SEQUENCE: 44
tagaagtttg ttcattgatg cgtgggcaga actaatatt                              39

<210> SEQ ID NO 45
<211> LENGTH: 42
<212> TYPE: DNA
<213> ORGANISM: artificial
<220> FEATURE:
<223> OTHER INFORMATION: primer

<400> SEQUENCE: 45
gcccaccgtt caatgaacgc acttctatta ggattaaaac at                          42

<210> SEQ ID NO 46
<211> LENGTH: 42
<212> TYPE: DNA
<213> ORGANISM: artificial
<220> FEATURE:
<223> OTHER INFORMATION: primer

<400> SEQUENCE: 46
atgttttaat cctaatagaa gtgcggtcat tgaacggtgg gc                          42

<210> SEQ ID NO 47
<211> LENGTH: 39
<212> TYPE: DNA
<213> ORGANISM: artificial
<220> FEATURE:
<223> OTHER INFORMATION: primer

<400> SEQUENCE: 47
attatcctta tgcctattgc acaattggcc tattatctt                              39

<210> SEQ ID NO 48
<211> LENGTH: 39
<212> TYPE: DNA
<213> ORGANISM: artificial
<220> FEATURE:
<223> OTHER INFORMATION: primer

<400> SEQUENCE: 48
aagataatag gccaattgtg caataggcat aaggataat                              39

<210> SEQ ID NO 49
<211> LENGTH: 39
<212> TYPE: DNA
<213> ORGANISM: artificial
<220> FEATURE:
<223> OTHER INFORMATION: primer

<400> SEQUENCE: 49
```

```
ttggcctatt atcttacagc acgtgttacc aatttcgag                              39

<210> SEQ ID NO 50
<211> LENGTH: 39
<212> TYPE: DNA
<213> ORGANISM: artificial
<220> FEATURE:
<223> OTHER INFORMATION: primer

<400> SEQUENCE: 50
ctcgaaattg gtaacacgtg ctgtaagata ataggccaa                              39

<210> SEQ ID NO 51
<211> LENGTH: 39
<212> TYPE: DNA
<213> ORGANISM: artificial
<220> FEATURE:
<223> OTHER INFORMATION: primer

<400> SEQUENCE: 51
gcctattatc ttacagatgc agttaccaat ttcgaggaa                              39

<210> SEQ ID NO 52
<211> LENGTH: 39
<212> TYPE: DNA
<213> ORGANISM: artificial
<220> FEATURE:
<223> OTHER INFORMATION: primer

<400> SEQUENCE: 52
ttcctcgaaa ttggtaactg catctgtaag ataataggc                              39

<210> SEQ ID NO 53
<211> LENGTH: 39
<212> TYPE: DNA
<213> ORGANISM: artificial
<220> FEATURE:
<223> OTHER INFORMATION: primer

<400> SEQUENCE: 53
cgtgttacca atttcgaggc attagaacct tattttgaa                              39

<210> SEQ ID NO 54
<211> LENGTH: 39
<212> TYPE: DNA
<213> ORGANISM: artificial
<220> FEATURE:
<223> OTHER INFORMATION: primer

<400> SEQUENCE: 54
ttcaaaataa ggttctaatg cctcgaaatt ggtaacacg                              39

<210> SEQ ID NO 55
<211> LENGTH: 39
<212> TYPE: DNA
<213> ORGANISM: artificial
<220> FEATURE:
<223> OTHER INFORMATION: primer

<400> SEQUENCE: 55
accaatttcg aggaattagc accttatttt gaacttact                              39

<210> SEQ ID NO 56
<211> LENGTH: 39
<212> TYPE: DNA
<213> ORGANISM: artificial
```

```
<220> FEATURE:
<223> OTHER INFORMATION: primer

<400> SEQUENCE: 56
agtaagttca aaataaggtg ctaattcctc gaaattggt                              39

<210> SEQ ID NO 57
<211> LENGTH: 42
<212> TYPE: DNA
<213> ORGANISM: artificial
<220> FEATURE:
<223> OTHER INFORMATION: primer

<400> SEQUENCE: 57
ccttattttg aacttactgc aggacaacca tttattttta tt                         42

<210> SEQ ID NO 58
<211> LENGTH: 42
<212> TYPE: DNA
<213> ORGANISM: artificial
<220> FEATURE:
<223> OTHER INFORMATION: primer

<400> SEQUENCE: 58
aataaaaata aatggttgtg ctgcagtaag ttcaaaataa gg                         42

<210> SEQ ID NO 59
<211> LENGTH: 45
<212> TYPE: DNA
<213> ORGANISM: artificial
<220> FEATURE:
<223> OTHER INFORMATION: primer

<400> SEQUENCE: 59
tttattttta ttggatttaa tgctgcagct tataattcta atgtc                      45

<210> SEQ ID NO 60
<211> LENGTH: 45
<212> TYPE: DNA
<213> ORGANISM: artificial
<220> FEATURE:
<223> OTHER INFORMATION: primer

<400> SEQUENCE: 60
gacattagaa ttataagctg cagcattaaa tccaataaaa ataaa                      45

<210> SEQ ID NO 61
<211> LENGTH: 39
<212> TYPE: DNA
<213> ORGANISM: artificial
<220> FEATURE:
<223> OTHER INFORMATION: primer

<400> SEQUENCE: 61
aatgtccctt taattcccgc aggttctgac ggtatgtca                             39

<210> SEQ ID NO 62
<211> LENGTH: 39
<212> TYPE: DNA
<213> ORGANISM: artificial
<220> FEATURE:
<223> OTHER INFORMATION: primer

<400> SEQUENCE: 62
tgacataccg tcagaacctg cgggaattaa agggacatt                             39
```

<210> SEQ ID NO 63
<211> LENGTH: 39
<212> TYPE: DNA
<213> ORGANISM: artificial
<220> FEATURE:
<223> OTHER INFORMATION: primer

<400> SEQUENCE: 63
ttaattccca aggttctgc aggtatgtca aaacgctca                        39

<210> SEQ ID NO 64
<211> LENGTH: 39
<212> TYPE: DNA
<213> ORGANISM: artificial
<220> FEATURE:
<223> OTHER INFORMATION: primer

<400> SEQUENCE: 64
tgagcgtttt gacatacctg cagaaccttt gggaattaa                       39

<210> SEQ ID NO 65
<211> LENGTH: 39
<212> TYPE: DNA
<213> ORGANISM: artificial
<220> FEATURE:
<223> OTHER INFORMATION: primer

<400> SEQUENCE: 65
tctgacggta tgtcaaaagc atcaattaag aaatggaaa                       39

<210> SEQ ID NO 66
<211> LENGTH: 39
<212> TYPE: DNA
<213> ORGANISM: artificial
<220> FEATURE:
<223> OTHER INFORMATION: primer

<400> SEQUENCE: 66
tttccatttc ttaattgatg cttttgacat accgtcaga                       39

<210> SEQ ID NO 67
<211> LENGTH: 54
<212> TYPE: DNA
<213> ORGANISM: artificial
<220> FEATURE:
<223> OTHER INFORMATION: primer

<400> SEQUENCE: 67
ggtggtgcat gcggaggtaa ataaatggaa gtagaaaaag agtttattac tgat      54

<210> SEQ ID NO 68
<211> LENGTH: 51
<212> TYPE: DNA
<213> ORGANISM: artificial
<220> FEATURE:
<223> OTHER INFORMATION: primer

<400> SEQUENCE: 68
ggtggtggta ccctatttgt tttcaacttt atctttccat tcttaattg a          51

<210> SEQ ID NO 69
<211> LENGTH: 39
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (19)..(21)
<223> OTHER INFORMATION: n=a, c, g or t

<400> SEQUENCE: 69
caagcataca atgaagttnn nacatctatt tgttcacct                          39

<210> SEQ ID NO 70
<211> LENGTH: 39
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (19)..(21)
<223> OTHER INFORMATION: n=a. c. g or t

<400> SEQUENCE: 70
aggtgaacaa atagatgtnn naacttcatt gtatgcttg                          39

<210> SEQ ID NO 71
<211> LENGTH: 37
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (16)..(18)
<220> FEATURE:
<221> NAME/KEY: misc_feature
<222> LOCATION: (16)..(18)
<223> OTHER INFORMATION: n=a, c, g, or t

<400> SEQUENCE: 71
gatatactta aacttnnnaa gaaaaaaagg tggtccg                            37

<210> SEQ ID NO 72
<211> LENGTH: 39
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (19)..(21)
<220> FEATURE:
<221> NAME/KEY: misc_feature
<222> LOCATION: (19)..(21)
<223> OTHER INFORMATION: n=a, c, g, or t

<400> SEQUENCE: 72
cggaccacct tttttcttnn naagtttaag tatatcaag                          39

<210> SEQ ID NO 73
<211> LENGTH: 54
<212> TYPE: DNA
<213> ORGANISM: artificial
<220> FEATURE:
<223> OTHER INFORMATION: primer

<400> SEQUENCE: 73
ggtggtgcat gcggaggtaa ataaatgtct aataaaaaac agtcaaatag gcta         54

<210> SEQ ID NO 74
<211> LENGTH: 39
<212> TYPE: DNA

<213> ORGANISM: artificial
<220> FEATURE:
<223> OTHER INFORMATION: primer

<400> SEQUENCE: 74
ggtggtggta cctcacttag atctaagctg ttcaaacaa          39

<210> SEQ ID NO 75
<211> LENGTH: 267
<212> TYPE: PRT
<213> ORGANISM: Escherichia coli RY13
<220> FEATURE:
<221> NAME/KEY: MISC_FEATURE
<222> LOCATION: (1)..(267)
<223> OTHER INFORMATION: Amino acid residues 1-267 correspond to
      residues 4-270 of the protein sequence of EcoRI

<400> SEQUENCE: 75

Lys Lys Gln Ser Asn Arg Leu Thr Glu Gln His Lys Leu Ser Gln Gly
1               5                   10                  15

Val Ile Gly Ile Phe Gly Asp Tyr Ala Lys Ala His Asp Leu Ala Val
            20                  25                  30

Gly Glu Val Ser Lys Leu Val Lys Lys Ala Leu Ser Asn Glu Tyr Pro
        35                  40                  45

Gln Leu Ser Phe Arg Tyr Arg Asp Ser Ile Lys Lys Thr Glu Ile Asn
    50                  55                  60

Glu Ala Leu Lys Lys Ile Asp Pro Asp Leu Gly Gly Thr Leu Phe Val
65                  70                  75                  80

Ser Asn Ser Ser Ile Lys Pro Asp Gly Gly Ile Val Glu Val Lys Asp
                85                  90                  95

Asp Tyr Gly Glu Trp Arg Val Val Leu Val Ala Glu Ala Lys His Gln
            100                 105                 110

Gly Lys Asp Ile Ile Asn Ile Arg Asn Gly Leu Leu Val Gly Lys Arg
        115                 120                 125

Gly Asp Gln Asp Leu Met Ala Ala Gly Asn Ala Ile Glu Arg Ser His
    130                 135                 140

Lys Asn Ile Ser Glu Ile Ala Asn Phe Met Leu Ser Glu Ser His Phe
145                 150                 155                 160

Pro Tyr Val Leu Phe Leu Glu Gly Ser Asn Phe Leu Thr Glu Asn Ile
                165                 170                 175

Ser Ile Thr Arg Pro Asp Gly Arg Val Val Asn Leu Glu Tyr Asn Ser
            180                 185                 190

Gly Ile Leu Asn Arg Leu Asp Arg Leu Thr Ala Ala Asn Tyr Gly Met
        195                 200                 205

Pro Ile Asn Ser Asn Leu Cys Ile Asn Lys Phe Val Asn His Lys Asp
    210                 215                 220

Lys Ser Ile Met Leu Gln Ala Ala Ser Ile Tyr Thr Gln Gly Asp Gly
225                 230                 235                 240

Arg Glu Trp Asp Ser Lys Ile Met Phe Glu Ile Met Phe Asp Ile Ser
                245                 250                 255

Thr Thr Ser Leu Arg Val Leu Gly Arg Asp Leu
            260                 265

<210> SEQ ID NO 76
<211> LENGTH: 265
<212> TYPE: PRT
<213> ORGANISM: Rhodopseudomonas sphaeroides
<220> FEATURE:
<221> NAME/KEY: MISC_FEATURE
<222> LOCATION: (1)..(265)
<223> OTHER INFORMATION: amino acid residues 1-265 correspond to
      residues 10-274 of the protein sequence of RsrI

<400> SEQUENCE: 76

Lys Gly Gln Ala Leu Arg Leu Gly Ile Gln Gln Glu Leu Gly Gly
1               5                   10                  15

Pro Leu Ser Ile Phe Gly Ala Ala Gln Lys His Asp Leu Ser Ile
            20                  25                  30

Arg Glu Val Thr Ala Gly Val Leu Thr Lys Leu Ala Glu Asp Phe Pro
        35                  40                  45

Asn Leu Glu Phe Gln Leu Arg Thr Ser Leu Thr Lys Lys Ala Ile Asn
    50                  55                  60

Glu Lys Leu Arg Ser Phe Asp Pro Arg Leu Gly Gln Ala Leu Phe Val
65                  70                  75                  80

Glu Ser Ala Ser Ile Arg Pro Asp Gly Gly Ile Thr Glu Val Lys Asp
                85                  90                  95

Arg His Gly Asn Trp Arg Val Ile Leu Val Gly Glu Ser Lys His Gln
            100                 105                 110

Gly Asn Asp Val Glu Lys Ile Leu Ala Gly Val Leu Gln Gly Lys Ala
        115                 120                 125

Lys Asp Gln Asp Phe Met Ala Ala Gly Asn Ala Ile Glu Arg Met His
    130                 135                 140

Lys Asn Val Leu Glu Leu Arg Asn Tyr Met Leu Asp Glu Lys His Phe
145                 150                 155                 160

Pro Tyr Val Val Phe Leu Gln Gly Ser Asn Phe Ala Thr Glu Ser Phe
                165                 170                 175

Glu Val Thr Arg Pro Asp Gly Arg Val Val Lys Ile Val His Asp Ser
            180                 185                 190

Gly Met Leu Asn Arg Ile Asp Arg Val Thr Ala Ser Ser Leu Ser Arg
        195                 200                 205

Glu Ile Asn Gln Asn Tyr Cys Glu Asn Ile Val Val Arg Ala Gly Ser
    210                 215                 220

Phe Asp His Met Phe Gln Ile Ala Ser Leu Tyr Cys Lys Ala Ala Pro
225                 230                 235                 240

Trp Thr Ala Gly Glu Met Ala Glu Ala Met Leu Ala Val Ala Lys Thr
                245                 250                 255

Ser Leu Arg Ile Ile Ala Asp Asp Leu
            260                 265

<210> SEQ ID NO 77
<211> LENGTH: 39
<212> TYPE: DNA
<213> ORGANISM: artificial
<220> FEATURE:
<223> OTHER INFORMATION: primer

<400> SEQUENCE: 77
gattgggtgg cgcagaaatt tcaaacgggc cagcagtcg                        39

<210> SEQ ID NO 78
<211> LENGTH: 39
<212> TYPE: DNA
<213> ORGANISM: artificial
<220> FEATURE:
<223> OTHER INFORMATION: primer

<400> SEQUENCE: 78
cgactgctgg cccgtttgaa atttctgcgc cacccaatc                              39

<210> SEQ ID NO 79
<211> LENGTH: 272
<212> TYPE: PRT
<213> ORGANISM: Agrobacterium gelatinovorum

<400> SEQUENCE: 79

Met Arg Leu Asp Leu Asp Phe Gly Arg Gly Leu Val Ala His Val Met
1               5                   10                  15

Leu Asp Asn Val Ser Glu Glu Gln Tyr Gln Gln Ile Ser Asp Tyr Phe
            20                  25                  30

Val Pro Leu Val Asn Lys Pro Lys Leu Lys Ser Arg Asp Ala Ile Gly
        35                  40                  45

Gln Ala Phe Val Met Ala Thr Glu Val Cys Pro Asp Ala Asn Pro Ser
    50                  55                  60

Asp Leu Trp His His Val Leu Tyr Arg Ile Tyr Ile Arg Glu Lys Ile
65                  70                  75                  80

Gly Thr Asp Pro Ser Gln Ser Trp Val Arg Thr Ser Gly Glu Ala Phe
                85                  90                  95

Glu Val Ala Leu Val Glu Arg Tyr Asn Pro Val Leu Ala Arg His Gly
            100                 105                 110

Ile Arg Leu Thr Ala Leu Phe Lys Gly Gln Lys Gly Leu Ala Leu Thr
        115                 120                 125

Arg Met Gly Val Ala Asp Arg Val Gly Ser Arg Lys Val Asp Val Met
    130                 135                 140

Ile Glu Lys Gln Gly Gly Gly Arg Ser Pro Asp Ala Glu Gly Phe Gly
145                 150                 155                 160

Val Val Gly Gly Ile His Ala Lys Val Ser Leu Ala Glu Arg Val Ser
                165                 170                 175

Asp Asp Ile Pro Ala Ser Arg Ile Met Met Gly Glu Gly Leu Leu Ser
            180                 185                 190

Val Leu Ser Thr Leu Asp Val Lys Ser Phe Pro Pro His Gly Asp
        195                 200                 205

Leu Val Asn Arg Gly Glu Leu Gly Thr Pro Asp Arg Pro Ser Asp Lys
    210                 215                 220

Arg Asn Tyr Ile Glu Gly His Gly Asp Phe Ser Ala Cys Phe Ser Tyr
225                 230                 235                 240

Asn Leu Arg Thr Pro Pro Ser Asn Ala Thr Thr Pro Ser Gly Arg His
                245                 250                 255

Ile Tyr Val Ser Ala Ser Leu Val Arg Thr Thr Ser Ser Pro Thr Thr
            260                 265                 270

<210> SEQ ID NO 80
<211> LENGTH: 358
<212> TYPE: PRT
<213> ORGANISM: Anabaena variabilis

<400> SEQUENCE: 80

Met Glu Glu Asp Leu Asp Leu Ser Glu Asn Ile Glu Ala Ala Ser Ala
1               5                   10                  15

Glu Leu Thr Thr Leu Tyr Gln Val Ala Ala Asp Ala Met Lys Asp Tyr
            20                  25                  30

Ile Glu Ile Tyr Leu Ala Leu Ser Lys Gln Ser Asp Gly Phe Ser Asn
        35                  40                  45

Ile Asn Asn Leu Asp Leu Thr Ser Arg Asn Arg Arg Leu Val Val Ile

His Gly Leu Ser Leu Glu Leu Asp Pro Asp Thr Ser Thr Pro Glu Glu
 65                  70                  75                  80

Ile Lys Arg Glu Ala Glu Arg Met Leu Ala Ile Ala Leu Asp Thr Glu
                 85                  90                  95

Ser Ala Ile Thr Ala Gly Val Tyr Glu Lys Met Arg Leu Phe Ala Ser
            100                 105                 110

Ser Leu Val Asp Gln Leu Phe Glu Gln Thr Asp Glu Leu Asn Ser Leu
        115                 120                 125

Ser Ser Glu Tyr Leu Ser Ala Asn Pro Gly Phe Leu Pro Phe Phe Gln
130                 135                 140

Gln Leu Ala Gly Leu Arg Ser Lys Ser Glu Leu Lys Arg Glu Val Gly
145                 150                 155                 160

Asn Ala Ser Asp Asn Ser Ile Ser Lys Ala Val Ala Glu Arg Ile Leu
                165                 170                 175

Glu Arg Ile Ile Arg Asn Leu Arg Ile Arg Thr Phe Ser Lys Glu Lys
            180                 185                 190

Leu Leu Gln Ala Val Glu Pro Thr Leu Glu Gly Ile Val Arg Asp Leu
        195                 200                 205

Val Gly Lys Val Leu Leu Glu Asn Ile Val Ala Asp Ala Leu Ser Asp
210                 215                 220

Leu Gln Val Pro Phe Met Arg Glu Ser Glu Tyr Gln Ser Leu Lys Gly
225                 230                 235                 240

Val Ile Tyr Asp Phe Arg Ala Asp Phe Val Ile Pro Asp Ala Gln Asn
                245                 250                 255

Pro Ile Ala Phe Ile Glu Val Arg Lys Ser Ser Thr Arg His Ala Ser
            260                 265                 270

Leu Tyr Ala Lys Asp Lys Met Phe Ser Ala Ile Asn Trp Lys Gly Lys
        275                 280                 285

Asn Lys Arg Leu Leu Gly Ile Leu Val Val Glu Gly Pro Trp Thr Arg
290                 295                 300

Glu Thr Leu Arg Val Met Ala Asn Val Phe Asp Tyr Val Thr Pro Leu
305                 310                 315                 320

Thr Arg Val Ser Gln Val Ala Glu Ala Ile Arg Ala Tyr Leu Asp Gly
                325                 330                 335

Asp Lys Thr Arg Leu Lys Trp Leu Val Asn Phe Ser Ile Glu Glu Ala
            340                 345                 350

Asp His Asp Asn Ile Thr
        355

<210> SEQ ID NO 81
<211> LENGTH: 530
<212> TYPE: PRT
<213> ORGANISM: Bacillus stearothermophilus B61

<400> SEQUENCE: 81

Met Ala Lys Tyr Gly Arg Gly Lys Phe Leu Pro His Gln Asn Tyr Ile
1               5                   10                  15

Asp Tyr Met His Phe Ile Val Asn His Lys Asn Tyr Ser Gly Met Pro
                20                  25                  30

Asn Ala Ile Gly Glu Asp Gly Arg Ile Asn Trp Gln Val Ser Ser Gly
            35                  40                  45

Lys Thr Thr Ser Phe Tyr Glu Tyr Tyr Gln Ala Arg Phe Glu Trp Trp
        50                  55                  60

-continued

```
Glu Lys Lys Ala Asp Glu Leu Asn Leu Pro Gly Thr Gly Asn Ser Asn
 65                  70                  75                  80

Lys Arg Phe Ser Leu Ala Ala Arg Leu Ile His Pro Thr Gly Gln Arg
                 85                  90                  95

Pro Cys Arg Leu Cys Gly Lys Tyr Gln Tyr Val Gly Tyr Met Tyr Val
            100                 105                 110

Ser His Asn Leu Tyr Lys Arg Trp Ser Lys Ile Thr Gly Arg Glu Asp
        115                 120                 125

Leu Phe Phe Lys Lys Gln Asn Ile Ile Glu Ala Ala Asn Ile Phe Lys
    130                 135                 140

Ser Ile Met Gly Glu Gln Ala Leu Ile Asn Glu Leu Thr Thr Ile Phe
145                 150                 155                 160

Pro Glu Arg Lys Asp Tyr Phe Asn Arg Leu Pro Asn Ile Glu Asp Phe
                165                 170                 175

Phe Val Ser Ser Ser His Ile Lys Asn Asn Gly Asn Tyr Ile Ser Pro
            180                 185                 190

Gly Phe Met Ala Asn Pro Pro Asp Arg Leu Asp Gly Phe His Asp Tyr
        195                 200                 205

Gly Ile Cys Cys Arg Lys Glu Lys Asp Pro Gly Arg His Asp Asp Asn
    210                 215                 220

Met Arg Leu Tyr Asn His Asp Arg Arg Ala Phe Met Trp Trp Ser Glu
225                 230                 235                 240

Gly Asp Trp Ala Leu Ala Asp Ala Leu Tyr Asn Lys Ala Gly Ala Gly
                245                 250                 255

Lys Cys Ala Asp Pro Asp Cys Gln Lys Glu Val Glu Lys Ile Ser Pro
            260                 265                 270

Asp His Val Gly Pro Ile Ser Cys Gly Phe Lys Gln Ile Pro Phe Phe
        275                 280                 285

Lys Pro Leu Cys Ala Ser Cys Asn Ser Ala Lys Asn Arg Arg Phe Ser
    290                 295                 300

Tyr Gln Asp Val Lys Glu Leu Leu Lys Tyr Glu Asn Tyr Thr Gly Asp
305                 310                 315                 320

Ser Val Ala Ser Trp Gln Val Arg Ala Leu Trp Asp Asn Cys Lys His
                325                 330                 335

Leu Val Lys Asn Asp Asp Ser Lys Leu Leu Ser Asn Leu Met Arg
            340                 345                 350

Ser Leu Gln Asp Tyr Tyr Leu Arg Ser Leu Tyr Lys Leu Phe Ser Asn
        355                 360                 365

Gly Phe Ala His Leu Leu Ser Tyr Phe Leu Thr Pro Glu Tyr Ala His
    370                 375                 380

Tyr Lys Ile Thr Phe Glu Gly Leu Asn Thr Ser Thr Leu Glu Tyr Glu
385                 390                 395                 400

Arg Tyr Tyr Lys Thr Phe Lys Lys Thr Lys Ser Thr Ser Ser Leu Ala
                405                 410                 415

Ala Arg Ile Val Arg Ile Ala Phe Glu Glu Leu Glu Ile Tyr Asn Ser
            420                 425                 430

Lys Asp Ile Asn Glu Arg Lys Leu Ile Lys Phe Asp Thr Ser Ser Trp
        435                 440                 445

Glu Lys Asp Phe Glu Asn Ile Ile Ser Tyr Ala Thr Lys Asn Leu Ser
    450                 455                 460

Leu Asp Glu Glu Ala Ser Lys Trp Asn Lys Val Leu Thr Asp Lys Asn
465                 470                 475                 480

Leu Ser Ser Thr Glu Lys Asp Lys Lys Ile Ser Ser Leu Leu Glu Asp
```

```
                485                 490                 495
Lys Asn Tyr Glu Val Tyr Lys Lys Gln Phe Tyr Ile Leu Lys Asp Leu
                500                 505                 510
Leu Val Glu His Phe Asn Lys Ile Gly Glu Gln Ile Ala Lys Asp Tyr
                515                 520                 525
Met Lys
    530

<210> SEQ ID NO 82
<211> LENGTH: 301
<212> TYPE: PRT
<213> ORGANISM: Enterobacter agglomerans

<400> SEQUENCE: 82

Met Lys Lys Arg Arg Asp Leu Val Glu Val Phe Gly Tyr Asn Pro Met
1               5                   10                  15
Asp Leu Ser Pro Glu Val Arg Ala Leu Trp Asn Leu Gly Ala Cys Pro
                20                  25                  30
Phe Leu Asn Lys Glu Cys Ile Lys Ile Asn His Asp Gln Thr Ile Ile
            35                  40                  45
Tyr Gly Thr Cys Ser Val Thr Ser Pro Tyr Gly Asp Val Ile Ile Cys
        50                  55                  60
Pro Asn Arg Leu Tyr Ala Asn Asp Tyr Glu Thr Leu His Lys Val Ser
65                  70                  75                  80
Arg Asp Ala Phe Gly Asp Asp Val Pro Phe Leu Thr Tyr Ser Asn Phe
                85                  90                  95
Ile Lys Tyr Arg Ala Thr Tyr Lys Asp Cys Ile Val Ala Leu Gly Lys
            100                 105                 110
Asn Ser Gly Lys Glu Val Gln Val Gly Arg Ala Leu Ser Met Asp Trp
        115                 120                 125
Val Leu Val Arg Ile Thr Asp Gly Glu Leu Lys Glu Tyr Val Gly Val
    130                 135                 140
Glu Ile Gln Ser Ile Asp Ile Thr Gly Asn Tyr Arg Asp Ala Trp His
145                 150                 155                 160
Ala Tyr Lys Asn Leu Lys Pro Ile Asp Ile Asp Asn Leu Pro Thr
                165                 170                 175
Ser Gln His Gly Leu Asn Trp Ala Asn Val His Lys Arg Leu Ile Pro
            180                 185                 190
Gln Ile Ile Arg Lys Gly Val Val Tyr Ser Arg Ser Asn Tyr Val Lys
        195                 200                 205
Lys Gly Leu Tyr Phe Ile Leu Pro Glu Ile Val Tyr Asn Lys Phe Glu
    210                 215                 220
Asp Val Ile Gly Ala Asp Ile Pro Leu Leu Lys Thr Gln Thr Asn Lys
225                 230                 235                 240
Ser Ile Thr Val His Thr Tyr Ser Leu Gly Glu Pro Ala Ala Asn Gly
                245                 250                 255
Glu Gln Arg Lys Leu Ile Ser Glu Arg Glu Ile Ile Phe Asp Leu Asp
            260                 265                 270
Glu Phe Ser Lys Arg Phe Thr Thr Gly Pro Asn Leu Pro Lys Gly Asp
        275                 280                 285
Asp Leu Asp Ala Val Ile Lys Lys Ala Leu Gly Met Met
    290                 295                 300

<210> SEQ ID NO 83
<211> LENGTH: 277
```

<212> TYPE: PRT
<213> ORGANISM: Escherichia coli RY13

<400> SEQUENCE: 83

Met Ser Asn Lys Lys Gln Ser Asn Arg Leu Thr Glu Gln His Lys Leu
1               5                   10                  15

Ser Gln Gly Val Ile Gly Ile Phe Gly Asp Tyr Ala Lys Ala His Asp
            20                  25                  30

Leu Ala Val Gly Glu Val Ser Lys Leu Val Lys Ala Leu Ser Asn
        35                  40                  45

Glu Tyr Pro Gln Leu Ser Phe Arg Tyr Arg Asp Ser Ile Lys Lys Thr
    50                  55                  60

Glu Ile Asn Glu Ala Leu Lys Lys Ile Asp Pro Asp Leu Gly Gly Thr
65                  70                  75                  80

Leu Phe Val Ser Asn Ser Ser Ile Lys Pro Asp Gly Gly Ile Val Glu
                85                  90                  95

Val Lys Asp Asp Tyr Gly Glu Trp Arg Val Val Leu Val Ala Glu Ala
            100                 105                 110

Lys His Gln Gly Lys Asp Ile Ile Asn Ile Arg Asn Gly Leu Leu Val
        115                 120                 125

Gly Lys Arg Gly Asp Gln Asp Leu Met Ala Ala Gly Asn Ala Ile Glu
    130                 135                 140

Arg Ser His Lys Asn Ile Ser Glu Ile Ala Asn Phe Met Leu Ser Glu
145                 150                 155                 160

Ser His Phe Pro Tyr Val Leu Phe Leu Glu Gly Ser Asn Phe Leu Thr
                165                 170                 175

Glu Asn Ile Ser Ile Thr Arg Pro Asp Gly Arg Val Val Asn Leu Glu
            180                 185                 190

Tyr Asn Ser Gly Ile Leu Asn Arg Leu Asp Arg Leu Thr Ala Ala Asn
        195                 200                 205

Tyr Gly Met Pro Ile Asn Ser Asn Leu Cys Ile Asn Lys Phe Val Asn
    210                 215                 220

His Lys Asp Lys Ser Ile Met Leu Gln Ala Ala Ser Ile Tyr Thr Gln
225                 230                 235                 240

Gly Asp Gly Arg Glu Trp Asp Ser Lys Ile Met Phe Glu Ile Met Phe
                245                 250                 255

Asp Ile Ser Thr Thr Ser Leu Arg Val Leu Gly Arg Asp Leu Phe Glu
            260                 265                 270

Gln Leu Thr Ser Lys
        275

<210> SEQ ID NO 84
<211> LENGTH: 245
<212> TYPE: PRT
<213> ORGANISM: Escherichia coli J62 pLG74

<400> SEQUENCE: 84

Met Ser Leu Arg Ser Asp Leu Ile Asn Ala Leu Tyr Asp Glu Asn Gln
1               5                   10                  15

Lys Tyr Asp Val Cys Gly Ile Ile Ser Ala Glu Gly Lys Ile Tyr Pro
            20                  25                  30

Leu Gly Ser Asp Thr Lys Val Leu Ser Thr Ile Phe Glu Leu Phe Ser
        35                  40                  45

Arg Pro Ile Ile Asn Lys Ile Ala Glu Lys His Gly Tyr Ile Val Glu
    50                  55                  60

Glu Pro Lys Gln Gln Asn His Tyr Pro Asp Phe Thr Leu Tyr Lys Pro
65                  70                  75                  80

Ser Glu Pro Asn Lys Lys Ile Ala Ile Asp Ile Lys Thr Thr Tyr Thr
                85                  90                  95

Asn Lys Glu Asn Glu Lys Ile Lys Phe Thr Leu Gly Gly Tyr Thr Ser
            100                 105                 110

Phe Ile Arg Asn Asn Thr Lys Asn Ile Val Tyr Pro Phe Asp Gln Tyr
        115                 120                 125

Ile Ala His Trp Ile Ile Gly Tyr Val Tyr Thr Arg Val Ala Thr Arg
    130                 135                 140

Lys Ser Ser Leu Lys Thr Tyr Asn Ile Asn Glu Leu Asn Glu Ile Pro
145                 150                 155                 160

Lys Pro Tyr Lys Gly Val Lys Val Phe Leu Gln Asp Lys Trp Val Ile
                165                 170                 175

Ala Gly Asp Leu Ala Gly Ser Gly Asn Thr Thr Asn Ile Gly Ser Ile
            180                 185                 190

His Ala His Tyr Lys Asp Phe Val Glu Gly Lys Gly Ile Phe Asp Ser
        195                 200                 205

Glu Asp Glu Phe Leu Asp Tyr Trp Arg Asn Tyr Glu Arg Thr Ser Gln
    210                 215                 220

Leu Arg Asn Asp Lys Tyr Asn Asn Ile Ser Glu Tyr Arg Asn Trp Ile
225                 230                 235                 240

Tyr Arg Gly Arg Lys
                245

<210> SEQ ID NO 85
<211> LENGTH: 300
<212> TYPE: PRT
<213> ORGANISM: Haemophilus influenzae Rd (exo-mutant)

<400> SEQUENCE: 85

Met Lys Lys Ser Ala Leu Glu Lys Leu Leu Ser Leu Ile Glu Asn Leu
1               5                   10                  15

Thr Asn Gln Glu Phe Lys Gln Ala Thr Asn Ser Leu Ile Ser Phe Ile
            20                  25                  30

Tyr Lys Leu Asn Arg Asn Glu Val Ile Glu Leu Val Arg Ser Ile Gly
        35                  40                  45

Ile Leu Pro Glu Ala Ile Lys Pro Ser Ser Thr Gln Glu Lys Leu Phe
    50                  55                  60

Ser Lys Ala Gly Asp Ile Val Leu Ala Lys Ala Phe Gln Leu Leu Asn
65                  70                  75                  80

Leu Asn Ser Lys Pro Leu Glu Gln Arg Gly Asn Ala Gly Asp Val Ile
                85                  90                  95

Ala Leu Ser Lys Glu Phe Asn Tyr Gly Leu Val Ala Asp Ala Lys Ser
            100                 105                 110

Phe Arg Leu Ser Arg Thr Ala Lys Asn Gln Lys Asp Phe Lys Val Lys
        115                 120                 125

Ala Leu Ser Glu Trp Arg Glu Asp Lys Asp Tyr Ala Val Leu Thr Ala
    130                 135                 140

Pro Phe Phe Gln Tyr Pro Thr Lys Ser Gln Ile Phe Lys Gln Ser
145                 150                 155                 160

Leu Asp Glu Asn Val Leu Leu Phe Ser Trp Glu His Leu Ala Ile Leu
                165                 170                 175

Leu Gln Leu Asp Leu Glu Glu Thr Asn Ile Phe Pro Phe Glu Gln Leu
            180                 185                 190

```
Trp Asn Phe Pro Lys Lys Gln Ser Lys Thr Ser Val Ser Asp Ala
        195                 200                 205

Glu Asn Asn Phe Met Arg Asp Phe Asn Lys Tyr Phe Met Asp Leu Phe
210                 215                 220

Lys Ile Asp Lys Asp Thr Leu Asn Gln Leu Leu Gln Lys Glu Ile Asn
225                 230                 235                 240

Phe Ile Glu Glu Arg Ser Leu Ile Glu Lys Glu Tyr Trp Lys Lys Gln
                245                 250                 255

Ile Asn Ile Ile Lys Asn Phe Thr Arg Glu Glu Ala Ile Glu Ala Leu
                260                 265                 270

Leu Lys Asp Ile Asn Met Ser Ser Lys Ile Glu Thr Ile Asp Ser Phe
            275                 280                 285

Ile Lys Gly Ile Lys Ser Asn Asp Arg Leu Tyr Leu
            290                 295                 300

<210> SEQ ID NO 86
<211> LENGTH: 254
<212> TYPE: PRT
<213> ORGANISM: Haemophilus parainfluenzae

<400> SEQUENCE: 86

Met Lys Tyr Glu Glu Ile Asn Phe Lys Val Pro Val Glu Ser Pro Tyr
1               5                   10                  15

Tyr Pro Asn Tyr Ser Gln Cys Val Ile Glu Arg Ile Tyr Ser Ile Leu
            20                  25                  30

Arg Asn Gln Lys Asp Met Gly Asp Arg Ile Ile Ile Asn Thr Asn
        35                  40                  45

Leu Lys Lys Gly Leu Pro Leu Glu Asn Ile Asn Lys Ile Ala Gly Pro
50                  55                  60

Met Ile Glu Ala Trp Ala Glu Glu Val Phe Ser Gly Ile Arg Asp Asn
65                  70                  75                  80

Arg Asp Asn Gln Tyr Asn Leu Ile Asn Val Glu Ala Gln Glu Arg Leu
                85                  90                  95

Gly Ile Ser Asp Ile Ile Leu Gln Phe Gln Val Asn Asn Asn Val Ile
            100                 105                 110

Thr Gly Asn Val Asp Val Lys Ala Thr Ser Asn Asp Ile Pro Asp Ser
        115                 120                 125

Gly Lys Ser Pro Asn Ile Thr Ser Phe Ser Arg Ile Arg Thr Ala Tyr
    130                 135                 140

Val Lys Asp Pro Asn Phe Ile Phe Ile Ile Leu Ser Ile Lys His Ser
145                 150                 155                 160

Val Tyr Val Lys Arg Asn Glu Tyr Thr Asn Leu Met Asp Gly Ile Met
                165                 170                 175

Gln Ile Ile Asp Phe Asn Val Tyr Asp Leu Lys Tyr Ile Ser Asp Ser
            180                 185                 190

Asp Ile Ser Tyr Asn Pro Ala Leu Gly Thr Gly Gln Ile Gln Ile Lys
        195                 200                 205

Asp Ile His Tyr Val Ser Ser Gln Lys Arg Thr Thr Trp Gln Met Cys
    210                 215                 220

Gln Leu Leu Asp Leu Lys Tyr Leu Arg Ser Lys Lys Arg Thr Ile Glu
225                 230                 235                 240

Gln Phe Tyr Asn Glu Ala Lys Arg Asn Lys Trp Ile Lys Asp
                245                 250
```

```
<210> SEQ ID NO 87
<211> LENGTH: 218
<212> TYPE: PRT
<213> ORGANISM: Klebsiella pnermoniae OK8

<400> SEQUENCE: 87
```

Met Asp Val Phe Asp Lys Val Tyr Ser Asp Asn Asn Ser Tyr Asp
1               5                   10                  15

Gln Lys Thr Val Ser Gln Arg Ile Glu Ala Leu Phe Leu Asn Asn Leu
            20                  25                  30

Gly Lys Val Val Thr Arg Gln Gln Ile Ile Arg Ala Ala Thr Asp Pro
        35                  40                  45

Lys Thr Gly Lys Gln Pro Glu Asn Trp His Gln Arg Leu Ser Glu Leu
    50                  55                  60

Arg Thr Asp Lys Gly Tyr Thr Ile Leu Ser Trp Arg Asp Met Lys Val
65                  70                  75                  80

Leu Ala Pro Gln Glu Tyr Ile Met Pro His Ala Thr Arg Arg Pro Lys
                85                  90                  95

Ala Ala Lys Arg Val Leu Pro Thr Lys Glu Thr Trp Glu Gln Val Leu
            100                 105                 110

Asp Arg Ala Asn Tyr Ser Cys Glu Trp Gln Gly Asp Gly Gln His Cys
        115                 120                 125

Gly Leu Val Glu Gly Asp Ile Asp Pro Ile Gly Gly Thr Val Lys
    130                 135                 140

Leu Thr Pro Asp His Met Thr Pro His Ser Ile Asp Pro Ala Thr Asp
145                 150                 155                 160

Val Asn Asp Pro Lys Met Trp Gln Ala Leu Cys Gly Arg His Gln Val
                165                 170                 175

Met Lys Lys Asn Tyr Trp Asp Ser Asn Asn Gly Lys Ile Asn Val Ile
            180                 185                 190

Gly Ile Leu Gln Ser Val Asn Glu Lys Gln Lys Asn Asp Ala Leu Glu
        195                 200                 205

Phe Leu Leu Asn Tyr Tyr Gly Leu Lys Arg
    210                 215

```
<210> SEQ ID NO 88
<211> LENGTH: 288
<212> TYPE: PRT
<213> ORGANISM: Nocardia corallina

<400> SEQUENCE: 88
```

Met Ala Thr Ala Pro Gly His Leu Leu Gly Gln Ile Ile Gly Asn Val
1               5                   10                  15

Met Glu Glu Ala Leu Lys Pro Val Leu Gln Glu Met Ala Asp Arg His
            20                  25                  30

Asp Leu Tyr Leu Asp Ser Lys Gly Leu Arg Pro Gly Val Arg Ser Gly
        35                  40                  45

Ala Leu Val Thr Trp Thr Asp Asp Leu Gly Asn Asn His Asp Leu Asp
    50                  55                  60

Phe Val Leu Glu Arg Gly Gly Ser Ala Thr Lys Ala Gly Asn Pro Ala
65                  70                  75                  80

Ala Phe Ile Glu Ala Ala Trp Arg Arg Tyr Thr Lys His Ser Lys Ala
                85                  90                  95

Lys Ala Gln Glu Ile Gln Gly Ala Val Leu Pro Val Leu Ala Ala Trp
            100                 105                 110

Asn Asn Val Lys Pro Thr Pro Ala Ala Val Val Ala Gly Gln Trp Thr

```
            115                 120                 125
Ala Pro Ser Leu Gln Gln Met Arg Ser Asn Gly Phe Val Val Leu His
        130                 135                 140
Leu His Phe Pro Thr Thr Ala Gln Val Phe Gly Gly Asn Gly Ile Asn
145                 150                 155                 160
Ile Glu Gly Thr Gly Glu Gly Thr Pro Asp Ala Phe Trp Gln Gln Gln
                165                 170                 175
Cys Asp Ala Tyr Thr Ser Lys Ser Glu Ala Asp Lys Asp Ser Leu Ala
            180                 185                 190
Thr Ala Leu Arg Thr Ala His Ala Gln Glu Phe Arg Thr Phe Val Ala
            195                 200                 205
Glu Leu Glu Arg Arg Val Val Arg Ala Ile Asp Tyr Val Val Val Thr
        210                 215                 220
Pro Leu His Gly His Gly Ser Gln Tyr Thr Ser Ile Glu Asn Ala Ile
225                 230                 235                 240
Glu Ala Val Arg Thr Tyr Ser Cys Gly Glu Glu Ser Ala Pro Phe Leu
                245                 250                 255
Arg Phe Glu Ile Arg Ile Ser Tyr Thr Asn Gly Asp Val Ile Gln Ala
            260                 265                 270
Thr Phe Gly Ser Ser Asp Ala Ile Glu Phe Leu Asp Thr Phe Asn
        275                 280                 285

<210> SEQ ID NO 89
<211> LENGTH: 328
<212> TYPE: PRT
<213> ORGANISM: Neisseria mucosa

<400> SEQUENCE: 89

Met Ser Ser Tyr His Asp Asp Leu Asn Ile Leu Asn Val Asp Phe Asn
1               5                   10                  15
His Leu Arg Leu Thr Glu Leu Ile Lys Leu Ala Asp Gln Ala Glu Pro
            20                  25                  30
Phe Tyr Leu Trp Val Glu Lys Ile Phe Arg Gln Val Ser Gly Arg Ala
        35                  40                  45
Asp Ser Leu Glu Thr Ile Ile Glu Val Glu Glu Arg Val Val Leu Lys
    50                  55                  60
Met Ala Ile Leu Thr Cys Phe Thr Ser Asp Glu Lys Glu Leu Pro Lys
65                  70                  75                  80
Leu Phe Asn Gly Val Gly Val Pro Tyr Pro His Ile Lys Ala Cys Tyr
                85                  90                  95
Phe Phe Phe Ala Trp Leu Val Arg Asp Ala Ala Thr Gln Arg Leu Asp
            100                 105                 110
Pro Leu Ile Arg Glu Ala Phe Thr Gln Leu Lys Ser Ile His Pro Gln
        115                 120                 125
Met Lys Lys Thr Glu Leu Glu Ser Glu Ile Phe Ser Gln Leu Leu Val
    130                 135                 140
Asn Tyr Arg Asn Glu Leu Ile His Phe Ser Trp Pro Val Ile Arg Glu
145                 150                 155                 160
Val Leu Ile Ser Arg Leu Glu Gly Ser Arg Arg Ala Ala Arg Gly Ser
                165                 170                 175
Tyr Leu Glu Leu Phe Val Arg Thr Ala Leu Ala Gln Ser Ile Thr Tyr
            180                 185                 190
Phe Tyr Lys Ile Tyr Gly Asn Tyr Gly Lys Phe Leu Asp Val Lys Ile
        195                 200                 205
```

His Asp Lys Pro Leu Lys Val Lys Asn Arg Thr Tyr Asp Val Val Ala
210             215                 220

Glu Leu Ile Gly Asn Asn His Asn Thr Gln Tyr Leu Ile Leu Pro Val
225                 230                 235                 240

Lys Thr Arg Glu Thr Gln Gly Gly His Ala His Leu Phe Thr Arg
            245                 250                 255

Asp Ile Glu Gln Ser Asn Asn Asp Ile Arg Glu Leu Tyr Pro Asn Ala
                260                 265                 270

Val Ile Ala Pro Val Ile Ile Ala Glu Asn Trp Ser Asp Thr Glu Lys
                275                 280                 285

Asp Leu Glu Asn Val Gly Tyr Asn Asp Ile Phe His Phe Ser Val Asn
            290                 295                 300

Pro Asn Arg Phe Ala Gly Phe Ser Asp Val Glu Gln Ile Arg Leu Asn
305                 310                 315                 320

Arg Leu Val Glu Arg Ile Leu Leu
                325

<210> SEQ ID NO 90
<211> LENGTH: 383
<212> TYPE: PRT
<213> ORGANISM: Nocardia otitidis-caviarum

<400> SEQUENCE: 90

Met Arg Ser Asp Thr Ser Val Glu Pro Glu Gly Ala Asn Phe Ile Ala
1               5                   10                  15

Glu Phe Phe Gly His Arg Val Tyr Pro Glu Val Val Ser Thr Glu Ala
            20                  25                  30

Ala Arg Asn Asp Gln Ala Thr Gly Thr Cys Pro Phe Leu Thr Ala Ala
        35                  40                  45

Lys Leu Val Glu Thr Ser Cys Val Lys Ala Glu Thr Ser Arg Gly Val
    50                  55                  60

Cys Val Val Asn Thr Ala Val Asp Asn Glu Arg Tyr Asp Trp Leu Val
65                  70                  75                  80

Cys Pro Asn Arg Ala Leu Asp Pro Leu Phe Met Ser Ala Ala Ser Arg
                85                  90                  95

Lys Leu Phe Gly Tyr Gly Pro Thr Glu Pro Leu Gln Phe Ile Ala Ala
            100                 105                 110

Pro Thr Leu Ala Asp Gln Ala Val Arg Asp Gly Ile Arg Glu Trp Leu
        115                 120                 125

Asp Arg Gly Val His Val Val Ala Tyr Phe Gln Glu Lys Leu Gly Gly
130                 135                 140

Glu Leu Ser Ile Ser Lys Thr Asp Ser Ser Pro Glu Phe Ser Phe Asp
145                 150                 155                 160

Trp Thr Leu Ala Glu Val Glu Ser Ile Tyr Pro Val Pro Lys Ile Lys
                165                 170                 175

Arg Tyr Gly Val Leu Glu Ile Gln Thr Met Asp Phe His Gly Ser Tyr
            180                 185                 190

Lys His Ala Val Gly Ala Ile Asp Ile Ala Leu Val Glu Gly Ile Asp
        195                 200                 205

Phe His Gly Trp Leu Pro Thr Pro Ala Gly Arg Ala Ala Leu Ser Lys
    210                 215                 220

Lys Met Glu Gly Pro Asn Leu Ser Asn Val Phe Lys Arg Thr Phe Tyr
225                 230                 235                 240

Gln Met Ala Tyr Lys Phe Ala Leu Ser Gly His Gln Arg Cys Ala Gly
                245                 250                 255

```
Thr Gly Phe Ala Ile Pro Gln Ser Val Trp Lys Ser Trp Leu Arg His
            260                 265                 270

Leu Ala Asn Pro Thr Leu Ile Asp Asn Gly Asp Gly Thr Phe Ser Leu
            275                 280                 285

Gly Asp Thr Arg Asn Asp Ser Glu Asn Ala Trp Ile Phe Val Phe Glu
            290                 295                 300

Leu Asp Pro Asp Thr Asp Ala Ser Pro Arg Pro Leu Ala Pro His Leu
305                 310                 315                 320

Glu Ile Arg Val Asn Val Asp Thr Leu Ile Asp Leu Ala Leu Arg Glu
                325                 330                 335

Ser Pro Arg Ala Ala Leu Gly Pro Ser Gly Pro Val Ala Thr Phe Thr
            340                 345                 350

Asp Lys Val Glu Ala Arg Met Leu Arg Phe Trp Pro Lys Thr Arg Arg
            355                 360                 365

Arg Arg Ser Thr Thr Pro Gly Gly Gln Arg Gly Leu Phe Asp Ala
            370                 375                 380

<210> SEQ ID NO 91
<211> LENGTH: 326
<212> TYPE: PRT
<213> ORGANISM: Providencia stuartii 164

<400> SEQUENCE: 91

Met Lys Glu Leu Lys Leu Lys Glu Ala Lys Glu Ile Leu Lys Ala Leu
1               5                   10                  15

Gly Leu Pro Pro Gln Gln Tyr Asn Asp Arg Ser Gly Trp Val Leu Leu
            20                  25                  30

Ala Leu Ala Asn Ile Lys Pro Glu Asp Ser Trp Lys Glu Ala Lys Ala
            35                  40                  45

Pro Leu Leu Pro Thr Val Ser Ile Met Glu Phe Ile Arg Thr Glu Tyr
    50                  55                  60

Gly Lys Asp Tyr Lys Pro Asn Ser Arg Glu Thr Ile Arg Arg Gln Thr
65                  70                  75                  80

Leu His Gln Phe Glu Gln Ala Arg Ile Val Asp Arg Asn Arg Asp Leu
                85                  90                  95

Pro Ser Arg Ala Thr Asn Ser Lys Asp Asn Asn Tyr Ser Leu Asn Gln
            100                 105                 110

Val Ile Ile Asp Ile Leu His Asn Tyr Pro Asn Gly Asn Trp Lys Glu
            115                 120                 125

Leu Ile Gln Gln Phe Leu Thr His Val Pro Ser Leu Gln Glu Leu Tyr
    130                 135                 140

Glu Arg Ala Leu Ala Arg Asp Arg Ile Pro Ile Lys Leu Leu Asp Gly
145                 150                 155                 160

Thr Gln Ile Ser Leu Ser Pro Gly Glu His Asn Gln Leu His Ala Asp
                165                 170                 175

Ile Val His Glu Phe Cys Pro Arg Phe Val Gly Asp Met Gly Lys Ile
            180                 185                 190

Leu Tyr Ile Gly Asp Thr Ala Ser Ser Arg Asn Glu Gly Gly Lys Leu
            195                 200                 205

Met Val Leu Asp Ser Glu Tyr Leu Lys Lys Leu Gly Val Pro Pro Met
    210                 215                 220

Ser His Asp Lys Leu Pro Asp Val Val Tyr Asp Glu Lys Arg Lys
225                 230                 235                 240

Trp Leu Phe Leu Ile Glu Ala Val Thr Ser His Gly Pro Ile Ser Pro
```

```
              245                 250                 255
Lys Arg Trp Leu Glu Leu Glu Ala Ala Leu Ser Ser Cys Thr Val Gly
            260                 265                 270

Lys Val Tyr Val Thr Ala Phe Pro Thr Arg Thr Glu Phe Arg Lys Asn
            275                 280                 285

Ala Ala Asn Ile Ala Trp Glu Thr Glu Val Trp Ile Ala Asp Asn Pro
        290                 295                 300

Asp His Met Val His Phe Asn Gly Asp Arg Phe Leu Gly Pro His Asp
305                 310                 315                 320

Lys Lys Pro Glu Leu Ser
                325

<210> SEQ ID NO 92
<211> LENGTH: 157
<212> TYPE: PRT
<213> ORGANISM: Proteus vulgaris

<400> SEQUENCE: 92

Met Ser His Pro Asp Leu Asn Lys Leu Leu Glu Leu Trp Pro His Ile
1               5                   10                  15

Gln Glu Tyr Gln Asp Leu Ala Leu Lys His Gly Ile Asn Asp Ile Phe
            20                  25                  30

Gln Asp Asn Gly Gly Lys Leu Leu Gln Val Leu Leu Ile Thr Gly Leu
        35                  40                  45

Thr Val Leu Pro Gly Arg Glu Gly Asn Asp Ala Val Asp Asn Ala Gly
    50                  55                  60

Gln Glu Tyr Glu Leu Lys Ser Ile Asn Ile Asp Leu Thr Lys Gly Phe
65                  70                  75                  80

Ser Thr His His His Met Asn Pro Val Ile Ile Ala Lys Tyr Arg Gln
                85                  90                  95

Val Pro Trp Ile Phe Ala Ile Tyr Arg Gly Ile Ala Ile Glu Ala Ile
            100                 105                 110

Tyr Arg Leu Glu Pro Lys Asp Leu Glu Phe Tyr Tyr Asp Lys Trp Glu
        115                 120                 125

Arg Lys Trp Tyr Ser Asp Gly His Lys Asp Ile Asn Asn Pro Lys Ile
    130                 135                 140

Pro Val Lys Tyr Val Met Glu His Gly Thr Lys Ile Tyr
145                 150                 155

<210> SEQ ID NO 93
<211> LENGTH: 358
<212> TYPE: PRT
<213> ORGANISM: Streptomyces achromogenes

<400> SEQUENCE: 93

Met Gly Ile Thr Ile Lys Lys Ser Thr Ala Glu Gln Val Leu Arg Lys
1               5                   10                  15

Ala Tyr Glu Ala Ala Ala Ser Asp Asp Val Phe Leu Glu Asp Trp Ile
            20                  25                  30

Phe Leu Ala Thr Ser Leu Arg Glu Val Asp Ala Pro Arg Thr Tyr Thr
        35                  40                  45

Ala Ala Leu Val Thr Ala Leu Leu Ala Arg Ala Cys Asp Asp Arg Val
    50                  55                  60

Asp Pro Arg Ser Ile Lys Glu Lys Tyr Asp Asp Arg Ala Phe Ser Leu
65                  70                  75                  80

Arg Thr Leu Cys His Gly Val Val Val Pro Met Ser Val Glu Leu Gly
```

```
            85                  90                  95
Phe Asp Leu Gly Ala Thr Gly Arg Glu Pro Ile Asn Asn Gln Pro Phe
            100                 105                 110
Phe Arg Tyr Asp Gln Tyr Ser Glu Ile Val Arg Val Gln Thr Lys Ala
            115                 120                 125
Arg Pro Tyr Leu Asp Arg Val Ser Ser Ala Leu Ala Arg Val Asp Glu
        130                 135                 140
Glu Asp Tyr Ser Thr Glu Glu Ser Phe Arg Ala Leu Val Ala Val Leu
145                 150                 155                 160
Ala Val Cys Ile Ser Val Ala Asn Lys Lys Gln Arg Val Ala Val Gly
                165                 170                 175
Ser Ala Ile Val Glu Ala Ser Leu Ile Ala Glu Thr Gln Ser Phe Val
                180                 185                 190
Val Ser Gly His Asp Val Pro Arg Lys Leu Gln Ala Cys Val Ala Ala
                195                 200                 205
Gly Leu Asp Met Val Tyr Ser Glu Val Val Ser Arg Arg Ile Asn Asp
        210                 215                 220
Pro Ser Arg Asp Phe Pro Gly Asp Val Gln Val Ile Leu Asp Gly Asp
225                 230                 235                 240
Pro Leu Leu Thr Val Glu Val Arg Gly Lys Ser Val Ser Trp Glu Gly
                245                 250                 255
Leu Glu Gln Phe Val Ser Ser Ala Thr Tyr Ala Gly Phe Arg Arg Val
                260                 265                 270
Ala Leu Met Val Asp Ala Ala Ser His Val Ser Leu Met Ser Ala Asp
                275                 280                 285
Asp Leu Thr Ser Ala Leu Glu Arg Lys Tyr Glu Cys Ile Val Lys Val
        290                 295                 300
Asn Glu Ser Val Ser Ser Phe Leu Arg Asp Val Phe Val Trp Ser Pro
305                 310                 315                 320
Arg Asp Val His Ser Ile Leu Ser Ala Phe Pro Glu Ala Met Tyr Arg
                325                 330                 335
Arg Met Ile Glu Ile Glu Val Arg Glu Pro Glu Leu Asp Arg Trp Ala
                340                 345                 350
Glu Ile Phe Pro Glu Thr
        355

<210> SEQ ID NO 94
<211> LENGTH: 315
<212> TYPE: PRT
<213> ORGANISM: Streptomyces albus G

<400> SEQUENCE: 94

Met Ile Asn Ala Asp Lys Pro His Arg Trp Asn Asp Asp Val Gln Ala
1               5                   10                  15
Ser Val Arg Leu Tyr Asn Gln Trp Phe Leu Asp Ala Pro Lys Ala
                20                  25                  30
Tyr Arg Asp Thr Arg Gln Leu Thr Ile Asp Glu Val Glu Gln Ala Phe
            35                  40                  45
Gln Arg Thr Ala Asn Met Thr Ser Ile Thr Pro Glu Val Leu Lys Ala
        50                  55                  60
His Pro Lys Thr Leu Ala Thr Leu Arg Met Ser Thr Ala Pro Pro Ile
65                  70                  75                  80
Ala Arg Asp Arg Leu Val Gly Leu Ser His Gly Ser Lys Ser Leu Leu
                85                  90                  95
```

```
Asp Thr Met Glu Lys Gly Lys Leu Pro Pro Arg Met Lys Gly Asp Val
            100                 105                 110

Leu Asp Thr His Leu Ala Lys Met Cys Ala Val Leu Thr Asp Leu Leu
        115                 120                 125

Asp Leu Asp Leu Phe His Trp Tyr Pro Thr Gly Glu Pro Ala Glu Pro
    130                 135                 140

Arg Gln Arg Glu Leu Ala Ala Thr Val Val Ala Asp Arg Leu Cys Gly
145                 150                 155                 160

Ala Ile Ala Asp Pro Ile Val Arg Asn Ala Gln Glu Arg Arg Gln Leu
                165                 170                 175

Ala Leu Ile Glu Glu Trp Leu Leu Ala Arg Gly Tyr Thr Lys Lys Thr
            180                 185                 190

His Ser Ala Ser Leu Pro Leu Asn Thr Met Gln Pro Gly Thr Phe Ser
        195                 200                 205

Phe Arg Gln Asn Val Val Gly Ser Asp Leu Pro Val Asn Ile Pro
    210                 215                 220

Val Asp Ala Val Ile Gln Pro His Thr Pro His Ser His Lys Leu Pro
225                 230                 235                 240

Ile Leu Ile Glu Ala Lys Ser Ala Gly Asp Phe Thr Asn Thr Asn Lys
                245                 250                 255

Arg Arg Lys Glu Glu Ala Thr Lys Ile His Gln Leu Gln Leu Lys Tyr
            260                 265                 270

Gly Asn Glu Ile Ser Leu Thr Leu Phe Leu Cys Gly Tyr Phe Asn Thr
        275                 280                 285

Gly Tyr Leu Gly Tyr Ser Ala Ala Glu Gly Leu Asp Trp Val Trp Glu
    290                 295                 300

His Arg Ile Asp Asp Leu Glu Ala Ala Gly Ala
305                 310                 315

<210> SEQ ID NO 95
<211> LENGTH: 432
<212> TYPE: PRT
<213> ORGANISM: Saccharopolyspora sp.

<400> SEQUENCE: 95

Met Arg Arg Leu Ala Thr Gln Arg Arg Glu Asp Ala Tyr Lys Ser Asn
1               5                   10                  15

Arg Asp Tyr Gln Thr Val His Glu Ala Gln Ser Leu Arg Val Asn Ser
            20                  25                  30

Thr Asp Asp Asn Leu Ser Leu Phe Leu Lys Asp Ile Ser Pro
        35                  40                  45

Arg Glu Asp Ser Lys Asn Ile Val Gly Phe Gly Phe Val Lys Pro
50                  55                  60

Glu Ile Ala Thr Thr Met Ala Leu Thr Leu Thr Thr Asp Ile Asp Lys
65                  70                  75                  80

Gln Ile Lys Ser Val Pro Leu Ser Ser Asn Trp Asn Arg Ile Ser Ile
                85                  90                  95

Val Ala Lys Phe Ala Ser Asn Pro Ser Val Ser Ile Thr Leu Gly Phe
            100                 105                 110

Asp Gln Thr Pro Trp Val Asp Phe Trp Gly Ile Asn Ser Asp Ile
        115                 120                 125

Gly Leu Ser Phe Val Ser Asp Ala Val Pro Leu Glu Met Ser Met Ile
    130                 135                 140

Asp Ser Ile His Ile Ala Pro Glu Thr Leu Tyr Leu Asp His Ser Ser
145                 150                 155                 160
```

```
Ala Cys Leu Leu Asp Ile Asp Pro Val Glu Ser Thr Arg Phe Lys Thr
                165                 170                 175

Gly His Gly Asp Pro Leu Ser Leu Lys Lys Cys Ser Tyr Cys Gly Arg
            180                 185                 190

Leu Leu Pro Ile Asp Leu Glu Arg Pro Gly Lys Leu Ser Phe His Lys
        195                 200                 205

His Arg Ala Lys Ile Thr Asn His Gln Asn Glu Cys Arg Ser Cys Lys
    210                 215                 220

Lys Trp Arg Ile Asn Asn Ser Phe Asn Pro Met Arg Thr Ile Asp Gln
225                 230                 235                 240

Leu Asn Glu Ser Ala Leu Ile Thr Arg Glu Arg Lys Ile Phe Leu Gln
                245                 250                 255

Glu Pro Glu Ile Leu Gln Glu Ile Lys Asp Arg Thr Gly Ala Gly Leu
            260                 265                 270

Lys Ser Gln Val Trp Glu Arg Phe His Arg Lys Cys Phe Asn Cys Arg
        275                 280                 285

Lys Asp Leu Lys Leu Ser Glu Val Gln Leu Asp His Thr Arg Pro Leu
    290                 295                 300

Ala Tyr Leu Trp Pro Ile Asp Glu His Ala Thr Cys Leu Cys Ala Gln
305                 310                 315                 320

Cys Asn Asn Thr Lys Lys Asp Arg Phe Pro Val Asp Phe Tyr Ser Glu
                325                 330                 335

Gln Gln Ile Arg Glu Leu Ser Asp Ile Cys Gly Leu Pro Tyr Gln Asp
            340                 345                 350

Leu Cys Ala Arg Ser Leu Asn Leu Asp Gln Leu Asp Arg Ile Glu Arg
        355                 360                 365

Asn Ile Ala Glu Phe Ser Lys Glu Trp Asp Val Arg Thr Phe Ala Ser
    370                 375                 380

Thr Ala Arg Arg Ile Ser Glu Val Tyr Pro Ala Arg Asp Leu Phe Glu
385                 390                 395                 400

Thr Leu Lys Lys Glu Ser Glu Ser Ala Tyr Asn Lys Ile Ile Glu Lys
                405                 410                 415

Leu Lys Glu Arg Pro Asp Ala Leu Leu Asp Glu Ala Leu Pro Leu Asp
            420                 425                 430

<210> SEQ ID NO 96
<211> LENGTH: 323
<212> TYPE: PRT
<213> ORGANISM: Streptomyces species Bf-61

<400> SEQUENCE: 96

Met Asn Ser Ser Asp Gly Ile Asp Gly Thr Val Ala Ser Ile Asp Thr
1               5                   10                  15

Ala Arg Ala Leu Leu Lys Arg Phe Gly Phe Asp Ala Gln Arg Tyr Asn
                20                  25                  30

Val Arg Ser Ala Val Thr Leu Leu Ala Leu Ala Gly Leu Lys Pro Gly
            35                  40                  45

Asp Arg Trp Val Asp Ser Thr Thr Pro Arg Leu Gly Val Gln Lys Ile
        50                  55                  60

Met Asp Trp Ser Gly Glu His Trp Ala Lys Pro Tyr Ala Thr Gly Ser
65                  70                  75                  80

Arg Glu Asp Phe Arg Lys Lys Thr Leu Arg Gln Trp Val Asp Asn Gly
                85                  90                  95

Phe Ala Val Leu Asn Ala Asp Asn Leu Asn Ile Ala Thr Asn Ser Gln
```

```
                  100                 105                 110
Leu Asn Glu Tyr Cys Leu Ser Asp Glu Ala Leu Gln Ala Leu Arg Ala
            115                 120                 125

Tyr Gly Thr Glu Gly Phe Glu Glu Ser Leu Val Val Phe Leu Asp Glu
    130                 135                 140

Ala Ser Lys Ala Val Lys Ala Arg Ala Glu Ala Leu Gln Ala Ala Met
145                 150                 155                 160

Ile Ser Val Asp Leu Pro Gly Gly Glu Glu Phe Leu Leu Ser Pro Ala
                165                 170                 175

Gly Gln Asn Pro Leu Leu Lys Lys Met Val Glu Glu Phe Val Pro Arg
            180                 185                 190

Phe Ala Pro Arg Ser Thr Val Leu Tyr Leu Gly Asp Thr Arg Gly Lys
        195                 200                 205

His Ser Leu Phe Glu Arg Glu Ile Phe Glu Glu Val Leu Gly Leu Thr
    210                 215                 220

Phe Asp Pro His Gly Arg Met Pro Asp Leu Ile Leu His Asp Glu Val
225                 230                 235                 240

Arg Gly Trp Leu Phe Leu Met Glu Ala Val Lys Ser Lys Gly Pro Phe
                245                 250                 255

Asp Glu Glu Arg His Arg Ser Leu Gln Glu Leu Phe Val Thr Pro Ser
            260                 265                 270

Ala Gly Leu Ile Phe Val Asn Cys Phe Glu Asn Arg Glu Ser Met Arg
        275                 280                 285

Gln Trp Leu Pro Glu Leu Ala Trp Glu Thr Glu Ala Trp Val Ala Glu
    290                 295                 300

Asp Pro Asp His Leu Ile His Leu Asn Gly Ser Arg Phe Leu Gly Pro
305                 310                 315                 320

Tyr Glu Arg

<210> SEQ ID NO 97
<211> LENGTH: 227
<212> TYPE: PRT
<213> ORGANISM: Streptomyces caespitosus

<400> SEQUENCE: 97

Met Ile Asn Asp Gln Leu Pro Arg Trp Val Arg Glu Ala Arg Val Gly
1               5                   10                  15

Thr Arg Thr Gly Gly Pro Ala Met Arg Pro Lys Thr Ser Asp Ser Pro
            20                  25                  30

Tyr Phe Gly Trp Asp Ser Glu Asp Trp Pro Glu Val Thr Arg Gln Leu
        35                  40                  45

Leu Ser Glu Gln Pro Leu Ser Gly Asp Thr Leu Val Asp Ala Val Leu
    50                  55                  60

Ala Ser Trp Glu Ser Ile Phe Glu Ser Arg Leu Gly Ser Gly Phe His
65                  70                  75                  80

Ile Gly Thr Gln Ile Arg Pro Thr Pro Gln Ile Met Gly Phe Leu Leu
                85                  90                  95

His Ala Leu Ile Pro Leu Glu Leu Ala Asn Gly Asp Pro Ser Trp Arg
            100                 105                 110

Ala Asp Leu Asn Ser Ser Glu Lys Asp Leu Val Tyr Gln Pro Asp His
        115                 120                 125

Lys Tyr Ser Ile Glu Met Lys Thr Ser Ser His Lys Asp Gln Ile Phe
    130                 135                 140

Gly Asn Arg Ser Phe Gly Val Glu Asn Pro Gly Lys Gly Lys Lys Ala
```

```
                145                 150                 155                 160
Lys Asp Gly Tyr Tyr Val Ala Val Asn Phe Glu Lys Trp Ser Asp Ala
                    165                 170                 175

Pro Gly Arg Leu Pro Arg Ile Arg Thr Ile Arg Tyr Gly Trp Leu Asp
                180                 185                 190

His Thr Asp Trp Val Ala Gln Lys Ser Gln Thr Gly Gln Gln Ser Ser
            195                 200                 205

Leu Pro Ala Val Val Ser Asn Thr Gln Leu Leu Ala Ile His Thr Gly
        210                 215                 220

Gly Gln Arg
225

<210> SEQ ID NO 98
<211> LENGTH: 235
<212> TYPE: PRT
<213> ORGANISM: Streptomyces phaeochromogenes

<400> SEQUENCE: 98

Met Thr Ser Lys Asp Pro Ile Val Leu Ser Ala Asp Gln Ile Ala Trp
1               5                   10                  15

Leu Arg Gln Leu Lys Met Ser Lys Arg Ala Ala Leu Val Arg Asp Tyr
            20                  25                  30

Ile Leu Glu Tyr Gly Ala Val Thr Thr Gly Lys Leu Ala Glu Leu Gly
        35                  40                  45

Tyr Ser His Pro Pro Arg Ala Ala Arg Asp Leu Lys Asp Ala Gly Ala
    50                  55                  60

Gly Val Val Thr Ile Met Val Lys Gly Pro Asp Gly Arg Arg Met Ala
65                  70                  75                  80

Ser Tyr Ala Phe Asn Gly Lys Ala Asn Glu Asp Gly Ala Gly Arg Val
                85                  90                  95

Val Ile Pro Lys Ala Phe Gly Glu Ala Leu Lys Arg Ala His Gly Gly
            100                 105                 110

Lys Cys Ala Val Cys Tyr Gly Asp Phe Ser Glu Arg Glu Leu Gln Cys
        115                 120                 125

Asp His Arg Val Pro Phe Ala Ile Ala Gly Asp Lys Pro Lys Leu Val
    130                 135                 140

Gln Glu Asp Phe Met Pro Leu Cys Ala Ser Asp Asn Arg Ala Lys Ser
145                 150                 155                 160

Trp Ser Cys Glu Asn Cys Pro Asn Trp Glu Leu Lys Asp Glu Asp Thr
                165                 170                 175

Cys Arg Ser Cys Phe Trp Ala Ser Pro Glu Asn Tyr Thr His Val Ser
            180                 185                 190

Thr Arg Pro Glu Arg Arg Ile Asn Leu Leu Phe Gln Gly Asp Glu Val
        195                 200                 205

Glu Ile Phe Asp Ala Leu Lys Asn Ala Ala Asn Glu Gly Val Ser
    210                 215                 220

Leu Thr Glu Ala Thr Lys Arg Lys Leu Ala Asp
225                 230                 235

<210> SEQ ID NO 99
<211> LENGTH: 281
<212> TYPE: PRT
<213> ORGANISM: Sphaerotilus species

<400> SEQUENCE: 99

Met Ser Lys Ala Ala Tyr Gln Asp Phe Thr Lys Arg Phe Ser Leu Leu
```

```
              1               5              10              15
Ile Lys Lys His Pro Asn Leu Ile Thr Met Thr Leu Ser Asn Ile Phe
                 20                  25                  30
Thr Met Arg Leu Ile Gly Asn Lys Thr His Gly Asp Leu Ala Glu Ile
                 35                  40                  45
Ala Ile Ser Glu Phe Ile Asn Gln Tyr Met Tyr Asp Phe Lys Ser Ile
             50                  55                  60
His Val Gly Lys Asp Leu Tyr Arg Ala Lys Ser Lys Glu Glu Asp Ile
 65                  70                  75                  80
Thr Val Glu Asn Glu Ile Thr Lys Glu Lys Phe Pro Ile Ser Leu Lys
                 85                  90                  95
Ala Tyr Gly Asp Gly Pro Leu Gln Leu Ser Thr Asp Lys Asn Phe Leu
                100                 105                 110
Met Tyr Pro Leu Leu Glu Glu Ile Gly Ala Phe Ile Asn Ala Lys Glu
                115                 120                 125
Lys Ile Glu Glu Ile Phe Ala Asn Glu Ala Phe Ser Cys Phe Ser Glu
            130                 135                 140
Ile Asn Val Leu Pro Leu Ile Tyr Asp Glu Lys Arg Gln Arg Cys Asn
145                 150                 155                 160
Ile Leu Val Phe Asp Ala Ala Arg Ala Arg Ala Glu Thr Ala Tyr Ile
                165                 170                 175
Arg Lys Glu Thr Glu Gly Ser Gly Arg Lys His Pro Ala Tyr Arg Phe
                180                 185                 190
Phe Asp Lys Asn Lys Asn Tyr Ile Cys Glu Val Arg Tyr Gly Asn Ala
                195                 200                 205
Ala Ala Asn Ala Leu Gln Arg Gly Leu Trp Thr Asn Thr Lys Asn Ala
            210                 215                 220
Thr Ser Phe Phe Asp Ser Val Thr Asn Gly Trp Val Asp Tyr Ser His
225                 230                 235                 240
Asn Leu Val Leu Val Lys Leu Leu Ser His Ala Leu Val Ser Ser Arg
                245                 250                 255
Lys Gly His Glu Ala Ala Leu Glu Glu Ile Lys Lys Asp Ile Leu Gln
            260                 265                 270
Leu Lys Gln Thr Asn Gly Ile Asn Val
            275                 280

<210> SEQ ID NO 100
<211> LENGTH: 1077
<212> TYPE: DNA
<213> ORGANISM: Anabaena variabilis

<400> SEQUENCE: 100
atggaagaag accttgattt atctgaaaat atcgaagctg catctgcgga gcttacgact      60
ctttatcagg tagctgctga tgctatgaaa gattatattg aaatctatct tgcgctgagt     120
aaacagtctg atgggttttc aaatattaac aatcttgact taacttctcg taacaggcgt     180
ttggtagtta tacatggact ttcgttagag ttagatccag atacttcgac tccagaggaa     240
attaaacgtg aagctgaacg aatgctagcg atagctcttg atacagagtc agcaattacg     300
gcaggagtat atgaaaaaat gcgtctcttc gcaagctctt tagtagatca gctatttgaa     360
caaacggatg aacttaattc attatcatcg gaatatttgt cagcaaatcc aggattttg      420 ccgttttccc agcagttggc ggggcttaga agtaaatcag agttaaagag agaagtagga     480
aatgcctctg acaatagtat ttctaaagcg gttgcagaga gaatattaga gcgcattata     540
```

-continued

```
cgtaacttga gaattcgcac tttttccaaa gagaaactat tacaagctgt tgagcctact    600
ttagaaggaa tagtcaggga tctcgtagga aaagtgttat tggaaaatat agttgctgat    660
gctttatctg atttacaagt tcctttcatg cgtgaatcag agtatcaaag ccttaaagga    720
gtgatttatg atttccgcgc tgattttgtg ataccagacg cacaaaatcc aattgctttt    780
atcgaggtgc gaaaaagctc tacacgacat gcgtcactct atgccaagga taagatgttt    840
tcagcgatta attggaaagg aaaaaataaa aggcttttgg gtattttggt tgtggaagga    900
ccttggacaa gagaaactct tcgcgtcatg gcaaatgtgt ttgattacgt tacaccttta    960
actcgtgttt cccaagttgc agaagctatc agagcatatc tagatgggga taaaacgaga   1020
ctgaagtggt tagttaattt cagtattgaa gaagcagacc acgacaacat aacctaa      1077
```

<210> SEQ ID NO 101
<211> LENGTH: 1293
<212> TYPE: DNA
<213> ORGANISM: Bacillus sphaericus

<400> SEQUENCE: 101

```
atgagacgat tagcaaaaaa ttcacggaac gacagttatt taagtaatag ggattaccag     60
gaaatcgtga gggaaaatac cactacaata tcgtttccct taaaagaaaa acatactctg    120
actttaacga aaaaaatagg gctaaatcag actgctggat tcggaggatg gtttttccct    180
gattcaccat gtttattaac agtaactgta ctatcctctt tcggtacaaa ggtaacttct    240
aaaaccttta gcctttctaa agattggaat cgtgttgggc ttgcttggat taacgagcat    300
tcgagtgaca ccataagcat tgtcctagag tttagtgatg tggaaatagt tcatacatgg    360
ggacttacat gtgatgtttt taatgtccat gaattaatta ttgatgctat agaagatcaa    420
aataaactaa tagacgtgct aaatcaagaa catttatctc ctgaaacata ttatttaaac    480
catgactctg atactgattt aattgagaat ttggaatcta cagaagagat aaagatagtt    540
aaccaaagcc aaaagcaaat ctctttaaaa aaatgctgtt attgtcaacg ttatatgcct    600
gtgaacatat tagttcgttc aaattcatca tttcataaac acaagagtaa gaaaactggt    660
tttcaaaatg aatgtcgggc ttgtaagaag tggagaataa ataattcatt caatccagtc    720
agaacaaaag accaactaca tgaatcagca gttattacac gtgaaaaaaa aatattactt    780
aaagaacctg aaatattaca gaaaatcaaa aatagaaata acggtgaggg cttaaaaagt    840
attatatgga aaaaatttga taaaaaatgc tttaattgtg aaaaagaatt aaccattgaa    900
gaggtacgcc tagaccatac aagaccactt gcttatctgt ggcctatcga tgaacacgca    960
acttgtttat gtgaaaaatg caacaataca aaacatgata tgtttcctat cgatttttat   1020
caaggggacg aagacaaatt aagacgttta gctagaatta cggggttaga ttatgaatct   1080
ctagttaaga gggacgtaaa tgaagttgaa cttgcaagaa taatcaataa cattgaagac   1140
tttgcaacta atgtagaggc acgtactttt cgctcaataa gaaataaagt aaaagaagta   1200
cgtcccgata ctgacctatt tgaaattctt aaatctaaaa atattaattt atataatgaa   1260
cttcaatatg aacttcttac ccgtaaggat taa                                 1293
```

<210> SEQ ID NO 102
<211> LENGTH: 2189
<212> TYPE: DNA
<213> ORGANISM: artificial
<220> FEATURE:
<223> OTHER INFORMATION: plasmid placzz2

<400> SEQUENCE: 102

```
ctggcgaaag ggggatgtgc tgcaaggcga ttaagttggg taacgccagg gttttcccag      60
tcacgacgtt gtaaaacgac ggccagtgaa ttcgagctcg gtacccgggg gcgcgccgga     120
tccttaatta agtctagagt cgactgttta aacctgcagg catgcaagct tggcgtaatc     180
atggtcatat gttaacctcc ggcgtaatca tggtcatagc tgtttcctgt gtgaaattgt     240
tatccgctca caattccaca acatacga gccggaagca taaagtgtaa agcctggggt       300
gcctaatgag tgagctaact cacattaatt gcgttgcgct cactgcccgc tttccagtcg     360
ggaaacctgt cgtgccagca tgtgagcaaa aggccagcaa aaggccagga accgtaaaaa     420
ggccgcgttg ctggcgtttt tccataggct ccgcccccct gacgagcatc acaaaaatcg     480
acgctcaagt cagaggtggc gaaacccgac aggactataa agataccagg cgtttccccc     540
tggaagctcc ctcgtgcgct ctcctgttcc gaccctgccg cttaccggat acctgtccgc     600
ctttctccct tcgggaagcg tggcgctttc tcatagctca cgctgtaggt atctcagttc     660
ggtgtaggtc gttcgctcca agctgggctg tgtgcacgaa ccccccgttc agcccgaccg     720
ctgcgcctta tccggtaact atcgtcttga gtccaacccg gtaagacacg acttatcgcc     780
actggcagca gccactggta acaggattag cagagcgagg tatgtaggcg gtgctacaga     840
gttcttgaag tggtggccta actacggcta cactagaagg acagtatttg gtatctgcgc     900
tctgctgaag ccagttacct tcggaaaaag agttggtagc tcttgatccg gcaaacaaac     960
caccgctggt agcggtggtt tttttgtttg caagcagcag attacgcgca gaaaaaagg    1020
atctcaagaa gatcctttga tcttttctac ggggtctgac gctcagtgga acgaaaactc    1080
acgttaaggg attttggtca tgagattatc aaaaaggatc ttcacctaga tccttttaaa    1140
ttaaaaatga agttttaaat caatctaaag tatatatgag taaacttggt ctgacagtta    1200
ccaatgctta atcagtgagg cacctatctc agcgatctgt ctatttcgtt catccatagt    1260
tgcctgactc cccgtcgtgt agataactac gatacgggag gcttaccat ctggccccag     1320
tgctgcaatg ataccgcgag acccacgctc accggctcca gatttatcag caataaacca    1380
gccagccgga agggccgagc gcagaagtgg tcctgcaact ttatccgcct ccatccagtc    1440
tattaattgt tgccgggaag ctagagtaag tagttcgcca gttaatagtt tgcgcaacgt    1500
tgttgccatt gctacaggca tcgtggtgtc acgctcgtcg tttggtatgg cttcattcag    1560
ctccggttcc caacgatcaa ggcgagttac atgatccccc atgttgtgca aaaaagcggt    1620
tagctccttc ggtcctccga tcgttgtcag aagtaagttg gccgcagtgt tatcactcat    1680
ggttatggca gcactgcata attctcttac tgtcatgcca tccgtaagat gcttttctgt    1740
gactggtgag tactcaacca agtcattctg agaatagtgt atgcggcgac cgagttgctc    1800
ttgcccggcg tcaatacggg ataataccgc gccacatagc agaactttaa aagtgctcat    1860
cattggaaaa cgttcttcgg ggcgaaaact ctcaaggatc ttaccgctgt tgagatccag    1920
ttcgatgtaa cccactcgtg cacccaactg atcttcagca tcttttactt tcaccagcgt    1980
ttctgggtga gcaaaaacag gaaggcaaaa tgccgcaaaa aagggaataa gggcgacacg    2040
gaaatgttga atactcatac tcttcctttt tcaatattat tgaagcattt atcagggtta    2100
ttgtctcatg agcggataca tatttgaatg tatttagaaa aataaacaaa taggggttcc    2160
gcgcacattt ccccgaaaag tgccacctg                                      2189
```

<210> SEQ ID NO 103
<211> LENGTH: 10673
<212> TYPE: DNA

<213> ORGANISM: artificial
<220> FEATURE:
<223> OTHER INFORMATION: plasmid pBC4

<400> SEQUENCE: 103

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctctagagt cgaaccccgg atccggccgt ccgccgtgat ccatgcggtt accgcccgcg     480
tgtcgaaccc aggtgtgcga cgtcagacaa cggggagcg ctccttttgg cttccttcca     540
ggcgcggcgg ctgctgcgct agcttttttg gccactggcc gcgcgcggcg taagcggtta     600
ggctggaaag cgaaagcatt aagtggctcg ctccctgtag ccggagggtt attttccaag     660
ggttgagtcg caggaccccc ggttcgagtc tcgggccggc cggactgcgg cgaacggggg     720
tttgcctccc cgtcatgcaa gaccccgctt gcaaattcct ccggaaacag ggacgagccc     780
ctttttttgct tttcccagat gcatccggtg ctgcggcaga tgcgcccccc tcctcagcag     840
cggcaagagc aagagcagcg gcagacatgc agggcaccct cccttctcc taccgcgtca     900
ggagggcaa catccgcggc tgacgcgcg gcagatggtg attacgaacc cccgcggcgc     960
cgggcccggc actacctgga cttggaggag ggcgagggcc tggcgcggct aggagcgccc    1020
tctcctgagc gacacccaag ggtgcagctg aagcgtgaca cgcgcgaggc gtacgtgccg    1080
cggcagaacc tgtttcgcga ccgcgaggga gaggagcccg aggagatgcg ggatcgaaag    1140
ttccacgcag ggcgcgagtt gcggcatggc ctgaaccgcg agcggttgct gcgcgaggag    1200
gactttgagc ccgacgcgcg gaccgggatt agtcccgcgc gcgcacacgt ggcggccgcc    1260
gacctggtaa ccgcgtacga gcagacggtg aaccaggaga ttaactttca aaaaagcttt    1320
aacaaccacg tgcgcacgct tgtggcgcgc gaggaggtgg ctataggact gatgcatctg    1380
tgggactttg taagcgcgct ggagcaaaac ccaaatagca agccgctcat ggcgcagctg    1440
ttccttatag tgcagcacag cagggacaac gaggcattca gggatgcgct gctaaacata    1500
gtagagcccg agggccgctg gctgctcgat ttgataaaca ttctgcagag catagtggtg    1560
caggagcgca gcttgagcct ggctgacaag gtggccgcca ttaactattc catgctcagt    1620
ctgggcaagt tttacgcccg caagatatac catacccctt acgttcccat agacaaggag    1680
gtaaagatcg aggggttcta catgcgcatg gcgttgaagg tgcttacctt gagcgacgac    1740
ctgggcgttt atcgcaacga gcgcatccac aaggccgtga gcgtgagccg gcggcgcgag    1800
ctcagcgacc gcgagctgat gcacagcctg caaagggccc tggctggcac gggcagcggc    1860
gatagagagg ccgagtccta ctttgacgcg ggcgctgacc tgcgctgggc cccaagccga    1920
cgcgccctgg aggcagctgg ggccggacct gggctggcgg tggcacccgc gcgcgctggc    1980
aacgtcggcg gcgtggagga atatgacgag gacgatgagt acgagccaga ggacggcgag    2040
tactaagcgg tgatgtttct gatcagatga tgcaagacgc aacggacccg gcggtgcggg    2100
cggcgctgca gagccagccg tccggcctta actccacgga cgactggcgc caggtcatgg    2160
accgcatcat gtcgctgact gcgcgtaacc ctgacgcgtt ccggcagcag ccgcaggcca    2220
```

```
accggctctc cgcaattctg gaagcggtgg tcccggcgcg cgcaaacccc acgcacgaga    2280
aggtgctggc gatcgtaaac gcgctggccg aaaacagggc catccggccc gatgaggccg    2340
gcctggtcta cgacgcgctg cttcagcgcg tggctcgtta caacagcggc aacgtgcaga    2400
ccaacctgga ccggctggtg ggggatgtgc gcgaggccgt ggcgcagcgt gagcgcgcgc    2460
agcagcaggg caacctgggc tccatggttg cactaaacgc cttcctgagt acacagcccg    2520
ccaacgtgcc gcggggacag gaggactaca ccaactttgt gagcgcactg cggctaatgg    2580
tgactgagac accgcaaagt gaggtgtacc agtccgggcc agactatttt ttccagacca    2640
gtagacaagg cctgcagacc gtaaacctga gccaggcttt caagaacttg caggggctgt    2700
gggggggtgcg ggctcccaca ggcgaccgcg cgaccgtgtc tagcttgctg acgcccaact    2760
cgcgcctgtt gctgctgcta atagcgccct tcacggacag tggcagcgtg tcccgggaca    2820
catacctagg tcacttgctg acactgtacc gcgaggccat aggtcaggcg catgtggacg    2880
agcatacttt ccaggagatt acaagtgtca gccgcgcgct ggggcaggag acacgggca    2940
gcctggaggc aaccctgaac tacctgctga ccaaccggcg gcagaagatc ccctcgttgc    3000
acagtttaaa cagcgaggag gagcgcatct tgcgctatgt gcagcagagc gtgagcctta    3060
acctgatgcg cgacggggta acgcccagcg tggcgctgga catgaccgcg cgcaacatgg    3120
aaccgggcat gtatgcctca aaccggccgt ttatcaatcg cctaatggac tacttgcatc    3180
gcgcggccgc cgtgaacccc gagtatttca ccaatgccat cttgaacccg cactggctac    3240
cgccccctgg tttctacacc ggggatttg aggtgcccga gggtaacgat ggattcctct    3300
gggacgacat agacgacagc gtgttttccc cgcaaccgca gaccctgcta gagttgcaac    3360
agcgcgagca ggcagaggcg gcgctgcgaa aggaaagctt ccgcaggcca agcagcttgt    3420
ccgatctagg cgctgcggcc ccgcggtcag atgcgagtag cccatttcca agcttgatag    3480
ggtcttttac cagcactcgc accacccgcc cgcgcctgct gggcgaggag gagtacctaa    3540
acaactcgct gctgcagccg cagcgcgaaa agaacctgcc tccggcattt cccaacaacg    3600
ggatagagag cctagtggac aagatgagta gatggaagac gtatgcgcag gagcacaggg    3660
atgtgcccgg cccgcgcccg cccacccgtc gtcaaaggca cgaccgtcag cggggtctgg    3720
tgtgggagga cgatgactcg gcagacgaca gcagcgtcct ggatttggga gggagtggca    3780
acccgtttgc gcaccttcgc cccaggctgg ggagaatgtt taaaaaaaa aaaaaaaag    3840
catgatgcaa aataaaaaac tcaccaaggc catggcaccg agcgttggtt ttcttgtatt    3900
cccccttagta tgcagcgcgc ggcgatgtat gaggaaggtc ctcctccctc ctacgagagc    3960
gtggtgagcg cggcgccagt ggcggcggcg ctgggttccc ccttcgatgc tcccctggac    4020
ccgccgtttg tgcctccgcg gtacctgcgg cctaccgggg ggagaaacag catccgttac    4080
tctgagttgg cacccctatt cgacaccacc cgtgtgtacc ttgtggacaa caagtcaacg    4140
gatgtggcat ccctgaacta ccagaacgac cacagcaact ttctaaccac ggtcattcaa    4200
aacaatgact acagcccggg ggaggcaagc acacagacca tcaatcttga cgaccgttcg    4260
cactggggcg gcgacctgaa aaccatcctg cataccaaca tgccaaatgt gaacgagttc    4320
atgtttacca ataagtttaa ggcgcggtg atggtgtcgc gctcgcttac taaggacaaa    4380
caggtggagc tgaaatatga gtgggtggag ttcacgctgc ccgagggcaa ctactccgag    4440
accatgacca tagaccttat gaacaacgcg atcgtgagc actacttgaa agtgggcagg    4500
cagaacgggg ttctggaaag cgacatcggg gtaaagtttg acacccgcaa cttcagactg    4560
```

-continued

```
gggtttgacc cagtcactgg tcttgtcatg cctggggtat atacaaacga agccttccat    4620
ccagacatca ttttgctgcc aggatgcggg gtggacttca cccacagccg cctgagcaac    4680
ttgttgggca tccgcaagcg gcaacccttc caggagggct taggatcac ctacgatgac     4740
ctggagggtg gtaacattcc cgcactgttg gatgtggacg cctaccaggc aagcttaaaa    4800
gatgacaccg aacagggcgg ggatggcgca ggcggcggca acaacagtgg cagcggcgcg    4860
gaagagaact ccaacgcggc agccgcggca atgcagccgg tggaggacat gaacgatcat    4920
gccattcgcg gcgacacctt tgccacacgg gcggaggaga agcgcgctga ggccgaggca    4980
gcggcagaag ctgccgcccc cgctgcgcaa cccgaggtcg agaagcctca gaagaaaccg    5040
gtgatcaaac ccctgacaga ggacagcaag aaacgcagtt acaacctaat aagcaatgac    5100
agcaccttca cccagtaccg cagctggtac cttgcataca actacggcga ccctcagacc    5160
gggatccgct catggaccct cctttgcact cctgacgtaa cctgcggctc ggagcaggtc    5220
tactggtcgt tgccagacat gatgcaagac cccgtgacct tccgctccac gagccagatc    5280
agcaactttc cggtggtggg cgccgagctg ttgcccgtgc actccaagag cttctacaac    5340
gaccaggccg tctactccca gctcatccgc cagtttacct ctctgaccca cgtgttcaat    5400
cgctttcccg agaaccagat tttggcgcgc ccgccagccc ccaccatcac caccgtcagt    5460
gaaaacgttc ctgctctcac agatcacggg acgctaccgc tgcgcaacag catcggagga    5520
gtccagcgag tgaccattac tgacgccaga cgccgcacct gccctacgt ttacaaggcc     5580
ctgggcatag tctcgccgcg cgtcctatcg agccgcactt tttgagcaaa catgtccatc    5640
cttatatcgc ccagcaataa cacaggctgg ggcctgcgct tcccaagcaa gatgtttggc    5700
ggggcaaaga agcgctccga ccaacaccca gtgcgcgtgc gcgggcacta ccgcgcgccc    5760
tggggcgcgc acaaacgcgg ccgcactggg cgcaccaccg tcgatgacgc cattgacgcg    5820
gtggtggagg aggcgcgcaa ctacacgccc acgccgccac cagtgtccac agtggacgcg    5880
gccattcaga ccgtggtgcg cggagcccgg cgttatgcta aaatgaagag acggcggagg    5940
cgcgtagcac gtcgccaccg ccgccgaccc ggcactgccg cccaacgcgc ggcggcggcc    6000
ctgcttaacc gcgcacgtcg caccggccga cgggcggcca tgcgggccgc tcgaaggctg    6060
gccgcgggta ttgtcactgt gccccccagg tccaggcgac gagcggccgc cgcagcagcc    6120
gcggccatta gtgctatgac tcagggtcgc aggggcaacg tgtactgggt gcgcgactcg    6180
gttagcggcc tgcgcgtgcc cgtgcgcacc cgccccccgc gcaactagat tgcaagaaaa    6240
aactacttag actcgtactg ttgtatgtat ccagcggcgg cggcgcgcaa cgaagctatg    6300
tccaagcgca aaatcaaaga agagatgctc caggtcatcg cgccggagat ctatggcccc    6360
ccgaagaagg aagagcagga ttacaagccc cgaaagctaa agcgggtcaa aaagaaaaag    6420
aaagatgatg atgatgatga acttgacgac gaggtggaac tgctgcacgc aaccgcgccc    6480
aggcggcggg tacagtggaa aggtcgacgc gtaagacgtg ttttgcgacc cggcaccacc    6540
gtagttttta cgcccggtga gcgctccacc cgcacctaca agcgcgtgta tgatgaggtg    6600
tacggcgacg aggacctgct tgagcaggcc aacgagcgcc tcgggagtt tgcctacgga    6660
aagcggcata aggacatgtt ggcgttgccg ctggacgagg gcaacccaac acctagccta    6720
aagcccgtga cactgcagca ggtgctgccc acgcttgcac cgtccgaaga aaagcgcggc    6780
ctaaagcgcg agtctggtga cttgcaccc accgtgcagc tgatggtacc caagcgccag    6840
cgactggaag atgtcttgga aaaaatgacc gtggagcctg gctggagcc cgaggtccgc    6900
gtgcggccaa tcaagcaggt ggcaccggga ctgggcgtgc agaccgtgga cgttcagata    6960
```

```
cccaccacca gtagcactag tattgccact gccacagagg gcatggagac acaaacgtcc    7020
ccggttgcct cggcggtggc agatgccgcg gtgcaggcgg ccgctgcggc cgcgtccaaa    7080
acctctacgg aggtgcaaac ggacccgtgg atgtttcgcg tttcagcccc ccggcgcccg    7140
cgccgttcca ggaagtacgg caccgccagc gcactactgc ccgaatatgc cctacatcct    7200
tccatcgcgc ctaccccgg ctatcgtggc tacacctacc gccccagaag acgagcgact    7260
acccgacgcc gaaccaccac tggaacccgc cgccgccgtc gccgtcgcca gcccgtgctg    7320
gccccgattt ccgtgcgcag ggtggctcgc gaaggaggca ggaccctggt gctgccaaca    7380
gcgcgctacc accccagcat cgtttaaaag ccggtctttg tggttcttgc agatatggcc    7440
ctcacctgcc gcctccgttt cccggtgccg ggattccgag gaagaatgca ccgtaggagg    7500
ggcatggccg ccacggcct gacgggcgg atgcgtcgtg cgcaccaccg gcggcggcgc    7560
gcgtcgcacc gtcgcatgcg cggcggtatc ctgcccctcc ttattccact gatcgccgcg    7620
gcgattggcg ccgtgcccgg aattgcatcc gtggccttgc aggcgcagag acactgatta    7680
aaaacaagtt gcatgtggaa aaatcaaaat aaaagtctg gagtctcacg ctcgcttggt    7740
cctgtaacta ttttgtagaa tggaagacat caactttgcg tctctggccc cgcgacacgg    7800
ctcgcgcccg ttcatgggaa actggcaaga tatcggcacc agcaatatga gcggtggcgc    7860
cttcagctgg ggctcgctgt ggagcggcat taaaaatttc ggttccacca ttaagaacta    7920
tggcagcaag gcctggaaca gcagcacagg ccagatgctg agggacaagt tgaaagagca    7980
aaatttccaa caaaaggtgg tagatggcct ggcctctggc attagcgggg tggtggacct    8040
ggccaaccag gcagtgcaaa ataagattaa cagtaagctt gatccccgcc ctcccgtaga    8100
ggagcctcca ccggccgtgg agacagtgtc tccagagggg cgtggcgaaa agcgtccgcg    8160
gcccgacagg gaagaaactc tggtgacgca aatagatgag cctccctcgt acgaggaggc    8220
actaaagcaa ggcctgccca ccacccgtcc catcgcgccc atggctaccg gagtgctggg    8280
ccagcacaca cctgtaacgc tggacctgcc tcccccgct gacacccagc agaaacctgt    8340
gctgccaggg ccgtccgccg ttgttgtaac ccgcccctagc cgcgcgtccc tgcgccgtgc    8400
cgccagcggt ccgcgatcga cctgcaggca tgcaagcttg gcgtaatcat ggtcatagct    8460
gtttcctgtg tgaaattgtt atccgctcac aattccacac aacatacgag ccggaagcat    8520
aaagtgtaaa gcctggggtg cctaatgagt gagctaactc acattaattg cgttgcgctc    8580
actgcccgct ttccagtcgg gaaacctgtc gtgccagctg cattaatgaa tcggccaacg    8640
cgcggggaga ggcggtttgc gtattgggcg ctcttccgct tcctcgctca ctgactcgct    8700
gcgctcggtc gttcggctgc ggcgagcggt atcagctcac tcaaaggcgg taatacggtt    8760
atccacagaa tcaggggata acgcaggaaa gaacatgtga gcaaaaggcc agcaaaaggc    8820
caggaaccgt aaaaaggccg cgttgctggc gttttccat aggctccgcc ccctgacga    8880 gcatcacaaa aatcgacgct caagtcagag gtggcgaaac ccgacaggac tataaagata    8940
ccaggcgttt ccccctggaa gctccctcgt gcgctctcct gttccgaccc tgccgcttac    9000
cggatacctg tccgccttc tcccttcggg aagcgtggcg ctttctcaat gctcacgctg    9060
taggtatctc agttcggtgt aggtcgttcg ctccaagctg ggctgtgtgc acgaaccccc    9120
cgttcagccc gaccgctgcg ccttatccgg taactatcgt cttgagtcca acccggtaag    9180
acacgactta tcgccactgg cagcagccac tggtaacagg attagcagag cgaggtatgt    9240
aggcggtgct acagagttct tgaagtggtg gcctaactac ggctacacta aaggacagt    9300
```

```
atttggtatc tgcgctctgc tgaagccagt taccttcgga aaaagagttg gtagctcttg    9360
atccggcaaa caaaccaccg ctggtagcgg tggttttttt gtttgcaagc agcagattac    9420
gcgcagaaaa aaaggatctc aagaagatcc tttgatcttt tctacggggt ctgacgctca    9480
gtggaacgaa aactcacgtt aagggatttt ggtcatgaga ttatcaaaaa ggatcttcac    9540
ctagatcctt ttaaattaaa aatgaagttt taaatcaatc taaagtatat atgagtaaac    9600
ttggtctgac agttaccaat gcttaatcag tgaggcacct atctcagcga tctgtctatt    9660
tcgttcatcc atagttgcct gactccccgt cgtgtagata actacgatac gggagggctt    9720
accatctggc cccagtgctg caatgatacc gcgagaccca cgctcaccgg ctccagattt    9780
atcagcaata aaccagccag ccggaagggc cgagcgcaga agtggtcctg caactttatc    9840
cgcctccatc cagtctatta attgttgccg ggaagctaga gtaagtagtt cgccagttaa    9900
tagtttgcgc aacgttgttg ccattgctac aggcatcgtg gtgtcacgct cgtcgtttgg    9960
tatggcttca ttcagctccg gttcccaacg atcaaggcga gttacatgat cccccatgtt   10020
gtgcaaaaaa gcggttagct ccttcggtcc tccgatcgtt gtcagaagta agttggccgc   10080
agtgttatca ctcatggtta tggcagcact gcataattct cttactgtca tgccatccgt   10140
aagatgcttt tctgtgactg gtgagtactc aaccaagtca ttctgagaat agtgtatgcg   10200
gcgaccgagt tgctcttgcc cggcgtcaat acgggataat accgcgccac atagcagaac   10260
tttaaaagtg ctcatcattg gaaaacgttc ttcggggcga aaactctcaa ggatcttacc   10320
gctgttgaga tccagttcga tgtaacccac tcgtgcaccc aactgatctt cagcatcttt   10380
tactttcacc agcgtttctg ggtgagcaaa aacaggaagg caaaatgccg caaaaaaggg   10440
aataagggcg acacggaaat gttgaatact catactcttc cttttcaat attattgaag   10500
catttatcag ggttattgtc tcatgagcgg atacatattt gaatgtattt agaaaaataa   10560
acaaataggg gttccgcgca catttccccg aaaagtgcca cctgacgtct aagaaaccat   10620
tattatcatg acattaacct ataaaaatag gcgtatcacg aggccctttc gtc          10673
```

<210> SEQ ID NO 104
<211> LENGTH: 22563
<212> TYPE: DNA
<213> ORGANISM: artificial
<220> FEATURE:
<223> OTHER INFORMATION: plasmid pXba

<400> SEQUENCE: 104

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctggc ttaactatgc ggcatcagag cagattgtac tgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
ccttctagac cgtgcaaaag gagagcctgt aagcgggcac tcttccgtgg tctggtggat     480
aaattcgcaa gggtatcatg gcggacgacc ggggttcgaa ccccggatcc ggccgtccgc     540
cgtgatccat gcggttaccg cccgcgtgtc gaacccaggt gtgcgacgtc agacaacggg     600
ggagcgctcc ttttggcttc cttccaggcg cggcggctgc tgcgctagct ttttggcca     660
ctggccgcgc gcggcgtaag cggttaggct ggaaagcgaa agcattaagt ggctcgctcc     720
```

```
ctgtagccgg agggttattt tccaagggtt gagtcgcagg accccggtt cgagtctcgg      780
gccggccgga ctgcggcgaa cggggtttg cctccccgtc atgcaagacc ccgcttgcaa      840
attcctccgg aaacaggac gagccccttt tttgcttttc ccagatgcat ccggtgctgc      900
ggcagatgcg ccccctcct cagcagcggc aagagcaaga gcagcggcag acatgcaggg      960
caccctcccc ttctcctacc gcgtcaggag gggcaacatc cgcggctgac gcggcggcag     1020
atggtgatta cgaaccccg cggcgccggg cccggcacta cctggacttg gaggagggcg     1080
agggcctggc gcggctagga gcgccctctc ctgagcgaca cccaagggtg cagctgaagc     1140
gtgacacgcg cgaggcgtac gtgccgcggc agaacctgtt tcgcgaccgc gagggagagg     1200
agcccgagga gatgcgggat cgaaagttcc acgcagggcg cgagttgcgg catggcctga     1260
accgcgagcg gttgctgcgc gaggaggact ttgagcccga cgcgcggacc gggattagtc     1320
ccgcgcgcgc acacgtggcg gccgccgacc tggtaaccgc gtacgagcag acggtgaacc     1380
aggagattaa ctttcaaaaa agctttaaca accacgtgcg cacgcttgtg gcgcgcgagg     1440
aggtggctat aggactgatg catctgtggg actttgtaag cgcgctggag caaaacccaa     1500
atagcaagcc gctcatggcg cagctgttcc ttatagtgca gcacagcagg acaacgagg     1560
cattcaggga tgcgctgcta aacatagtag agcccgaggg ccgctggctg ctcgatttga     1620
taaacattct gcagagcata gtggtgcagg agcgcagctt gagcctggct gacaaggtgg     1680
ccgccattaa ctattccatg ctcagtctgg gcaagtttta cgcccgcaag atataccata     1740
ccccttacgt tcccatagac aaggaggtaa agatcgaggg gttctacatg cgcatggcgt     1800
tgaaggtgct taccttgagc gacgacctgg gcgtttatcg caacgagcgc atccacaagg     1860
ccgtgagcgt gagccggcgg cgcgagctca gcgaccgcga gctgatgcac agcctgcaaa     1920
gggccctggc tggcacgggc agcggcgata gagaggccga gtcctacttt gacgcgggcg     1980
ctgacctgcg ctgggcccca agccgacgcg ccctggaggc agctggggcc ggacctgggc     2040
tggcggtggc accgcgcgc gctggcaacg tcggcggcgt ggaggaatat gacgaggacg     2100
atgagtacga gccagaggac ggcgagtact aagcggtgat gtttctgatc agatgatgca     2160
agacgcaacg gacccggcgg tgcgggcggc gctgcagagc cagccgtccg gccttaactc     2220
cacggacgac tggcgccagg tcatggaccg catcatgtcg ctgactgcgc gtaaccctga     2280
cgcgttccgg cagcagccgc aggccaaccg gctctccgca attctggaag cggtggtccc     2340
ggcgcgcgca aaccccacgc acgagaaggt gctggcgatc gtaaacgcgc tggccgaaaa     2400
cagggccatc cggcccgatg aggccggcct ggtctacgac gcgctgcttc agcgcgtggc     2460
tcgttacaac agcggcaacg tgcagaccaa cctggaccgg ctggtgggg atgtgcgcga     2520
ggccgtggcg cagcgtgagc gcgcgcagca gcagggcaac ctgggctcca tggttgcact     2580
aaacgccttc ctgagtacac agcccgccaa cgtgccgcgg ggacaggagg actacaccaa     2640
ctttgtgagc gcactgcggc taatggtgac tgagacaccg caaagtgagg tgtaccagtc     2700
cgggccagac tattttttcc agaccagtag acaaggcctg cagaccgtaa acctgagcca     2760
ggctttcaag aacttgcagg ggctgtgggg ggtgcgggct cccacaggcg accgcgcgac     2820
cgtgtctagc ttgctgacgc ccaactcgcg cctgttgctg ctgctaatag cgcccttcac     2880
ggacagtggc agcgtgtccc gggacacata cctaggtcac ttgctgacac tgtaccgcga     2940
ggccataggt caggcgcatg tggacgagca tactttccag gagattacaa gtgtcagcca     3000
cgcgctgggg caggaggaca cgggcagcct ggaggcaacc ctgaactacc tgctgaccaa     3060
```

```
ccggcggcag aagatcccct cgttgcacag tttaaacagc gaggaggagc gcatcttgcg    3120
ctatgtgcag cagagcgtga gccttaacct gatgcgcgac ggggtaacgc ccagcgtggc    3180
gctggacatg accgcgcgca acatggaacc gggcatgtat gcctcaaacc ggccgtttat    3240
caatcgccta atggactact tgcatcgcgc ggccgccgtg aaccccgagt atttcaccaa    3300
tgccatcttg aacccgcact ggctaccgcc ccctggtttc tacaccgggg gatttgaggt    3360
gcccgagggt aacgatggat tcctctggga cgacatagac gacagcgtgt tttcccgca    3420 accgcagacc ctgctagagt tgcaacagcg cgagcaggca gaggcggcgc tgcgaaagga    3480
aagcttccgc aggccaagca gcttgtccga tctaggcgct gcggcccgc ggtcagatgc    3540 gagtagccca tttccaagct tgatagggtc ttttaccagc actcgcacca cccgcccgcg    3600
cctgctgggc gaggaggagt acctaaacaa ctcgctgctg cagccgcagc gcgaaaagaa    3660
cctgcctccg gcatttccca acaacgggat agagagccta gtggacaaga tgagtagatg    3720
gaagacgtat gcgcaggagc acagggatgt gcccggcccg cgcccgccca ccgtcgtca    3780 aaggcacgac cgtcagcggg gtctggtgtg ggaggacgat gactcggcag acgacagcag    3840
cgtcctggat ttgggaggga gtggcaaccc gtttgcgcac cttcgcccca ggctggggag    3900
aatgttttaa aaaaaaaaaa aaaaagcatg atgcaaaata aaaaactcac caaggccatg    3960
gcaccgagcg ttggttttct tgtattcccc ttagtatgca gcgcgcggcg atgtatgagg    4020
aaggtcctcc tccctcctac gagagcgtgg tgagcgcggc gccagtggcg gcggcgctgg    4080
gttccccctt cgatgctccc ctggacccgc cgtttgtgcc tccgcggtac ctgcggccta    4140 ccgggggag aaacagcatc cgttactctg agttggcacc cctattcgac accaccgtg    4200 tgtaccttgt ggacaacaag tcaacggatg tggcatccct gaactaccag aacgaccaca    4260
gcaactttct aaccacggtc attcaaaaca atgactacag cccggggggag gcaagcacac    4320 agaccatcaa tcttgacgac cgttcgcact ggggcggcga cctgaaaacc atcctgcata    4380
ccaacatgcc aaatgtgaac gagttcatgt ttaccaataa gtttaaggcg cgggtgatgg    4440
tgtcgcgctc gcttactaag gacaaacagg tggagctgaa atatgagtgg gtggagttca    4500
cgctgcccga gggcaactac tccgagacca tgaccataga ccttatgaac aacgcgatcg    4560
tggagcacta cttgaaagtg ggcaggcaga acggggttct ggaaagcgac atcggggtaa    4620
agtttgacac ccgcaacttc agactggggt ttgacccagt cactggtctt gtcatgcctg    4680
gggtatatac aaacgaagcc ttccatccag acatcatttt gctgccagga tgcggggtgg    4740
acttcaccca cagccgcctg agcaacttgt tgggcatccg caagcggcaa cccttccagg    4800
agggctttag gatcacctac gatgacctgg agggtggtaa cattcccgca ctgttggatg    4860
tggacgccta ccaggcaagc ttaaaagatg acaccgaaca gggcgggat ggcgcaggcg    4920 gcggcaacaa cagtggcagc ggcgcggaag agaactccaa cgcggcagcc gcggcaatgc    4980
agccggtgga ggacatgaac gatcatgcca ttcgcggcga cacctttgcc acacgggcgg    5040
aggagaagcg cgctgaggcc gaggcagcgg cagaagctgc cgcccccgct gcgcaacccg    5100
aggtcgagaa gcctcagaag aaaccggtga tcaaacccct gacagaggac agcaagaaac    5160
gcagttacaa cctaataagc aatgacagca ccttcaccca gtaccgcagc tggtaccttg    5220
catacaacta cggcgaccct cagaccggga tccgctcatg accctccttt gcactcctg    5280 acgtaacctg cggctcggag caggtctact ggtcgttgcc agacatgatg caagaccccg    5340
tgaccttccg ctccacgagc cagatcagca actttccggt ggtgggcgcc gagctgttgc    5400
ccgtgcactc caagagcttc tacaacgacc aggccgtcta ctcccagctc atccgccagt    5460
```

```
ttacctctct gacccacgtg ttcaatcgct ttcccgagaa ccagattttg gcgcgcccgc    5520
cagcccccac catcaccacc gtcagtgaaa acgttcctgc tctcacagat cacgggacgc    5580
taccgctgcg caacagcatc ggaggagtcc agcgagtgac cattactgac gccagacgcc    5640
gcacctgccc ctacgtttac aaggccctgg gcatagtctc gccgcgcgtc ctatcgagcc    5700
gcactttttg agcaaacatg tccatcctta tatcgcccag caataacaca ggctggggcc    5760
tgcgcttccc aagcaagatg tttggcgggg caaagaagcg ctccgaccaa cacccagtgc    5820
gcgtgcgcgg gcactaccgc gcgccctggg gcgcgcacaa acgcggccgc actgggcgca    5880
ccaccgtcga tgacgccatt gacgcggtgg tggaggaggc gcgcaactac acgcccacgc    5940
cgccaccagt gtccacagtg gacgcggcca ttcagaccgt ggtgcgcgga gcccggcgtt    6000
atgctaaaat gaagagacgg cggaggcgcg tagcacgtcg ccaccgccgc cgacccggca    6060
ctgccgccca acgcgcggcg gcggccctgc ttaaccgcgc acgtcgcacc ggccgacggg    6120
cggccatgcg ggccgctcga aggctggccg cgggtattgt cactgtgccc cccaggtcca    6180
ggcgacgagc ggccgccgca gcagccgcgg ccattagtgc tatgactcag ggtcgcaggg    6240
gcaacgtgta ctgggtgcgc gactcggtta gcggcctgcg cgtgcccgtg cgcacccgcc    6300
ccccgcgcaa ctagattgca agaaaaaact acttagactc gtactgttgt atgtatccag    6360
cggcggcggc gcgcaacgaa gctatgtcca agcgcaaaat caaagaagag atgctccagg    6420
tcatcgcgcc ggagatctat ggccccccga agaaggaaga gcaggattac aagccccgaa    6480
agctaaagcg ggtcaaaaag aaaaagaaag atgatgatga tgatgaactt gacgacgagg    6540
tggaactgct gcacgcaacc gcgcccaggc ggcgggtaca gtggaaaggt cgacgcgtaa    6600
gacgtgtttt gcgaccccgg ccaccgctag tttttacgcc cggtgagcgc tccaccgca    6660
cctacaagcg cgtgtatgat gaggtgtacg gcgacgagga cctgcttgag caggccaacg    6720
agcgcctcgg ggagtttgcc tacggaaagc ggcataagga catgttggcg ttgccgctgg    6780
acgagggcaa cccaacacct agcctaaagc ccgtgacact gcagcaggtg ctgcccacgc    6840
ttgcaccgtc cgaagaaaag gcgcggccta a agcgcgagtc tggtgacttg gcacccaccg    6900
tgcagctgat ggtaccaag cgccagcgac tggaagatgt cttggaaaaa atgaccgtgg    6960
agcctgggct ggagcccgag gtccgcgtgc ggccaatcaa gcaggtggca ccgggactgg    7020
gcgtgcagac cgtggacgtt cagatacca ccaccagtag cactagtatt gccactgcca    7080
cagagggcat ggagacacaa acgtccccgg ttgcctcggc ggtggcagat gccgcggtgc    7140
aggcggccgc tgcggccgcg tccaaaacct ctacggaggt gcaaacggac ccgtggatgt    7200
ttcgcgtttc agcccccgg cgccgcgcc gttccaggaa gtacggcacc gccagcgcac    7260
tactgccga atatgcccta catccttcca tcgcgcctac ccccggctat cgtggctaca    7320
cctaccgccc cagaagacga gcgactaccc gacgccgaac caccactgga acccgccgcc    7380
gccgtcgccg tcgccagccc gtgctggccc cgatttccgt gcgcagggtg gctcgcgaag    7440
gaggcaggac cctggtgctg ccaacagcgc gctaccaccc cagcatcgtt taaaagccgg    7500
tctttgtggt tcttgcagat atggccctca cctgccgcct ccgtttccg gtgccgggat    7560
tccgaggaag aatgcaccgt aggaggggca tggccggcca cggcctgacg ggcggcatgc    7620
gtcgtgcgca ccaccggcgg cggcgcgcgt cgcaccgtcg catgcgcggc ggtatcctgc    7680
ccctccttat tccactgatc gccgcggcga ttggcgccgt gcccgaatt gcatccgtgg    7740
ccttgcaggc gcagagacac tgattaaaaa caagttgcat gtggaaaaat caaaataaaa    7800
```

-continued

```
agtctggagt ctcacgctcg cttggtcctg taactatttt gtagaatgga agacatcaac    7860
tttgcgtctc tggccccgcg acacggctcg cgcccgttca tgggaaactg gcaagatatc    7920
ggcaccagca atatgagcgg tggcgccttc agctggggct cgctgtggag cggcattaaa    7980
aatttcggtt ccaccattaa gaactatggc agcaaggcct ggaacagcag cacaggccag    8040
atgctgaggg acaagttgaa agagcaaaat ttccaacaaa aggtggtaga tggcctggcc    8100
tctggcatta gcggggtggt ggacctggcc aaccaggcag tgcaaaataa gattaacagt    8160
aagcttgatc cccgccctcc cgtagaggag cctccaccgg ccgtggagac agtgtctcca    8220
gaggggcgtg gcgaaaagcg tccgcggccc gacaggaag aaactctggt gacgcaaata     8280
gatgagcctc cctcgtacga ggaggcacta agcaaggcc tgcccaccac ccgtcccatc     8340
gcgcccatgg ctaccggagt gctgggccag cacacacctg taacgctgga cctgcctccc    8400
cccgctgaca cccagcagaa acctgtgctg ccagggccgt ccgccgttgt tgtaacccgc    8460
cctagccgcg cgtccctgcg ccgtgccgcc agcggtccgc gatcgatgcg gcccgtagcc    8520
agtggcaact ggcaaagcac actgaacagc atcgtgggtc tgggggtgca atccctgaag    8580
cgccgacgat gcttctaaat agctaacgtg tcgtatgtgt catgtatgcg tccatgtcgc    8640
cgccagagga gctgctgagc cgccgtgcgc ccgctttcca agatggctac ccttcgatg     8700
atgccgcagt ggtcttacat gcacatctcg ggccaggacg cctcggagta cctgagcccc    8760
gggctggtgc agtttgcccg cgccaccgag acgtacttca gcctgaataa caagtttaga    8820
aaccccacgg tggcacctac gcacgacgta accacagacc ggtcccagcg tttgacgctg    8880
cggttcatcc ctgtggaccg cgaggatacc gcgtactcgt acaaagcgcg gttcaccctg    8940
gctgtgggtg acaaccgtgt gcttgatatg gcttccacgt actttgacat ccgcggcgtg    9000
ctggacaggg ggcctacttt taagcccctac tccggcactg cctacaacgc tctagctccc    9060
aagggcgctc ctaactcctg tgagtgggaa caaaccgaag atagcggccg ggcagttgcc    9120
gaggatgaag aagaggaaga tgaagatgaa gaagaggaag aagaagagca aaacgctcga    9180
gatcaggcta ctaagaaaac acatgtctat gcccaggctc ctttgtctgg agaaacaatt    9240
acaaaaagcg ggctacaaat aggatcagac aatgcagaaa cacaagctaa acctgtatac    9300
gcagatcctt cctatcaacc agaacctcaa attggcgaat ctcagtggaa cgaagctgat    9360
gctaatgcgg caggagggag agtgcttaaa aaaacaactc ccatgaaacc atgctatgga    9420
tcttatgcca ggcctacaaa tccttttggt ggtcaatccg ttctggttcc ggatgaaaaa    9480
ggggtgcctc ttccaaaggt tgacttgcaa ttcttctcaa atactacctc tttgaacgac    9540
cggcaaggca atgctactaa accaaaagtg gttttgtaca gtgaagatgt aaatatggaa    9600
accccagaca cacatctgtc ttacaaacct ggaaaaggtg atgaaaattc taaagctatg    9660
ttgggtcaac aatctatgcc aaacagaccc aattacattg ctttcaggga caattttatt    9720
ggcctaatgt attataacag cactggcaac atgggtgttc ttgctggtca ggcatcgcag    9780
ctaaatgccg tggtagattt gcaagacaga aacacagagc tgtcctatca actcttgctt    9840
gattccatag gtgatagaac cagatatttt tctatgtgga atcaggctgt agacagctat    9900
gatccagatg ttagaatcat tgaaaaccat ggaactgagg atgaattgcc aaattattgt    9960
tttcctcttg ggggtattgg ggtaactgac acctatcaag ctattaaggc taatggcaat    10020
ggctcaggcg ataatggaga tactacatgg acaaaagatg aaacttttgc aacacgtaat    10080
gaaataggag tgggtaacaa ctttgccatg gaaattaacc taaatgccaa cctatgggag    10140
aatttccttt actccaatat tgcgctgtac ctgccagaca agctaaaata caacccccacc    10200
```

```
aatgtggaaa tatctgacaa ccccaacacc tacgactaca tgaacaagcg agtggtggct   10260
cccgggcttg tagactgcta cattaacctt ggggcgcgct ggtctctgga ctacatggac   10320
aacgttaatc cctttaacca ccaccgcaat gcgggcctcc gttatcgctc catgttgttg   10380
ggaaacggcc gctacgtgcc ctttcacatt caggtgcccc aaaagttttt tgccattaaa   10440
aacctcctcc tcctgccagg ctcatataca tatgaatgga acttcaggaa ggatgttaac   10500
atggttctgc agagctctct gggaaacgat cttagagttg acggggctag cattaagttt   10560
gacagcattt gtctttacgc caccttcttc cccatggccc acaacacggc tccacgctg    10620 gaagccatgc tcagaaatga caccaacgac cagtccttta atgactacct ttccgccgcc   10680
aacatgctat accccatacc cgccaacgcc accaacgtgc ccatctccat cccatcgcgc   10740
aactgggcag catttcgcgg ttgggccttc acacgcttga agacaaagga aacccttcc    10800 ctgggatcag gctacgaccc ttactacacc tactctggct ccataccata ccttgacgga   10860
accttctatc ttaatcacac ctttaagaag gtggccatta cctttgactc ttctgttagc   10920
tggccgggca acgaccgcct gcttactccc aatgagtttg agattaaacg ctcagttgac   10980
ggggagggct acaacgtagc tcagtgcaac atgaccaagg actggttcct ggtgcagatg   11040
ttggccaact acaatattgg ctaccagggc ttctacattc agaaagcta caaggaccgc    11100 atgtactcgt tcttcagaaa cttccagccc atgagccggc aagtggttga cgatactaaa   11160
tacaaggagt atcagcaggt tggaattctt caccagcata caactcagg attcgtaggc    11220 tacctcgctc ccaccatgcg cgagggacag gcttaccccg ccaacgtgcc ctacccacta   11280
ataggcaaaa ccgcggttga cagtattacc cagaaaaagt ttctttgcga tcgcacccttt  11340 tggcgcatcc cattctccag taactttatg tccatgggcg cactcacaga cctgggccaa   11400
aaccttctct acgccaactc cgcccacgcg ctagacatga cttttgaggt ggatcccatg   11460
gacgagccca cccttcttta tgttttgttt gaagtctttg acgtggtccg tgtgcaccag   11520
ccgcaccgcg gcgtcatcga daccgtgtac ctgcgcacgc ccttctcggc cggcaacgcc   11580
acaacataaa agaagcaagc aacatcaaca acagctgccg ccatgggctc cagtgagcag   11640
gaactgaaag ccattgtcaa agatcttggt tgtgggccat attttttggg cacctatgac   11700
aagcgctttc caggctttgt ttctccacac aagctcgcct gcgccatagt caatacggcc   11760
ggtcgcgaga ctgggggcgt acactggatg gcctttgcct ggaacccgcg ctcaaaaaca   11820
tgctacctct ttgagccctt tggcttttct gaccaacgac tcaagcaggt ttaccagttt   11880
gagtacgagt cactcctgcg ccgtagcgcc attgcttctt ccccccgaccg ctgtataacg   11940 ctggaaaagt ccacccaaag cgtgcagggg cccaactcgg ccgcctgtgg actattctgc   12000
tgcatgtttc tccacgcctt tgccaactgg ccccaaactc ccatggatca accccacc    12060 atgaacctta ttaccggggt acccaactcc atgcttaaca gtccccaggt acagcccacc   12120
ctgcgtcgca accaggaaca gctctacagc ttcctggagc gccactcgcc ctacttccgc   12180
agccacagtg cgcagattag gagcgccact tcttttttgtc acttgaaaaa catgtaaaaa   12240
taatgtacta ggagacactt tcaataaagg caaatgtttt tatttgtaca ctctcgggtg   12300
attatttacc ccccacccctt gccgtctgcg ccgtttaaaa atcaagggg ttctgccgcg    12360 catcgctatg cgccactggc agggacacgt tgcgatactg gtgtttagtg ctccacttaa   12420
actcaggcac aaccatccgc ggcagctcgg tgaagttttc actccacagg ctgcgcacca   12480
tcaccaacgc gtttagcagg tcgggcgccg atatcttgaa gtcgcagttg gggcctccgc   12540
```

```
cctgcgcgcg cgagttgcga tacacagggt tgcagcactg gaacactatc agcgccgggt    12600
ggtgcacgct ggccagcacg ctcttgtcgg agatcagatc cgcgtccagg tcctccgcgt    12660
tgctcagggc gaacggagtc aactttggta gctgccttcc caaaaagggt gcatgcccag    12720
gctttgagtt gcactcgcac cgtagtggca tcagaaggtg accgtgcccg gtctgggcgt    12780
taggatacag cgcctgcatg aaagccttga tctgcttaaa agccacctga gcctttgcgc    12840
cttcagagaa gaacatgccg caagacttgc cggaaaactg attggccgga caggccgcgt    12900
catgcacgca gcaccttgcg tcggtgttgg agatctgcac cacatttcgg ccccaccggt    12960
tcttcacgat cttggccttg ctagactgct ccttcagcgc gcgctgcccg ttttcgctcg    13020
tcacatccat ttcaatcacg tgctccttat ttatcataat gctcccgtgt agacacttaa    13080
gctcgccttc gatctcagcg cagcggtgca gccacaacgc gcagcccgtg ggctcgtggt    13140
gcttgtaggt tacctctgca aacgactgca ggtacgcctg caggaatcgc cccatcatcg    13200
tcacaaaggt cttgttgctg gtgaaggtca gctgcaaccc gcggtgctcc tcgtttagcc    13260
aggtcttgca tacggccgcc agagcttcca cttggtcagg cagtagcttg aagtttgcct    13320
ttagatcgtt atccacgtgg tacttgtcca tcaacgcgcg cgcagcctcc atgcccttct    13380
cccacgcaga cacgatcggc aggctcagcg ggtttatcac cgtgctttca ctttccgctt    13440
cactggactc ttccttttcc tcttgcgtcc gcatacccg cgccactggg tcgtcttcat    13500
tcagccgccg caccgtgcgc ttacctccct tgccgtgctt gattagcacc ggtgggttgc    13560
tgaaacccac catttgtagc gccacatctt ctctttcttc ctcgctgtcc acgatcacct    13620
ctggggatgg cgggcgctcg ggcttgggag aggggcgctt cttttctttt ttggacgcaa    13680
tggccaaatc cgccgtcgag gtcgatggcc gcgggctggg tgtgcgcggc accagcgcat    13740
cttgtgacga gtcttcttcg tcctcggact cgagacgccg cctcagccgc tttttggg    13800 gcgcgcgggg aggcggcggc gacggcgacg gggacgacac gtcctccatg gttggtggac    13860
gtcgcgccgc accgcgtccg cgctcggggg tggtttcgcg ctgctcctct tcccgactgg    13920
ccatttcctt ctcctatagg cagaaaaaga tcatggagtc agtcgagaag gaggacagcc    13980
taaccgcccc ctttgagttc gccaccaccg cctccaccga tgccgccaac gcgcctacca    14040 ccttcccgt cgaggcaccc ccgcttgagg aggaggaagt gattatcgag caggacccag    14100
gttttgtaag cgaagacgac gaggatcgct cagtaccaac agaggataaa aagcaagacc    14160
aggacgacgc agaggcaaac gaggaacaag tcgggcgggg ggaccaaagg catggcgact    14220
acctagatgt gggagacgac gtgctgttga agcatctgca gcgccagtgc gccattatct    14280
gcgacgcgtt gcaagagcgc agcgatgtgc ccctcgccat agcggatgtc agccttgcct    14340
acgaacgcca cctgttctca ccgcgcgtac ccccaaacg ccaagaaaac ggcacatgcg    14400
agcccaaccc gcgcctcaac ttctacccg tatttgccgt gccagaggtg cttgccacct    14460
atcacatctt tttccaaaac tgcaagatac ccctatcctg ccgtgccaac cgcagccgag    14520
cggacaagca gctggccttg cggcagggcg ctgtcatacc tgatatcgcc tcgctcgacg    14580
aagtgccaaa aatctttgag ggtcttggac gcgacgagaa acgcgcggca aacgctctgc    14640
aacaagaaaa cagcgaaaat gaaagtcact gtggagtgct ggtggaactt gagggtgaca    14700
acgcgcgcct agccgtgctg aaacgcagca tcgaggtcac ccactttgcc tacccggcac    14760
ttaacctacc ccccaaggtt atgagcacag tcatgagcga gctgatcgtg cgccgtgcac    14820
gacccctgga gagggatgca aacttgcaag aacaaaccga ggagggccta cccgcagttg    14880
gcgatgagca gctggcgcgc tggcttgaga cgcgcgagcc tgccgacttg gaggagcgac    14940
```

```
gcaagctaat gatggccgca gtgcttgtta ccgtggagct tgagtgcatg cagcggttct   15000
ttgctgaccc ggagatgcag cgcaagctag aggaaacgtt gcactacacc tttcgccagg   15060
gctacgtgcg ccaggcctgc aaaatttcca acgtggagct ctgcaacctg gtctcctacc   15120
ttggaatttt gcacgaaaac cgcctcgggc aaaacgtgct tcattccacg ctcaagggcg   15180
aggcgcgccg cgactacgtc cgcgactgcg tttacttatt tctgtgctac acctggcaaa   15240
cggccatggg cgtgtggcag caatgcctgg aggagcgcaa cctaaaggag ctgcagaagc   15300
tgctaaagca aaacttgaag gacctatgga cggccttcaa cgagcgctcc gtggccgcgc   15360
acctggcgga cattatcttc cccgaacgcc tgcttaaaac cctgcaacag ggtctgccag   15420
acttcaccag tcaaagcatg ttgcaaaact ttaggaactt tatcctagag cgttcaggaa   15480
ttctgcccgc cacctgctgt gcgcttccta gcgactttgt gcccattaag taccgtgaat   15540
gccctccgcc gctttggggt cactgctacc ttctgcagct agccaactac cttgcctacc   15600
actccgacat catggaagac gtgagcggtg acggcctact ggagtgtcac tgtcgctgca   15660
acctatgcac cccgcaccgc tccctggtct gcaattcgca actgcttagc gaaagtcaaa   15720
ttatcggtac ctttgagctg cagggtccct cgcctgacga aaagtccgcg gctccggggt   15780
tgaaactcac tccggggctg tggacgtcgg cttaccttcg caaatttgta cctgaggact   15840
accacgccca cgagattagg ttctacgaag accaatcccg cccgccaaat gcggagctta   15900
ccgcctgcgt cattacccag ggccacatcc ttggccaatt gcaagccatc aacaaagccc   15960
gccaagagtt tctgctacga aagggacggg gggtttacct ggaccccag tccggcgagg   16020 agctcaaccc aatcccccg ccgccgcagc cctatcagca gccgcgggcc cttgcttccc   16080
aggatggcac ccaaaaagaa gctgcagctg ccgccgccgc cacccacgga cgaggaggaa   16140
tactgggaca gtcaggcaga ggaggttttg gacgaggagg aggagatgat ggaagactgg   16200
gacagcctag acgaagcttc cgaggccgaa gaggtgtcag acgaaacacc gtcaccctcg   16260
gtcgcattcc cctcgccggc gccccagaaa ttggcaaccg ttcccagcat cgctacaacc   16320
tccgctcctc aggcgccgcc ggcactgcct gttcgccgac ccaaccgtag atgggacacc   16380
actggaacca gggccggtaa gtctaagcag ccgccgccgt tagcccaaga gcaacaacag   16440
cgccaaggct accgctcgtg gcgcgggcac aagaacgcca tagttgcttg cttgcaagac   16500
tgtgggggca acatctcctt cgcccgccgc tttcttctct accatcacgg cgtggccttc   16560
ccccgtaaca tcctgcatta ctaccgtcat ctctacagcc cctactgcac cggcggcagc   16620
ggcagcggca gcaacagcag cggtcacaca gaagcaaagg cgaccggata gcaagactct   16680
gacaaagccc aagaaatcca cagcggcggc agcagcagga ggaggagcgc tgcgtctggc   16740
gcccaacgaa cccgtatcga cccgcgagct tagaaatagg attttcca ctctgtatgc   16800 tatatttcaa caaagcaggg gccaagaaca agagctgaaa ataaaaaaca ggtctctgcg   16860
ctccctcacc cgcagctgcc tgtatcacaa aagcgaagat cagcttcggc gcacgctgga   16920
agacgcggag gctctcttca gcaaatactg cgcgctgact cttaaggact agtttcgcgc   16980
cctttctcaa atttaagcgc gaaaactacg tcatctccag cggccacacc cggcgccagc   17040
acctgtcgtc agcgccatta tgagcaagga aattcccacg ccctacatgt ggagttacca   17100
gccacaaatg ggacttgcgg ctggagctgc ccaagactac tcaacccgaa taaactacat   17160
gagcgcggga cccacatga tatcccgggt caacggaatc cgcgcccacc gaaaccgaat   17220
tctcctcgaa caggcggcta ttaccaccac acctcgtaat aaccttaatc cccgtagttg   17280
```

```
gcccgctgcc ctggtgtacc aggaaagtcc cgctcccacc actgtggtac ttcccagaga   17340
cgcccaggcc gaagttcaga tgactaactc aggggcgcag cttgcgggcg gctttcgtca   17400
cagggtgcgg tcgcccgggc agggtataac tcacctgaaa atcagagggc gaggtattca   17460
gctcaacgac gagtcggtga gctcctctct tggtctccgt ccggacggga catttcagat   17520
cggcggcgct ggccgctctt catttacgcc ccgtcaggcg atcctaactc tgcagacctc   17580
gtcctcggag ccgcgctccg gaggcattgg aactctacaa tttattgagg agttcgtgcc   17640
ttcggtttac ttcaacccct tttctggacc tcccggccac tacccggacc agtttattcc   17700
caactttgac gcggtgaaag actcggcgga cggctacgac tgaatgacca gtggagaggc   17760
agagcgactg cgcctgacac acctcgacca ctgccgccgc cacaagtgct ttgcccgcgg   17820
ctccggtgag ttttgttact ttgaattgcc cgaagagcat atcgagggcc cggcgcacgg   17880
cgtccggctc accacccagg tagagcttac acgtagcctg attcgggagt ttaccaagcg   17940 cccccctgcta gtggagcggg agcggggtcc ctgtgttctg accgtggttt gcaactgtcc   18000
taaccctgga ttacatcaag atctttgttg tcatctctgt gctgagtata ataaatacag   18060
aaattagaat ctactggggc tcctgtcgcc atcctgtgaa cgccaccgtt tttacccacc   18120
caaagcagac caaagcaaac ctcacctccg gtttgcacaa gcgggccaat aagtaccttca  18180 cctggtactt taacggctct tcatttgtaa tttacaacag tttccagcga gacgaagtaa   18240
gtttgccaca caaccttctc ggcttcaact acaccgtcaa gaaaaacacc accaccacca   18300
ccctcctcac ctgccgggaa cgtacgagtg cgtcaccggt tgctgcgccc acacctacag   18360
cctgagcgta accagacatt actcccattt ttccaaaaca ggaggtgagc tcaactcccg   18420
gaactcaggt caaaaaagca ttttgcgggg tgctgggatt ttttaattaa gtatatgagc   18480
aattcaagta actctacaag cttgtctaat ttttctggaa ttggggtcgg ggttatcctt   18540
actcttgtaa ttctgtttat tcttatacta gcacttctgt gccttagggt tgccgcctgc   18600
tgcacgcacg tttgtaccta ttgtcagctt tttaaacgct gggggcaaca tccaagatga   18660
ggtacatgat tttaggcttg ctcgcccttg cggcagtctg cagcgctgcc aaaaaggttg   18720
agtttaagga accagcttgc aatgttacat ttaaatcaga agctaatgaa tgcactactc   18780
ttataaaatg caccacagaa catgaaaagc ttattattcg ccacaaagac aaaattggca   18840
agtatgctgt atatgctatt tggcagccag gtgacactaa cgactataat gtcacagtct   18900
tccaaggtga aaatcgtaaa acttttatgt ataaatttcc attttatgaa atgtgcgata   18960
ttaccatgta catgagcaaa cagtacaagt tgtggccccc acaaaagtgt ttagagaaca   19020
ctggcacctt ttgttccacc gctctgctta ttacagcgct tgctttggta tgtaccttac   19080
tttatctcaa atacaaaagc agacgcagtt ttattgatga aaagaaaatg ccttgatttt   19140
ccgcttgctt gtattcccct ggacaattta ctctatgtgg gatatgctcc aggcgggcaa   19200
gattataccc acaaccttca aatcaaactt tcctggacgt tagcgcctga tttctgccag   19260
cgcctgcact gcaaatttga tcaaacccag cttcagcttg cctgctccag agatgaccgg   19320
ctcaaccatc gcgcccacaa cggactatcg caacaccact gctaccggac taacatctgc   19380
cctaaattta ccccaagttc atgcctttgt caatgactgg gcgagcttgg acatgtggtg   19440
gttttccata gcgcttatgt ttgtttgcct tattattatg tggcttattt gttgcctaaa   19500
gcgcagacgc gccagacccc ccatctatag gcctatcatt gtgctcaacc cacacaatga   19560
aaaaattcat agattggacg gtctgaaacc atgttctctt cttttacagt atgattaaat   19620
gagacatgat tcctcgagtt cttatattat tgacccttgt tgcgcttttc tgtgcgtgct   19680
```

```
ctacattggc cgcggtcgct cacatcgaag tagattgcat cccacctttc acagtttacc   19740
tgctttacgg atttgtcacc cttatcctca tctgcagcct cgtcactgta gtcatcgcct   19800
tcattcagtt cattgactgg gtttgtgtgc gcattgcgta cctcaggcac catccgcaat   19860
acagagacag gactatagct gatcttctca gaattcttta attatgaaac ggagtgtcat   19920
ttttgttttg ctgattttt gcgccctacc tgtgctttgc tcccaaacct cagcgcctcc   19980
caaaagacat atttcctgca gattcactca aatatggaac attcccagct gctacaacaa   20040
acagagcgat ttgtcagaag cctggttata cgccatcatc tctgtcatgg ttttttgcag   20100
taccattttt gccctagcca tatatccata ccttgacatt ggctggaatg ccatagatgc   20160
catgaaccac cctactttcc cagtgcccgc tgtcatacca ctgcaacagg ttattgcccc   20220
aatcaatcag cctcgccccc cttctcccac ccccactgag attagctact ttaatttgac   20280
aggtggagat gactgaatct ctagagtcga cctgcaggca tgcaagcttg gcgtaatcat   20340
ggtcatagct gtttcctgtg tgaaattgtt atccgctcac aattccacac aacatacgag   20400
ccggaagcat aaagtgtaaa gcctggggtg cctaatgagt gagctaactc acattaattg   20460
cgttgcgctc actgcccgct ttccagtcgg gaaacctgtc gtgccagctg cattaatgaa   20520
tcggccaacg cgcggggaga gcggtttgc gtattgggcg ctcttccgct tcctcgctca   20580
ctgactcgct gcgctcggtc gttcggctgc ggcgagcggt atcagctcac tcaaaggcgg   20640
taatacggtt atccacagaa tcaggggata acgcaggaaa gaacatgtga gcaaaaggcc   20700
agcaaaaggc caggaaccgt aaaaaggccg cgttgctggc gttttccat aggctccgcc   20760 cccctgacga gcatcacaaa aatcgacgct caagtcagag gtggcgaaac ccgacaggac   20820
tataaagata ccaggcgttt ccccctggaa gctccctcgt gcgctctcct gttccgaccc   20880
tgccgcttac cggatacctg tccgcctttc tcccttcggg aagcgtggcg ctttctcaat   20940
gctcacgctg taggtatctc agttcggtgt aggtcgttcg ctccaagctg ggctgtgtgc   21000
acgaaccccc cgttcagccc gaccgctgcg ccttatccgg taactatcgt cttgagtcca   21060
acccggtaag acacgactta tcgccactgg cagcagccac tggtaacagg attagcagag   21120
cgaggtatgt aggcggtgct acagagttct tgaagtggtg gcctaactac ggctacacta   21180
gaaggacagt atttggtatc tgcgctctgc tgaagccagt taccttcgga aaaagagttg   21240
gtagctcttg atccggcaaa caaaccaccg ctggtagcgg tggtttttt gtttgcaagc   21300 agcagattac gcgcagaaaa aaaggatctc aagaagatcc tttgatcttt tctacggggt   21360
ctgacgctca gtggaacgaa aactcacgtt aagggatttt ggtcatgaga ttatcaaaaa   21420
ggatcttcac ctagatcctt ttaaattaaa aatgaagttt taaatcaatc taaagtatat   21480
atgagtaaac ttggtctgac agttaccaat gcttaatcag tgaggcacct atctcagcga   21540
tctgtctatt tcgttcatcc atagttgcct gactccccgt cgtgtagata actacgatac   21600
gggagggctt accatctggc cccagtgctg caatgatacc gcgagaccca cgctcaccgg   21660
ctccagattt atcagcaata aaccagccag ccggaagggc cgagcgcaga agtggtcctg   21720
caactttatc cgcctccatc cagtctatta attgttgccg ggaagctaga gtaagtagtt   21780
cgccagttaa tagtttgcgc aacgttgttg ccattgctac aggcatcgtg gtgtcacgct   21840
cgtcgtttgg tatggcttca ttcagctccg gttcccaacg atcaaggcga gttacatgat   21900
cccccatgtt gtgcaaaaaa gcggttagct ccttcggtcc tccgatcgtt gtcagaagta   21960
agttggccgc agtgttatca ctcatggtta tggcagcact gcataattct cttactgtca   22020
```

```
tgccatccgt aagatgcttt tctgtgactg gtgagtactc aaccaagtca ttctgagaat    22080
agtgtatgcg gcgaccgagt tgctcttgcc cggcgtcaat acgggataat accgcgccac    22140
atagcagaac tttaaaagtg ctcatcattg gaaaacgttc ttcggggcga aaactctcaa    22200
ggatcttacc gctgttgaga tccagttcga tgtaacccac tcgtgcaccc aactgatctt    22260
cagcatcttt tactttcacc agcgtttctg ggtgagcaaa aacaggaagg caaaatgccg    22320
caaaaaaggg aataagggcg acacggaaat gttgaatact catactcttc ctttttcaat    22380
attattgaag catttatcag ggttattgtc tcatgagcgg atacatattt gaatgtattt    22440
agaaaaataa acaaataggg gttccgcgca catttccccg aaaagtgcca cctgacgtct    22500
aagaaaccat tattatcatg acattaacct ataaaaatag gcgtatcacg aggccctttc    22560
gtc                                                                  22563

<210> SEQ ID NO 105
<211> LENGTH: 8350
<212> TYPE: DNA
<213> ORGANISM: artificial
<220> FEATURE:
<223> OTHER INFORMATION: plasmid psyx20-lacIq

<400> SEQUENCE: 105
cagctggcgt aatagcgaag aggcccgcac cgatcgccct tcccaacagt tgcgcagcct      60
gaatggcgaa tgggacgcgc cctgtagcgg cgcattaagc gcggcgggtg tggtggttac     120
gcgcagcgtg accgctacac ttgccagcgc cctagcgccc gctcctttcg ctttcttccc     180
ttcctttctc gccacgttcg ccggctttcc ccgtcaagct ctaaatcggg gctcccttt      240 agggttccga tttagtgctt tacggcacct cgaccccaaa aaacttgatt agggtgatgg     300
ttcacgtagt gggccatcgc cctgatagac ggtttttcgc cctttgacgt tggagtccac     360
gttctttaat agtggactct tgttccaaac tggaacaaca ctcaacccta tctcggtcta     420
ttcttttgat ttataaggga ttttgccgat ttcggcctat tggttaaaaa atgagctgat     480
ttaacaaaaa tttaacgcga attttaacaa aattcgaccg atgcccttga gagccttcaa     540
cccagtcagc tccttccggt gggcgcgggg catgactatc gtcgccgcac ttatgactgt     600
cttctttatc atgcaactcg taggacaggt gccggcagcg ctctgggtca ttttcggcga     660
ggaccgcttt cgctggagcg cgacgatgat cggcctgtcg cttgcggtat tcggaatctt     720
gcacgccctc gctcaagcct tcgtcactgg tcccgccacc aaacgtttcg gcgagaagca     780
ggccattatc gccggcatgg cggccgacgc gctgggctac gtcttgctgg cgttcgcgac     840
gcgaggctgg atggccttcc ccattatgat tcttctcgct tccggcggca tcgggatgcc     900
cgcgttgcag gccatgctgt ccaggcaggt agatgacgac catcagggac agcttcaagg     960
atcgctcgcg gctcttacca gcctaacttc gatcattgga ccgctgatcg tcacggcgat    1020
ttatgccgcc tcggcgagca catggaacgg gttggcatgg attgtaggcg ccgccctata    1080
ccttgtctgc ctccccgcgt tgcgtcgcgg tgcatggagc cgggccacct cgacctgaat    1140
ggaagccggc ggcacctcgc taacggattc accactccgc agaccgcca taaaacgccc    1200 tgagaagccc gtgacgggct tttcttgtat tatgggtagt ttccttgcat gaatccataa    1260
aaggcgcctg tagtgccatt taccccatt cactgccaga gccgtgagcg cagcgaactg    1320
aatgtcacga aaaagacagc gactcaggtg cctgatggtc ggagacaaaa ggaatattca    1380
gcgatttgcc cgagcttgcg agggtgctac ttaagccttt aggatttttaa ggtctgtttt    1440 gtagaggagc aaacagcgtt tgcgacatcc ttttgtaata ctgcggaact gactaaagta    1500
```

```
gtgagttata cacagggctg ggatctattc tttttatctt tttttattct ttctttattc   1560
tataaattat aaccacttga atataaacaa aaaaaacaca caaaggtcta gcggaattta   1620
cagagggtct agcagaattt acaagttttc cagcaaaggt ctagcagaat ttacagatac   1680
ccacaactca aaggaaaagg actagtaatt atcattgact agcccatctc aattggtata   1740
gtgattaaaa tcacctagac caattgagat gtatgtctga attagttgtt ttcaaagcaa   1800
atgaactagc gattagtcgc tatgacttaa cggagcatga aaccaagcta attttatgct   1860
gtgtggcact actcaacccc acgattgaaa accctacaag gaaagaacgg acggtatcgt   1920
tcacttataa ccaatacgct cagatgatga acatcagtag ggaaaatgct tatggtgtat   1980
tagctaaagc aaccagagag ctgatgacga gaactgtgga aatcaggaat cctttggtta   2040
aaggctttga gattttccag tggacaaact atgccaagtt ctcaagcgaa aaattagaat   2100
tagtttttag tgaagagata ttgccttatc ttttccagtt aaaaaaattc ataaaatata   2160
atctggaaca tgttaagtct tttgaaaaca aatactctat gaggatttat gagtggttat   2220
taaaagaact aacacaaaag aaaactcaca aggcaaatat agagattagc cttgatgaat   2280
ttaagttcat gttaatgctt gaaaataact accatgagtt taaaaggctt aaccaatggg   2340
ttttgaaacc aataagtaaa gatttaaaca cttacagcaa tatgaaattg gtggttgata   2400
agcgaggccg cccgactgat acgttgattt tccaagttga actagataga caaatggatc   2460
tcgtaaccga acttgagaac aaccagataa aaatgaatgg tgacaaaata ccaacaacca   2520
ttacatcaga ttcctaccta cataacggac taagaaaaac actacacgat gctttaactg   2580
caaaaattca gctcaccagt tttgaggcaa aattttgag tgacatgcaa agtaagtatg   2640
atctcaatgg ttcgttctca tggctcacgc aaaaacaacg aaccacacta gagaacatac   2700
tggctaaata cggaaggatc tgaggttctt atggctcttg tatctatcag tgaagcatca   2760
agactaacaa acaaaagtag aacaactgtt caccgttaca tatcaagggg aaaactgtcc   2820
atatgcacag atgaaaacgg tgtaaaaaag atagatacat cagagctttt acgagttttt   2880
ggtgcattca agctgttca ccatgaacag atcgacaatg taacagatga acagcatgta   2940
acacctaata gaacaggtga aaccagtaaa acaaagcaac tagaacatga aattgaacac   3000
ctgagacaac ttgttacagc tcaacagtca cacatagaca gcctgaaaca ggcgatgctg   3060
cttatcgaat caaagctgcc gacaaacacgg gagccagtga cgcctcccgt ggggaaaaaa   3120
tcatggcaat tctggaagaa atagcgcttt cagccggcaa accggctgaa gccggatctg   3180
cgattctgat aacaaactag caacaccaga acagcccgtt tgcgggcagc aaaacccgta   3240
cttttggacg ttccggcggt tttttgtggc gagtggtgtt cggcggtgc gcgattattg   3300 aagcatttat cagggttatt gtctcatgag cggatacata tttgaatgta tttagaaaaa   3360
taaacaaata ggggttccgc gcacatttcc ccgaaaagtg ccacctgacg tctaagaaac   3420
cattattatc atgacattaa cctataaaaa taggcgtatc acgaggccct ttcgtcttca   3480
agaattcgcg cgcgaaggcc aagcggcatg catttacgtt gacaccatcg aatggcgcaa   3540
aacctttcgc ggtatggcat gatagcgccc ggaagagagt caattcaggg tggtgaatgt   3600
gaaaccagta acgttatacg atgtcgcaga gtatgccggt gtctcttatc agaccgtttc   3660
ccgcgtggtg aaccaggcca gccacgtttc tgcgaaaacg cgggaaaaag tggaagcggc   3720
gatggcggag ctgaattaca ttcccaaccg cgtggcacaa caactggcgg caaacagtc   3780 gttgctgatt ggcgttgcca cctccagtct ggccctgcac gcgccgtcgc aaattgtcgc   3840
```

```
ggcgattaaa tctcgcgccg atcaactggg tgccagcgtg gtggtgtcga tggtagaacg    3900
aagcggcgtc gaagcctgta aagcggcggt gcacaatctt ctcgcgcaac gcgtcagtgg    3960
gctgatcatt aactatccgc tggatgacca ggatgccatt gctgtggaag ctgcctgcac    4020
taatgttccg gcgttatttc ttgatgtctc tgaccagaca cccatcaaca gtattatttt    4080
ctcccatgaa gacggtacgc gactgggcgt ggagcatctg gtcgcattgg gtcaccagca    4140
aatcgcgctg ttagcgggcc cattaagttc tgtctcggcg cgtctgcgtc tggctggctg    4200
gcataaatat ctcactcgca atcaaattca gccgatagcg gaacgggaag gcgactggag    4260
tgccatgtcc ggttttcaac aaaccatgca aatgctgaat gagggcatcg ttcccactgc    4320
gatgctggtt gccaacgatc agatggcgct gggcgcaatg cgcgccatta ccgagtccgg    4380
gctgcgcgtt ggtgcggata tctcggtagt gggatacgac gataccgaag acagctcatg    4440
ttatatcccg ccgtcaacca ccatcaaaca ggattttcgc ctgctggggc aaaccagcgt    4500
ggaccgcttg ctgcaactct ctcagggcca ggcggtgaag gcaatcagc tgttgcccgt     4560
ctcactggtg aaaagaaaaa ccaccctggc gcccaatacg caaaccgcct ctccccgcgc    4620
gttggccgat tcattaatgc agctggcacg acaggtttcc cgactggaaa gcggcagtg    4680
agcgcaacgc aattaatgtg agttagctca ctcattaggc gaattctcat gtttgacagc    4740
ttatcatcga taagctttaa tgcggtagtt tatcacagtt aaattgctaa cgcagtcagg    4800
caccgtgtat gaaatctaac aatgcgctca tcgtcatcct cggcaccgtc acctggatg     4860
ctgtaggcat aggcttggtt atgccggtac tgccgggcct cttgcgggat atcgtccatt    4920
ccgacagcat cgccagtcac tatggcgtgc tgctagcgct atatgcgttg atgcaatttc    4980
tatgcgcacc cgttctcgga gcactgtccg accgctttgg ccgccgccca gtcctgctcg    5040
cttcgctact tggagccact atcgactacg cgatcatggc gaccacaccc gtcctgtgga    5100
tcctctacgc cggacgcatc gtggccggca tcaccggcgc cacaggtgcg gttgctggcg    5160
cctatatcgc cgacatcacc gatggggaag atcgggctcg ccacttcggg ctcatgagcg    5220
cttgtttcgg cgtgggtatg gtggcaggcc ccgtggccgg gggactgttg gcgccatct    5280
ccttgcatgc accattcctt gcggcggcgg tgctcaacgg cctcaaccta ctactgggct    5340
gcttcctaat gcaggaatcg cataagggag agcgtcgacc gatgcccttg agagccttca    5400
acccagtcag ctccttccgg tgggcgcggg gcatgactat cgtcgccgca cttatgactg    5460
tcttctttat catgcaactc gtaggacagg tgccggcagc gctctgggtc attttcggcg    5520
aggaccgctt tcgctggagc gcgacgatga tcggcctgtc gcttgcggta ttcggaatct    5580
tgcacgccct cgctcaagcc ttcgtcactg gtcccgccac caaacgtttc ggcgagaagc    5640
aggccattat cgccggcatg gcggccgacg cgctgggcta cgtcttgctg gcgttcgcga    5700
cgcgaggctg gatggccttc cccattatga ttcttctcgc ttccggcggc atcgggatgc    5760
ccgcgttgca ggccatgctg tccaggcagg tagatgacga ccatcaggga cagcttcaag    5820
gatcgctcgc ggctcttacc agcctaactt cgatcattgg accgctgatc gtcacggcga    5880
tttatgccgc ctcggcgagc acatggaacg ggttggcatg gattgtaggc gccgccctat    5940
accttgtctg cctccccgcg ttgcgtcgcg gtgcatggag ccgggccacc tcgacctgaa    6000
tggaagccgg cggcacctcg ctaacggatt caccactcca agaattggag ccaatcaatt    6060
cttgcggaga actgtgaatg cgcaaaccaa cccttggcag aacatatcca tcgcgtccgc    6120
catctccagc agccgcacgc ggcgcatctc gggcagcgtt gggtcctggc cacgggtgcg    6180
catgatcgtg ctcctgtcgt tgaggacccg gctaggctgg cggggttgcc ttactggtta    6240
```

```
gcagaatgaa tcaccgatac gcgagcgaac gtgaagcgac tgctgctgca aaacgtctgc    6300
gacctgagca acaacatgaa tggtcttcgg tttccgtgtt tcgtaaagtc tggaaacgcg    6360
gaagtcagcg ccctgcacca ttatgttccg gatctgcatc gcaggatgct gctggctacc    6420
ctgtggaaca cctacatctg tattaacgaa gcgctggcat tgaccctgag tgattttttct    6480 ctggtcccgc cgcatccata ccgccagttg tttaccctca caacgttcca gtaaccgggc    6540
atgttcatca tcagtaaccc cgtatcgtgag catcctctct cgtttcatcg gtatcattac    6600
ccccatgaac agaaatcccc cttacacgga ggcatcagtg accaaacagg aaaaaaccgc    6660
ccttaacatg gcccgcttta tcagaagcca gacattaacg cttctggaga aactcaacga    6720
gctggacgcg gatgaacagg cagacatctg tgaatcgctt cacgaccacg ctgatgagct    6780
ttaccgcagc gcgcagggtc agcctgaata cgcgtttaat gaccagcaca gtcgtgatgg    6840
caaggtcaga atagcgctga ggtctgcctc gtgaagaagg tgttgctgac tcataccagg    6900
cctgaatcgc cccatcatcc agccagaaag tgagggagcc acggttgatg agagcttgt    6960 tgtaggtgga ccagttggtg attttgaact tttgctttgc cacggaacgg tctgcgttgt    7020
cgggaagatg cgtgatctga tccttcaact cagcaaaagt tcgatttatt caacaaagcc    7080
acgttgtgtc tcaaaatctc tgatgttaca ttgcacaaga taaaaatata tcatcatgaa    7140
caataaaact gtctgcttac ataaacagta atacaagggg tgttatgagc catattcaac    7200
gggaaacgtc ttgctcgagg ccgcgattaa attccaacat ggatgctgat ttatatgggt    7260
ataaatgggc tcgcgataat gtcgggcaat caggtgcgac aatctatcga ttgtatggga    7320
agcccgatgc gccagagttg tttctgaaac atggcaaagg tagcgttgcc aatgatgtta    7380
cagatgagat ggtcagacta aactggctga cggaatttat gcctcttccg accatcaagc    7440
attttatccg tactcctgat gatgcatggt tactcaccac tgcgatcccc gggaaaacag    7500
cattccaggt attagaagaa tatcctgatt caggtgaaaa tattgttgat gcgctggcag    7560
tgttcctgcg ccggttgcat tcgattcctg tttgtaattg tccttttaac agcgatcgcg    7620
tatttcgtct cgctcaggcg caatcacgaa tgaataacgg tttggttgat gcgagtgatt    7680
ttgatgacga gcgtaatggc tggcctgttg aacaagtctg gaaagaaatg cataagcttt    7740
tgccattctc accggattca gtcgtcactc atggtgattt ctcacttgat aaccttattt    7800
ttgacgaggg gaaattaata ggttgtattg atgttggacg agtcggaatc gcagaccgat    7860
accaggatct tgccatccta tggaactgcc tcggtgagtt ttctccttca ttacagaaac    7920 ggcttttca aaaatatggt attgataatc ctgatatgaa taaattgcag tttcatttga    7980
tgctcgatga gttttctaa tcagaattgg ttaattggtt gtaacactgg cagagcatta    8040
cgctgacttg acgggacggc ggctttgttg aataaatcga acttttgctg agttgaagga    8100
tcagatcacg catcttcccg acaacgcaga ccgttccgtg gcaaagcaaa agttcaaaat    8160
caccaactgg tccacctaca acaaagctct catcaaccgt ggctccctca ctttctggct    8220
ggatgatggg gcgattcagg cctggtatga gtcagcaaca ccttcttcac gaggcagacc    8280
tcagcgctat tctgaccttg ccatcacgac tgtgctggtc attaaacgcg tattcaggct    8340
gaccctgcgc                                                          8350
```

<210> SEQ ID NO 106
<211> LENGTH: 3190
<212> TYPE: DNA
<213> ORGANISM: artificial
<220> FEATURE:

<223> OTHER INFORMATION: plasmid pAGR3

<400> SEQUENCE: 106

```
aagtgaccaa acaggaaaaa accgcccttca acatggcccg ctttatcaga agccagacat    60
taacgcttct ggagaaactc aacgagctgg acgcggatga acaggcagac atctgtgaat   120
cgcttcacga ccacgctgat gagctttacc gcagctgcct cgcgcgtttc ggtgatgacg   180
gtgaaaacct ctgacacatg cagctcccgg agacggtcac agcttgtctg taagcggatg   240
ccgggagcag acaagcccgt cagggcgcgt cagcgggtgt tggcgggtgt cggggcgcag   300
ccatgcccca gtcacgtagc gatagcggag tgtatactgg cttaactatg cggcatcaga   360
gcagattgta ctgagagtgc accatatgcg gtgtgaaata ccgcacagat gcgtaaggag   420
aaaataccgc atcaggcgct cttccgcttc ctcgctcact gactcgctgc gctcggtcgt   480
tcggctgcgg cgagcggtat cagctcactc aaaggcggta atacggttat ccacagaatc   540
aggggataac gcaggaaaga acatgtgagc aaaaggccag caaaaggcca ggaaccgtaa   600
aaaggccgcg ttgctggcgt ttttccatag gctccgcccc cctgacgagc atcacaaaaa   660
tcgacgctca agtcagaggt ggcgaaaccc gacaggacta taaagatacc aggcgtttcc   720
ccctggaagc tccctcgtgc gctctcctgt tccgaccctg ccgcttaccg gatacctgtc   780
cgcctttctc ccttcgggaa gcgtggcgct ttctcatagc tcacgctgta ggtatctcag   840
ttcggtgtag gtcgttcgct ccaagctggg ctgtgtgcac gaaccccccg ttcagcccga   900
ccgctgcgcc ttatccggta actatcgtct tgagtccaac ccggtaagac acgacttatc   960
gccactggca gcagccactg gtaacaggat tagcagagcg aggtatgtag gcggtgctac  1020
agagttcttg aagtggtggc ctaactacgg ctacactaga aggacagtat ttggtatctg  1080
cgctctgctg aagccagtta ccttcggaaa aagagttggt agctcttgat ccggcaaaca  1140
aaccaccgct ggtagcggtg ttttttttgt ttgcaagcag cagattacgc gcagaaaaaa  1200
aggatctcaa gaagatcctt tgatcttttc tacggggtct gacgctcagt ggaacgaaaa  1260
ctcacgttaa gggattttgg tcatgagatt atcaaaaagg atcttcacct agatcctttt  1320
aaattaaaaa tgaagtttta atcaatcta agtatatat gagtaaactt ggtctgacag  1380
ttaccaatgc ttaatcagtg aggcacctat ctcagcgatc tgtctatttc gttcatccat  1440
agttgcctga ctccccgtcg tgtagataac tacgatacgg gagggcttac catctggccc  1500
cagtgctgca atgataccgc gagacccacg ctcaccggct ccagatttat cagcaataaa  1560
ccagccagcc ggaagggccg agcgcagaag tggtcctgca actttatccg cctccatcca  1620
gtctattaat tgttgccggg aagctagagt aagtagttcg ccagttaata gtttgcgcaa  1680
cgttgttgcc attgctgcag gcatcgtggt gtcacgctcg tcgtttggta tggcttcatt  1740
cagctccggt tcccaacgat caaggcgagt tacatgatcc cccatgttgt gcaaaaaagc  1800
ggttagctcc ttcggtcctc cgatcgttgt cagaagtaag ttggccgcag tgttatcact  1860
catggttatg gcagcactgc ataattctct tactgtcatg ccatccgtaa gatgctttc  1920
tgtgactggt gagtactcaa ccaagtcatt ctgagaatag tgtatgcggc gaccgagttg  1980
ctcttgcccg gcgtcaacac gggataatac cgcgccacat agcagaactt taaaagtgct  2040
catcattgga aaacgttctt cggggcgaaa actctcaagg atcttaccgc tgttgagatc  2100
cagttcgatg taacccactc gtgcacccaa ctgatcttca gcatctttta ctttcaccag  2160
cgtttctggg tgagcaaaaa caggaaggca aaatgccgca aaaaagggaa taagggcgac  2220
acggaaatgt tgaatactca tactcttcct ttttcaatat tattgaagca tttatcaggg  2280
```

```
ttattgtctc atgagcggat acatatttga atgtatttag aaaaataaac aaatagggt    2340 tccgcgcaca tttccccgaa aagtgccacc tgacgtctaa gaaaccatta ttatcatgac   2400
attaacctat aaaaataggc gtatcacgag gcccttcgt cttcaagaat taattcccaa   2460
ttccaggcat caaataaaac gaaaggctca gtcgaaagac tgggccttc gttttatctg   2520 ttgtttgtcg gtgaacgctc tcctgagtag gacaaatccg ccgggagcgg atttgaacgt   2580
tgcgaagcaa cggcccggag ggtggcgggc aggacgcccg ccataaactg ccaggaatta   2640
attccaggca tcaaataaaa cgaaaggctc agtcgaaaga ctgggccttt cgttttatct   2700
gttgtttgtc ggtgaacgct ctcctgagta ggacaaatcc gccgggagcg gatttgaacg   2760
ttgcgaagca acggcccgga gggtggcggg caggacgccc gccataaact gccaggaatt   2820
aattccaggc atcaaataaa acgaaaggct cagtcgaaag actgggcctt tcgttttatc   2880
tgttgtttgt cggtgaacgc tctcctgagt aggacaaatc cgccgggagc ggatttgaac   2940
gttgcgaagc aacggcccgg agggtggcgg gcaggacgcc cgccataaac tgccaggaat   3000
taattccagg catcaaataa aacgaaaggc tcagtcgaaa gactgggcct ttcgtttat   3060 ctgttgtttg tcggtgaacg ctctcctgag taggacaaat ccgccgggag cggatttgaa   3120
cgttgcgaag caacggcccg gagggtggcg ggcaggacgc ccgccataaa ctgccaggaa   3180
ttggggatcg                                                         3190
```